(12) United States Patent
Ramsdell et al.

(10) Patent No.: US 7,618,629 B2
(45) Date of Patent: Nov. 17, 2009

(54) MANIPULATION OF CYTOKINE LEVELS USING CD83 GENE PRODUCTS

(75) Inventors: Fred Ramsdell, Bainbridge Island, WA (US); Sean C. Proll, Seattle, WA (US); Karen Staehling-Hampton, Bothell, WA (US); Mark W. Appleby, Shoreline, WA (US); Leon Fernando Garcia-Martinez, Woodinville, WA (US)

(73) Assignee: Celltech R&D, Inc., Bothell, WA (US)

( * ) Notice: Subject to any disclaimer, the term of this patent is extended or adjusted under 35 U.S.C. 154(b) by 94 days.

(21) Appl. No.: 10/496,284

(22) PCT Filed: Nov. 21, 2002

(86) PCT No.: PCT/US02/33738

§ 371 (c)(1),
(2), (4) Date: Sep. 30, 2005

(87) PCT Pub. No.: WO03/045318

PCT Pub. Date: Jun. 5, 2003

(65) Prior Publication Data

US 2006/0083740 A1 Apr. 20, 2006

Related U.S. Application Data

(60) Provisional application No. 60/331,958, filed on Nov. 21, 2001.

(51) Int. Cl.
*A61K 39/40* (2006.01)
*C07K 16/00* (2006.01)

(52) U.S. Cl. .............. 424/139.1; 424/141.1; 530/387.1; 530/388.1

(58) Field of Classification Search ........................ None
See application file for complete search history.

(56) References Cited

U.S. PATENT DOCUMENTS

| | | | | |
|---|---|---|---|---|
| 5,316,320 | A * | 5/1994 | Breaker | ...................... 277/611 |
| 5,316,920 | A | 5/1994 | Tedder et al. | |
| 5,766,570 | A | 6/1998 | Tedder et al. | |
| 6,068,984 | A | 5/2000 | Tedder | |
| 6,900,016 | B1 * | 5/2005 | Venter et al. | .................... 435/6 |

FOREIGN PATENT DOCUMENTS

| | | |
|---|---|---|
| WO | WO 95/029236 | 11/1995 |
| WO | WO 97/29781 | 8/1997 |
| WO | WO 02/074921 | 9/2002 |
| WO | WO 03/038072 | 5/2003 |
| WO | WO 03/040170 | 5/2003 |

OTHER PUBLICATIONS

Cramer, S. O. et al., Activation-Induced Expression of Murine CD83 on T Cells and Identification of a Specific CD83 Ligand on Murine B Cells, *International Immunology* 12(9):1347-1351, 2000.

Dreher, K. L. et al. cDNA Clone Encoding a Complete Rabbit Immunoglobulin K Light Chain of b4 Allotype, *Proc. Natl. Acad. Sci. USA* 80:4489-4493, Jul. 1983.

Fujimoto. Y. et al., Dendritic Cell CD83 Provides a Progression Signal Required for CD4+ T Cells Positive Selection in the Thymus, *FASEB Journal* 15(4):A672, 2001.

Fujimoto, Y. at al., CD83 Expression Influences CD4+ T Cell Development in the Thymus, *Cell* 108:755-767, 2002.

Jaton, J. C., Completion of the Analysis of the Primary Structure of the Variable Domain of a Homogeneous Rabbit Antibody to Type III Pneumococcal Polysaccharide, *Biochem. J.* 143:723-732, 1973.

Munster, D. J. et al., CD83 Antigen: A Potential New Target for Immunosuppression, *Blood* 100(11), 2002.

Scholler, N. et al., CD83 Is a Sialic Acid-Binding IG-Like Lectin (Siglec) Adhesion Receptor that Binds Monocytes and a Subset of Activated CD8+ T Cells, *Immunology* 166:3865-3872, 2001.

Armitage, R. J. et al., Evidence for a Functional Role of C083 in T- and B-Cell Responses, *Tissue Antigens* 4(11):453, Abstract.

Dallman, Current Opinion in Immunology, 7:632-638, 1995.

Gorczynski et al., Transplantation, 60(11):1337-1341,1995.

Leonard et al., J. Exp. Med., 181:381-386, 1995.

Levy et al., Transplantation, 60(5):405-406, 1995.

Thai et al., Transplantation, 59(2):274-281, 1995.

Zhou et al., The Journal of Immunology, 3821-3835, 1995.

Chen et al., Immunity, 1:147-154, 1994.

Else et al., J. Exp. Med., 179:347-351, 1994.

Fowler et al., Blood, 84(10):3540-3549, 1994:.

Fowler et al., Advances in Bone Marrow Purging and Processing: Fourth International Symposium, 533-540, 1994.

Maeda et al., International Immunology, 6(6):855-862, 1994.

Paul et al., Cell, 76:241-251, 1994.

Racke et al., J. Exp. Med., 180:1961-1966, 1994.

Simon et al., Proc. Natl. Acad. Sci. USA, 91(18):8562-8566, 1994.

Tkakis et al., Journal of Pediatric Surgery, 29(6):754-756, 1994.

Seder et al., Annu. Rev. Immunol., 12:635-673, 1994.

Bancroft et al., The Journal of Immunology, 150(4):1395-1402, 1993.

Clerici et al., Immunology Today, 14(3):107-111, 1993.

Kuchroo et al., The Journal of Immunology, 151(8):4371-4382, 1993.

(Continued)

*Primary Examiner*—Michail A Belyavskyi
(74) *Attorney, Agent, or Firm*—K&L Gates LLP

(57) ABSTRACT

The invention provides methods for modulating cytokine levels, GM-CSF levels and the immune system using CD83 nucleic acids, CD83 polypeptides, anti-CD83 antibodies and factors that influence CD83 activity or expression. The invention also provides mice having a mutant CD83 gene and mice having a transgenic CD83 gene, which are useful for defining the role of CD83 in the immune system and for identifying compounds that can modulate CD83 and the immune system.

35 Claims, 20 Drawing Sheets

OTHER PUBLICATIONS

Pearlman et al., Infection and Immunity, 61(3):1105-1112, 1993.
Rapoport et al., J. Exp. Med., 178:87-99, 1993.
Yamamura et al., Journal of Clinical Investigation, 91:1005-1010, 1993.
Khoury et al., J. Exp. Med., 176:1355-1364, 1992.
Kullberg et al., The Journal of Immunology, 148(10):3264-3270, 1992.
Pisa et al., Proc. Natl. Acad. Sci. USA, 89:7708-7712, 1992.
Shearer et al., Chem. Immunol., 54:21-43, 1992.
Takeuchi et al., Transplantation, 53(6):1281-1294, 1992.
Zhou et al., The Journal of Immunology, 149(2):735-742, 1992.
Grzych et al., The Journal of Immunology, 146(4):1322-1327, 1991.
Locksley et al., T-Cell Subsets, A58-A61, 1991.
Pearce et al., J. Exp. Med., 173:159-166, 1991.
Sadick et al., J. Exp. Med., 171:115-127, 1990.
Heinzel et al., J. Exp. Med., 169:59-72, 1989.
Schwartz et al., Fundamental Immunology, Second Edition:New York, 819-856, 1989.
Fauci, Science, 239:617-622, 1988.
Morrissey et al., The Journal of Immunology, 139(4):1113-1119, 1987.
Mosmann et al., The Journal of Immunology, 136(7):2348-2357, 1986.

* cited by examiner

|  | Mom | G3 ID | % CD4+ |
|---|---|---|---|
| Pedigree 57 | G2 # 1 | 57.1.1 | 22 |
|  |  | 57.1.2 | 26 |
|  |  | 57.1.3 | 24 |
|  | G2 # 4 | 57.4.1 | 15 |
|  |  | 57.4.2 | 18 |
|  | G2 # 5 | 57.5.1 | 21 |
|  |  | 57.5.2 | 19 |
|  |  | 57.5.3 | 24 |
|  |  | 57.5.4 | 22 |
|  |  | 57.5.5 | 19 |
|  |  | 57.5.6 | 17 |
| Pedigree 9 | G2 # 4 | 9.4.1 | 6 |
|  |  | 9.4.2 | 20 |
|  |  | 9.4.3 | 16 |
|  |  | 9.4.4 | 12 |
|  |  | 9.4.5 | 20 |
|  |  | 9.4.6 | 15 |
|  |  | 9.4.7 | 24 |
|  |  | 9.4.8 | 27 |
|  |  | 9.4.9 | 5 |
|  | G2 # 5 | 9.5.1 | 18 |
|  |  | 9.5.2 | 20 |
|  |  | 9.5.3 | 22 |
|  |  | 9.5.4 | 20 |
|  |  | 9.5.5 | 22 |
|  |  | 9.5.6 | 20 |
|  |  | 9.5.7 | 23 |

| average | 19.1 |
|---|---|
| stdev | 5.2 |
| = + 2SD | 29.6 |
| = -2SD | 8.7 |

FIG. 1

```
1    GCGCTCCAGC CGCATGTCGC AAGGCCTCCA GCTCCTGTTT CTAGGCTGCG
51   CCTGCAGCCT GGCACCCGCG ATGGCGATGC GGGAGGTGAC GGTGGCTTGC
101  TCCGAGACCG CCGACTTGCC TTGCACAGCG CCCTGGGACC CGCAGCTCTC
151  CTATGCAGTG TCCTGGGCCA AGGTCTCCGA GAGTGGCACT GAGAGTGTGG
201  AGCTCCGGA GAGCAAGCAA AACAGCTCCT TCGAGGCCCC CAGGAGAAGG
251  GCCTATTCCC TGACGATCCA AAACACTACC ATCTGCAGCT CGGGCACCTA
301  CAGGTGTGCC CTGCAGGAGC TCGGAGGGCA GCGCAACTTG AGCGGCACCG
351  TGGTTCTGAA GGTGACAGGA TGCCCCAAGG AAGCTACAGA GTCAACTTTC
401  AGGAAGTACA GGGCAGAAGC TGTGTTGCTC TTCTCTCTGG TTGTTTTCTA
451  CCTGACACTC ATCATTTTCA CCTGCAAATT TGCACGACTA CAAAGCATTT
501  TCCCAGATAT TTCTAAACCT GGTACGGAAC AAGCTTTTCT TCCAGTCACC
551  TCCCCAAGCA ACATTTGGG GCCAGTGACC CTTCCTAAGA CAGAAACGGT
601  ATGAGTAGGA TCTCCACTGG TTTTTACAAA GCCAAGGGCA CATCAGATCA
651  GTGTGCCTGA ATGCCACCCG GACAAGAGAA GAATGAGCTC ATCCTCAGA
701  TGGCAACCTT TCTTTGAAGT CCTTCACCTG ACAGTGGGCT CCACACTACT
751  CCCTGACACA GGGTCTTGAG CACCATCATA TGATCACGAA GCATGGAGTA
801  TCACCGCTTC TCTGTGGCTG TCAGCTTAAT GTTTCATGTG GCTATCTGGT
851  CAACCTCGTG AGTGCTTTTC AGTCATCTAC AAGCTATGGT GAGATGCAGG
901  TGAAGCAGGG TCATGGGAAA TTTGAACACT CTGAGCTGGC CCTGTGACAG
951  ACTCCTGAGG ACAGCTGTCC TCTCCTACAT CTGGGATACA TCTCTTTGAA
1001 TTTGTCCTGT TTCGTTGCAC CAGCCCAGAT GTCTCACATC TGGCGGAAAT
1051 TGACAGGCCA AGCTGTGAGC CAGTGGGAAA TATTTAGCAA ATAATTTCCC
1101 AGTGCGAAGG TCCTGCTATT AGTAAGGAGT ATTATGTGTA CATAGAAATG
1151 AGAGGTCAGT GAACTATTCC CCAGCAGGGC CTTTTCATCT GGAAAAGACA
1201 TCCACAAAAG CAGCAATACA GAGGGATGCC ACATTTATTT TTTTAATCTT
1251 CATGTACTTG TCAAAGAAGA ATTTTTCATG TTTTTTCAAA GAAGTGTGTT
1301 TCTTTCCTTT TTTAAAATAT GAAGGTCTAG TTACATAGCA TTGCTAGCTG
1351 ACAAGCAGCC TGAGAGAAGA TGGAGAATGT TCCTCAAAAT AGGGACAGCA
1401 AGCTAGAAGC ACTGTACAGT GCCCTGCTGG GAAGGGCAGA CAATGGACTG
1451 AGAAACCAGA AGTCTGGCCA AAGATTGTC TGTATGATTC TGGACGAGTC
1501 ACTTGTGGTT TCACTCTCT GGTTAGTAAA CCAGATAGTT TAGTCTGGGT
1551 TGAATACAAT GGATGTGAAG TTGCTTGGGG AAAGCTGAAT GTAGTGAATA
1601 CATTGGCAAC TCTACTGGGC TGTTACCTTG TTGATATCCT AGAGTTCTGG
1651 AGCTGAGCGA ATGCCTGTCA TATCTCAGCT TGCCCATCAA TCCAAACACA
1701 GGAGGCTACA AAAGGACAT GAGCATGGTC TTCTGTGTGA ACTCCTCCTG
1751 AGAAACGTGG AGACTGGCTC AGCGCTTTGC GCTTGAAGGA CTAATCACAA
1801 GTTCTTGAAG ATATGGACCT AGGGGAGCTA TTGCGCCACG ACAGGAGGAA
1851 GTTCTCAGAT GTTGCATTGA TGTAACATTG TTGCATTTCT TTAATGAGCT
1901 GGGCTCCTTC CTCATTTGCT TCCCAAAGAG ATTTTGTCCC ACTAATGGTG
1951 TGCCCATCAC CCACACTATG AAAGTAAAAG GGATGCTGAG CAGATACAGC
2001 GTGCTTACCT CTCAGCCATG ACTTTCATGC TATTAAAAGA ATGCATGTGA
2051 A
```

FIG. 3

| | | | | | |
|---|---|---|---|---|---|
| 1 | GCGCTCCAGC | CGCATGTCGC | AAGGCCTCCA | GCTCCTGTTT | CTAGGCTGCG |
| 51 | CCTGCAGCCT | GGCACCCGCG | ATGGCGATGC | GGGAGGTGAC | GGTGGCTTGC |
| 101 | TCCGAGACCG | CCGACTTGCC | TTGCACAGCG | CCCTGGGACC | CGCAGCTCTC |
| 151 | CTATGCAGTG | TCCTGGGCCA | AGGTCTCCGA | GAGTGGCACT | GAGAGTGTGG |
| 201 | AGCTCCCGGA | GAGCAAGCAA | ACAGCTCCT | TCGAGGCCCC | CAGGAGAAGG |
| 251 | GCCTATTCCC | TGACGATCCA | AAACACTACC | ATCTGCAGCT | CGGGCACCTA |
| 301 | CAGGTGTGCC | CTGCAGGAGC | TCGGAGGGCA | GCGCAACTTG | AGCGGCACCG |
| 351 | TGGTTCTGAA | GGTGACAGGA | TGCCCCAAGG | AAGCTACAGA | GTCAACTTTC |
| 401 | AGGAAGTACA | GGGCAGAAGC | TGTGTTGCTC | TTCTCTCTGG | TTGTTTTCTA |
| 451 | CCTGACACTC | ATCATTTTCA | CCTGCAAATT | TGCACGACTA | CAAAGCATTT |
| 501 | TCCCAGATAT | TTCTAAACCT | GGTACGGAAC | AAGCTTTTCT | TCCAGTCACC |
| 551 | TCCCCAAGCA | ACATTTGGG | GCCAGTGACC | CTTCCTAAGA | CAGAAACGGT |
| 601 | AAGAGTAGGA | TCTCCACTGG | TTTTTACAAA | GCCAAGGGCA | CATCAGATCA |
| 651 | GTGTGCCTGA | ATGCCACCCG | GACAAGAGAA | GAATGAGCTC | CATCCTCAGA |
| 701 | TGGCAACCTT | TCTTTGAAGT | CCTTCACCTG | ACAGTGGGCT | CCACACTACT |
| 751 | CCCTGACACA | GGGTCTTGAG | CACCATCATA | TGATCACGAA | GCATGGAGTA |
| 801 | TCACCGCTTC | TCTGTGGCTG | TCAGCTTAAT | GTTTCATGTG | GCTATCTGGT |
| 851 | CAACCTCGTG | AGTGCTTTTC | AGTCATCTAC | AAGCTATGGT | GAGATGCAGG |
| 901 | TGAAGCAGGG | TCATGGGAAA | TTTGAACACT | CTGAGCTGGC | CCTGTGACAG |
| 951 | ACTCCTGAGG | ACAGCTGTCC | TCTCCTACAT | CTGGGATACA | TCTCTTTGAA |
| 1001 | TTTGTCCTGT | TTCGTTGCAC | CAGCCCAGAT | GTCTCACATC | TGGCGGAAAT |
| 1051 | TGACAGGCCA | AGCTGTGAGC | CAGTGGGAAA | TATTTAGCAA | ATAATTTCCC |
| 1101 | AGTGCGAAGG | TCCTGCTATT | AGTAAGGAGT | ATTATGTGTA | CATAGAAATG |
| 1151 | AGAGGTCAGT | GAACTATTCC | CCAGCAGGGC | CTTTTCATCT | GGAAAAGACA |
| 1201 | TCCACAAAAG | CAGCAATACA | GAGGGATGCC | ACATTTATTT | TTTTAATCTT |
| 1251 | CATGTACTTG | TCAAAGAAGA | ATTTTTCATG | TTTTTTCAAA | GAAGTGTGTT |

FIG. 4A

```
1301 TCTTTCCTTT TTTAAAATAT GAAGGTCTAG TTACATAGCA TTGCTAGCTG
1351 ACAAGCAGCC TGAGAGAAGA TGGAGAATGT TCCTCAAAAT AGGGACAGCA
1401 AGCTAGAAGC ACTGTACAGT GCCCTGCTGG GAAGGGCAGA CAATGGACTG
1451 AGAAACCAGA AGTCTGGCCA CAAGATTGTC TGTATGATTC TGGACGAGTC
1501 ACTTGTGGTT TTCACTCTCT GGTTAGTAAA CCAGATAGTT TAGTCTGGGT
1551 TGAATACAAT GGATGTGAAG TTGCTTGGGG AAAGCTGAAT GTAGTGAATA
1601 CATTGGCAAC TCTACTGGGC TGTTACCTTG TTGATATCCT AGAGTTCTGG
1651 AGCTGAGCGA ATGCCTGTCA TATCTCAGCT TGCCCATCAA TCCAAACACA
1701 GGAGGCTACA AAAGGACAT GAGCATGGTC TTCTGTGTGA ACTCCTCCTG
1751 AGAAACGTGG AGACTGGCTC AGCGCTTTGC GCTTGAAGGA CTAATCACAA
1801 GTTCTTGAAG ATATGGACCT AGGGGAGCTA TTGCGCCACG ACAGGAGGAA
1851 GTTCTCAGAT GTTGCATTGA TGTAACATTG TTGCATTTCT TTAATGAGCT
1901 GGGCTCCTTC CTCATTTGCT TCCCAAAGAG ATTTTGTCCC ACTAATGGTG
1951 TGCCCATCAC CCACACTATG AAAGTAAAAG GGATGCTGAG CAGATACAGC
2001 GTGCTTACCT CTCAGCCATG ACTTTCATGC TATTAAAAGA ATGCATGTGA
2051 A
```

FIG. 4B

Wild Type Amino Acid Sequence for CD83 protein [Mus musculus]
MSQGLQLLFL GCACSLAPAM AMREVTVACS ETADLPCTAP WDPQLSYAVS
WAKVSESGTE SVELPESKQN SSFEAPRRRA YSLTIQNTTI CSSGTYRCAL
QELGGQRNLS GTVVLKVTGC PKEATESTFR KYRAEAVLLF SLVVFYLTLI
IFTCKFARLQ SIFPDISKPG TEQAFLPVTS PSKHLGPVTL PKTETV

Mutant CD83 Amino Acid Sequence: novel tail underlined, in bold.
MSQGLQLLFL GCACSLAPAM AMREVTVACS ETADLPCTAP WDPQLSYAVS
WAKVSESGTE SVELPESKQN SSFEAPRRRA YSLTIQNTTI CSSGTYRCAL
QELGGQRNLS GTVVLKVTGC PKEATESTFR KYRAEAVLLF SLVVFYLTLI
IFTCKFARLQ SIFPDISKPG TEQAFLPVTS PSKHLGPVTL PKTETV<u>RVGS</u>
<u>PLVFTKPRAH QISVPECHPD KRRMSSILRW QPFFEVLHLT VGSTLLPDTG</u>
<u>S</u>

FIG. 5

```
                       CDR1                                                              CDR2
20B08H   METGLRWLLLLVAVLKGVQCQSVEESGGRLVTPGTPLTLTCTVSGFSLSSYDMTWVRQAPGKGLEWIGIIYAS-
 6G05H   METGLRWLLLLVAVLKGVQCQSVEESGGRLVTPGTPLTLTCTASGFSLSSYDMSWVRQAPGKGLEYIGIISSS-
20D04H   METGLRWLLLLVAVLKGVQCQSVEESGGRLVTPGTPLTLTCTVSGFSLSSYDMSWVRQAPGKGLEWIGIIYAS-
11G05    METGLRWLLLLVAVLKGVQCQSVEESGGRLVTPGTPLTLTCTVSGFTISDYDLSWVRQAPGEGLKYIGFIAID-
14C12    METGLRWLLLLVAVLKGVHCQSVEESGGRLVTPGTPLTLTCTASGFSRSSYDMSWVRQAPGKGLEWVGVISTA-

CDR3
20B08H   GSTYYASWAKGRFTISKTSTTVDLEVTSLTTEDTATYFCSREHAGYSGDTGHLWGPGTLVTVSSGQPKAPSVF
 6G05H   GTTYYANWAKGRFTISKTSTTVDLKVTSPTIGDTATYFCAREGAGVSMT---LWGPGTLVTVSSGQPKAPSVF
20D04H   GSTYYASWAKGRVAISKTSTTVDLKITSPTTEDTATYFCAREDAGFSNA---LWGPGTLVTVSSGQPKAPSVF
11G05    GNPYYATWAKGRFTISKTSTTVDLKITAPTTEDTATYFCARGAGD-------LWGPGTLVTVSSGQPKAPSVF
14C12    YNSHYASWAKGRFTISRTSTTVDLKMTSLTTEDTATYFCARGGSWLD-----LWGQGTLVTVSSGQPKAPSVF

20B08H   PLAPCCGDTPSS
 6G05H   PLAPCCGDTPSS
20D04H   PLAPCCGDTPSS
11G05    PLAPCCGDTPSS
14C12    PLAPCCGDTPSS
```

FIG. 17A

```
                              CDR1                                                    CDR2
20B08L    MDMRAPTQLLGLILLLLWLPGARC-AYDMTQTQTPASVEVAVGGTVTIKCQASQSISTY---
6G05L     MDMRAPTQLLGLILLLLWLPGARC-AYDMTQTQTPASVEVAVGGTVAIKCQASQSVSSY---
20D04L    MDMRAPTQLLGLILLLLWLPGARCADVVMTQTPASVSAAVGGTVTINCQASESISNY---
11G05L    MDTRAPTQLLGLILLLLWLPGARCADVVMTQTPASVSAAVGGTVTINCQSSKNVYNNNW
14C12L    MDXRAPTQLLGLILLLLWLPGARCA-LVMTQTPASVSAAVGGTVTINCQSSQSVYDNDE

CDR3
20B08L    LDWYQQKPGQPPKLLIYDASDLASGVPSRFKGSGSGTQFTLTISDLECADAATYYCQQGYT---
6G05L     LAWYQQKPGQPPKPLIYEASMLAAGVSSRFKGSGSGTDFTLTISDLECDDAATYYCQQGYS---
20D04L    LSWYQQKPGQPPKLLIYRTSTLASGVSSRFKGSGSGTEYTLTISGVQCDDVATYYCQCTSGG-
11G05L    LSWFQQKPGQPPKLLIYYASTLASGVPSRFRGSGSGTQFTLTISDVQCDDAATYYCAG-DYSS--S
14C12L    LSWYQQKPGQPPKLLIYLASKLASGVPSRFKGSGSGTQFALTISGVQCDDAATYYCQATHYSS--D-

20B08L    -HSNVDNVFGGGTEVVVKGDPVAPTVLLFPPSS
6G05L     -ISDIDNAFGGGTEVVVKGDPVAPTVLLFPPSS
20D04L    KFISDGAAFGGGTEVVVKGDPVAPTVLLFPPSS
11G05L        SDNGFGGGTEVVVKGDPVAPTVLLFPPSS
14C12L         WYLTFGGGTEVVVKGDPVAPTVLLFPPSS
```

MANIPULATION OF CYTOKINE LEVELS USING CD83 GENE PRODUCTS

This application is related to U.S. Application Ser. No. 60/331,958 filed Nov. 21, 2001.

FIELD OF THE INVENTION

The invention relates to an altered CD83 gene product, and methods of modulating cytokine levels by modulating the expression of mutant and wild type CD83 gene products produced in a mammal. The invention also relates to the regulation of T cell and dendritic cell activity and conditions and treatments related thereto.

BACKGROUND OF THE INVENTION

CD83 is a 45 kilodalton glycoprotein that is predominantly expressed on the surface of dendritic cells and other cells of the immune system. Structural analysis of the predicted amino acid sequence of CD83 indicates that it is a member of the immunoglobulin superfamily. See, Zhou et al., J. Immunol. 149:735 (1992)). U.S. Pat. No. 5,316,920 and WO 95/29236 disclose further information about CD83. While such information suggests that CD83 plays a role in the immune system, that role is undefined, and the interrelationship of CD83 with cellular factors remains unclear.

Moreover, treatment of many diseases could benefit from more effective methods for increasing or decreasing the immune response. Hence, further information about how to modulate the immune system by using factors such as CD83 are needed.

SUMMARY OF THE INVENTION

The invention provides a method of modulating cytokine levels by modulating the activity or expression of the CD83 gene products. According to the invention, cytokine levels can be modulated in a mammal or in mammalian cells that are involved in the immune response, for example, antigen presenting cells or T cells.

The invention therefore provides a method of modulating cytokine production in a mammal or in an immune cell by modulating the activity or expression of a CD83 polypeptide. According to the invention, the production of a cytokine such as interleukin-2, interleukin-4, or interlekin-10 can be modulated by modulating the activity or expression of a CD83 polypeptide. In some embodiments, an antibody is used that can modulate the activity or expression of a CD83 polypeptide. For example, the antibody can be administered to the mammal or the immune cell can be contacted with the antibody. In some embodiments, the immune cells are T cells or antigen presenting cells. In other embodiments, the immune cells are CD4+ T cells.

The invention also provides a method of modulating granulocyte macrophage colony stimulating factor production in a mammal or in an immune cell by modulating the activity or expression of CD83 polypeptides. In some embodiments, an antibody is used that can modulate the activity or expression of a CD83 polypeptide. For example, the antibody can be administered to the mammal or the immune cell can be contacted with the antibody. In some embodiments, the immune cells are T cells or antigen presenting cells. In other embodiments, the immune cells are CD4+ T cells.

The invention also provides a method of modulating tumor necrosis factor production in a mammal or in a mammalian cell by modulating the activity or expression of CD83 polypeptides. In some embodiments, an antibody is used that can modulate the activity or expression of a CD83 polypeptide. For example, the antibody can be administered to the mammal or the mammalian cell can be contacted with the antibody. In some embodiments, the immune cells are T cells or antigen presenting cells. In other embodiments, the immune cells are CD4+ T cells.

The invention further provides a method of inhibiting proliferation of a human peripheral blood mononuclear cell by modulating the activity or expression of CD83 polypeptides. In some embodiments, an antibody is used that can modulate the activity or expression of a CD83 polypeptide. For example, the antibody can be administered to the mammal or the human peripheral blood mononuclear cell can be contacted with the antibody.

The invention also provides an antibody that can bind to a CD83 polypeptide comprising SEQ ID NO:4, SEQ ID NO:8 or SEQ ID NO:9, wherein activated CD4+ T-cells produce lower levels of interleukin-4 when the T-cells are contacted with the antibody. The invention further provides an antibody that can bind to a CD83 polypeptide comprising SEQ ID NO:4, SEQ ID NO:8 or SEQ ID NO:9, wherein CD4+ T-cells proliferation is decreased when the T-cells are contacted with the antibody. Such an antibody can have an amino acid sequence that includes SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62 or SEQ ID NO:64. Nucleic acids encoding such an antibody can have, for example, a sequence that includes SEQ ID NO:12, SEQ ID NO:14, SEQ ID NO:16, SEQ ID NO:18, SEQ ID NO:20, SEQ ID NO:22, SEQ ID NO:59, SEQ ID NO:61, SEQ ID NO:63 or SEQ ID NO:65.

The invention also provides a method for decreasing the activity of a CD83 gene product, comprising contacting the CD83 gene product with an antibody that comprises SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62 or SEQ ID NO:64. The activity of a CD83 gene product can be decreased in a mammal or in a cell that is involved in an immune response, for example, a T cell.

The invention further provides a method for decreasing the translation of a CD83 gene product in a mammalian cell, comprising contacting the mammalian cell with a nucleic acid complementary to a CD83 nucleic acid comprising SEQ ID NO:1, SEQ ID NO:3, SEQ ID NO:5, or SEQ ID NO:10.

In another embodiment, the invention provides a method for decreasing the translation of a CD83 gene product in a mammal, comprising administering to the mammal a nucleic acid complementary to a CD83 nucleic acid comprising SEQ ID NO:1, SEQ ID NO:3, SEQ ID NO:5, or SEQ ID NO:10.

The invention further provides a method for decreasing proliferation of CD4+ T-cells in a mammal comprising administering to the mammal an antibody that can bind to a CD83 gene product, wherein the CD83 gene product comprises SEQ ID NO:2 or SEQ ID NO:9. The antibody can have a sequence comprising SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62 or SEQ ID NO:64.

The invention also provides a method for decreasing interleukin-2 levels and increasing interleukin-4 levels in a mammal comprising administering to the mammal an antibody that can bind to a CD83 gene product, wherein the CD83 gene product comprises SEQ ID NO:2 or SEQ ID NO:9. The antibody can have a sequence comprising SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62 or SEQ ID NO:64.

The invention further provides a method for decreasing interleukin-2 levels and increasing interleukin-4 levels in a mammal comprising administering to the mammal a nucleic acid complementary to a CD83 nucleic acid comprising SEQ ID NO:1, SEQ ID NO:3, SEQ ID NO:5, or SEQ ID NO:10. In some embodiments the interleukin-2 levels are decreased and the interleukin-4 levels are increased to treat an autoimmune disease. In other embodiments, the interleukin-2 levels are decreased and the interleukin-4 levels are increased to stimulate production of Th2-associated cytokines in transplant recipients, for example, to prolong survival of transplanted tissues.

The invention also provides a method for increasing interleukin-10 levels in a mammal comprising administering to the mammal an antibody that can bind to a CD83 gene product, wherein the CD83 gene product comprises SEQ ID NO:2 or SEQ ID NO:9. The antibody can have a sequence comprising SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62 or SEQ ID NO:64.

The invention further provides a method for increasing interleukin-10 levels in a mammal comprising administering to the mammal a nucleic acid complementary to a CD83 nucleic acid comprising SEQ ID NO:1, SEQ ID NO:3, SEQ ID NO:5, or SEQ ID NO:10. In some embodiments, the interleukin-10 levels are increased to treat neoplastic disease. In other embodiments, the interleukin-10 levels are increased to treat a tumor.

The invention also provides a method for increasing interleukin-2 levels in a mammal comprising administering to the mammal a functional CD83 polypeptide that comprises SEQ ID NO:9.

The invention further provides a method for increasing interleukin-2 levels in a mammal comprising: (a) transforming a T cell from the mammal with a nucleic acid encoding a functional CD83 polypeptide operably linked to a promoter functional in a mammalian cell, to generate a transformed T cell; (b) administering the transformed T cell to the mammal to provide increased levels of interleukin-2. In some embodiments, the CD83 polypeptide has a sequence that comprises SEQ ID NO:9 or the nucleic acid has a sequence that comprises SEQ ID NO:1, SEQ ID NO:3, SEQ ID NO:5, or SEQ ID NO:10. Such methods for increasing interleukin-2 levels can be used to treat an allergy or an infectious disease.

The invention also provides a method for increasing granulocyte macrophage colony stimulating factor levels in a mammal comprising administering to the mammal an antibody that can bind to a CD83 gene product, wherein the CD83 gene product comprises SEQ ID NO:2 or SEQ ID NO:9. Such an antibody can have a sequence comprising SEQ ID NO:11, SEQ ID NO:13, SEQ ID NO:15, SEQ ID NO:17, SEQ ID NO:19, SEQ ID NO:21, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:62 or SEQ ID NO:64.

The invention further provides a method for increasing granulocyte macrophage colony stimulating factor levels in a mammal comprising administering to the mammal a nucleic acid complementary to a CD83 nucleic acid comprising SEQ ID NO:1, SEQ ID NO:3, SEQ ID NO:5, or SEQ ID NO:10.

The invention also provides a method for increasing tumor necrosis factor levels at a selected site in a mammal comprising administering to the site a functional CD83 polypeptide. In another embodiment, the invention provides a method for increasing tumor necrosis factor levels in a selected mammalian cell comprising transforming the cell with a nucleic acid encoding a functional CD83 polypeptide. The CD83 polypeptide employed can, for example, have a sequence comprising SEQ ID NO:9.

Mammals and birds may be treated by the methods and compositions described and claimed herein. Such mammals and birds include humans, dogs, cats, and livestock, for example, horses, cattle, sheep, goats, chickens, turkeys and the like.

The invention further provides a mutant mouse that can serve as an animal model of diminished T cell activation or altered cytokine levels. The mutant mouse has an altered CD83 gene that produces a larger gene product, having SEQ ID NO:4 or containing SEQ ID NO:8. Also provided are methods of using the mutant mouse model to study the effects of cytokines on the immune system, inflammation, the function and regulation of CD83, T cell and dendritic cell activity, the immune response and conditions and treatments related thereto. Hence, the invention further provides a mutant mouse whose somatic and germ cells comprise a mutant CD83 gene encoding a polypeptide comprising SEQ ID NO:4 or SEQ ID NO:8, wherein expression of the mutant CD83 gene reduces CD4+T cell activation. The mutant CD83 gene can, for example, comprise SEQ ID NO:3.

The invention further provides a method of identifying a compound that can modulate CD4+T cell activation comprising administering a test compound to a mouse having a mutant or wild type transgenic CD83 gene and observing whether CD4+ T cell activation is decreased or increased. The somatic and/or germ cells of the mutant mouse can comprise a mutant CD83 gene encoding a polypeptide comprising SEQ ID NO:4 or SEQ ID NO:8. Alternatively, the somatic and/or germ cells of the mouse can contain a wild type CD83 gene, for example, SEQ ID NO:1 or SEQ ID NO:9.

The invention also provides a mutant CD83 gene encoding a polypeptide comprising SEQ ID NO:4 or SEQ ID NO:8. The invention further provides a mutant CD83 gene comprising nucleotide sequence SEQ ID NO:3.

DESCRIPTION OF THE FIGURES

FIG. 1 provides flow cytometry data for G3 animals. As shown, reduced numbers of CD4+ T cells are seen in two animals from Pedigree 9, mouse 9.4.1 and mouse 9.4.9. All other animals analyzed on that day exhibit normal numbers of CD4+ T cells.

FIG. 3 provides the nucleotide sequence of wild type mouse CD83 (SEQ ID NO:1). The ATG start codon and the TGA stop codon are underlined.

FIG. 4A-B provides the nucleotide sequence of the mutant CD83 gene (SEQ ID NO:3) of the invention derived from the mutant LCD4.1 animal. The ATG start codon, the mutation and the TGA stop codon are underlined.

FIG. 5 provides the amino acid sequence for wild type (top, SEQ ID NO:2) and mutant (bottom, SEQ ID NO:4) CD83 coding regions. The additional C-terminal sequences arising because of the CD83 mutation are underlined.

FIG. 17A provides a sequence alignment of anti-CD83 heavy chain variable regions isolated by the invention. Sequences for isolates 20B08H (SEQ ID NO:52), 6G5H (SEQ ID NO:53), 20D04H (SEQ ID NO:54), 11G05 (SEQ ID NO:66) and 14C12 (SEQ ID NO:67) are provided. The CDR regions are highlighted in bold.

FIG. 17B provides a sequence alignment of anti-CD83 light chain variable regions isolated by the invention. Sequences for isolates 20B08H (SEQ ID NO:55), 6G05H (SEQ ID NO:56), 20D04H (SEQ ID NO:57), 11G05 (SEQ ID NO:68) and 14C12 (SEQ ID NO:69) are provided. The CDR regions are highlighted in bold.

DETAILED DESCRIPTION OF THE INVENTION

Figure 2:
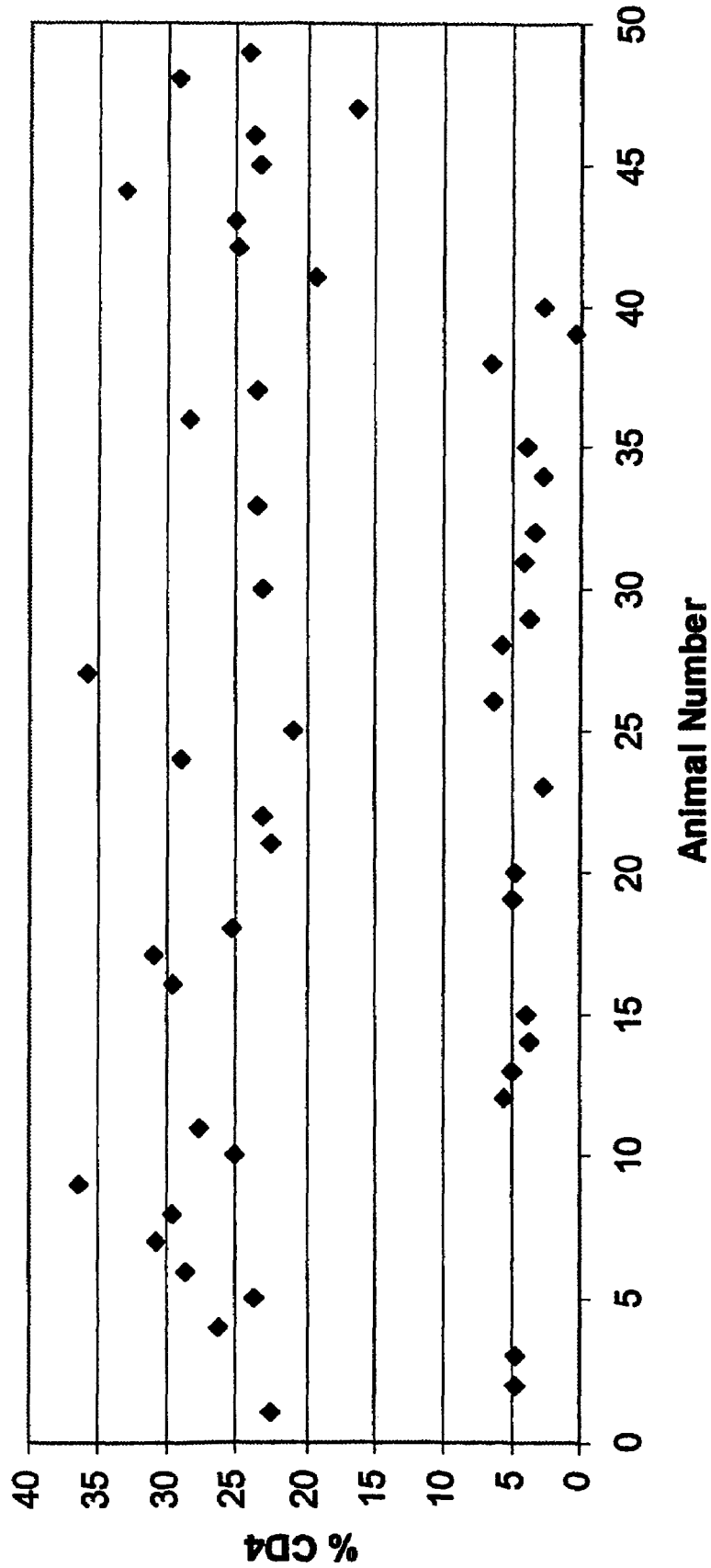
FIG. 2 provides a graph of flow cytometry data for G3 animals. Each diamond symbol represents an individual animal. As shown, multiple animals from the N2 generation exhibit a reduced percentage of CD4+ T cells.

The invention provides methods for modulating the immune system by using CD83 proteins, CD83 nucleic acids and factors that modulate CD83 activity or expression.

According to the invention, loss or reduction of CD83 activity in vivo results in altered cytokine levels, for example, lower interleukin-2 levels, increased interleukin-4 levels, increased GM-CSF levels and increased interleukin-10 levels. Loss or reduction of CD83 activity in vivo can also result in decreased numbers of T cells.

Moreover, the invention also relates to increased CD83 activity in vivo that can result in altered cytokine levels, for example, higher interleukin-2 levels, decreased interleukin-4 levels, decreased GM-CSF levels and decreased interleukin-10 levels. Increased CD83 expression or activity in vitro and in vivo can also result in increased activation and increased numbers of T cells.

The effects of CD83 on the immune system, on GM-CSF and on cytokine levels were analyzed by using mutant and transgenic mice. The mutant mouse has an altered CD83 gene that expresses altered (defective) CD83 gene product. The transgenic mouse overexpresses CD83 gene products. Accordingly, the invention provides mammals such as mice that have a mutant or wild type CD83 gene. These mice are useful for identifying the role that CD83 plays in the immune response. These mutant and transgenic animals are useful for identifying factors for manipulating cytokine levels and T cell activation by testing whether those factors and compositions can modulate, inhibit or replace the activity of CD83 in vivo.

CD83

CD83 is a lymphocyte and dendritic cell activation antigen that is expressed by activated lymphocytes and dendritic cells. CD83 is also a single-chain cell-surface glycoprotein with a molecular weight of about 45,000 that is believed to be a member of the Ig superfamily. The structure predicted from the CD83 amino acid sequence indicates that CD83 is a membrane glycoprotein with a single extracellular Ig-like domain, a transmembrane domain and cytoplasmic domain of approximately forty amino acids. The mature CD83 protein has about 186 amino acids and is composed of a single extracellular V type immunoglobulin (Ig)-like domain, a transmembrane domain and a thirty nine amino acid cytoplasmic domain. Northern blot analysis has revealed that CD83 is translated from three mRNA transcripts of about 1.7, 2.0 and 2.5 kb that are expressed by lymphoblastoid cell lines. It is likely that CD83 undergoes extensive post-translational processing because CD83 is expressed as a single chain molecule, but the determined molecular weight is twice the predicted size of the core protein. See U.S. Pat. No. 5,766,570.

An example of a human CD83 gene product that can be used in the invention is provided below (SEQ ID NO:9):

```
  1 MSRGLQLLLL SCAYSLAPAT PEVKVACSED VDLPCTAPWD
 41 PQVPYTVSWV KLLEGGEERM ETPQEDHLRG QHYHQKGQNG
 81 SFDAPNERPY SLKIRNTTSC NSGTYRCTLQ DPDGQRNLSG
121 KVILRVTGCP AQRKEETFKK YRAEIVLLLA LVIFYLTLII
161 FTCKFARLQS IFPDFSKAGM ERAFLPVTSP NKHLGLVTPH
201 KTELV
```

Such a CD83 gene product can be encoded by a number of different nucleic acids. One example of a human CD83 nucleic acid is provided below (SEQ ID NO:10).

```
   1 CCTGGCGCAG CCGCAGCAGC GACGCGAGCG AACTCGGCCG
  41 GGCCCGGGCG CGCGGGGGCG GGACGCGCAC GCGGCGAGGG
  81 CGGCGGGTGA GCCGGGGGCG GGGACGGGGG CGGGACGGGG
 121 GCGAAGGGGG CGGGGACGGG GGCGCCCGCC GGCCTAACGG
 161 GATTAGGAGG GCGCGCCACC CGCTTCCGCT GCCCGCCGGG
 201 GAATCCCCCG GGTGGCGCCC AGGGAAGTTC CCGAACGGGC
 241 GGGCATAAAA GGGCAGCCGC GCCGGCGCCC CACAGCTCTG
 281 CAGCTCGTGG CAGCGGCGCA GCGCTCCAGC CATGTCGCGC
 321 GGCCTCCAGC TTCTGCTCCT GAGCTGCGCC TACAGCCTGG
 361 CTCCCGCGAC GCCGGAGGTG AAGGTGGCTT GCTCCGAAGA
 401 TGTGGACTTG CCCTGCACCG CCCCCTGGGA TCCGCAGGTT
 441 CCCTACACGG TCTCCTGGGT CAAGTTATTG GAGGGTGGTG
 481 AAGAGAGGAT GGAGACACCC CAGGAAGACC ACCTCAGGGG
 521 ACAGCACTAT CATCAGAAGG GGCAAAATGG TTCTTTCGAC
 561 GCCCCCAATG AAAGGCCCTA TTCCCTGAAG ATCCGAAACA
 601 CTACCAGCTG CAACTCGGGG ACATACAGGT GCACTCTGCA
 641 GGACCCGGAT GGGCAGAGAA ACCTAAGTGG CAAGGTGATC
 681 TTGAGAGTGA CAGGATGCCC TGCACAGCGT AAAGAAGAGA
 721 CTTTTAAGAA ATACAGAGCG GAGATTGTCC TGCTGCTGGC
 761 TCTGGTTATT TTCTACTTAA CACTCATCAT TTTCACTTGT
 801 AAGTTTGCAC GGCTACAGAG TATCTTCCCA GATTTTTCTA
 841 AAGCTGGCAT GGAACGAGCT TTTCTCCCAG TTACCTCCCC
 881 AAATAAGCAT TTAGGGCTAG TGACTCCTCA CAAGACAGAA
 921 CTGGTATGAG CAGGATTTCT GCAGGTTCTT CTTCCTGAAG
 961 CTGAGGCTCA GGGGTGTGCC TGTCTGTTAC ACTGGAGGAG
1001 AGAAGAATGA GCCTACGCTG AAGATGGCAT CCTGTGAAGT
1041 CCTTCACCTC ACTGAAAACA TCTGGAAGGG GATCCCACCC
1081 CATTTTCTGT GGGCAGGCCT CGAAAACCAT CACATGACCA
1121 CATAGCATGA GGCCACTGCT GCTTCTCCAT GGCCACCTTT
1161 TCAGCGATGT ATGCAGCTAT CTGGTCAACC TCCTGGACAT
1201 TTTTTCAGTC ATATAAAAGC TATGGTGAGA TGCAGCTGGA
```

```
1241 AAAGGGTCTT GGGAAATATG AATGCCCCCA GCTGGCCCGT
1281 GACAGACTCC TGAGGACAGC TGTCCTCTTC TGCATCTTGG
1321 GGACATCTCT TTGAATTTTC TGTGTTTTGC TGTACCAGCC
1361 CAGATGTTTT ACGTCTGGGA GAAATTGACA GATCAAGCTG
1401 TGAGACAGTG GGAAATATTT AGCAAATAAT TTCCTGGTGT
1441 GAAGGTCCTG CTATTACTAA GGAGTAATCT GTGTACAAAG
1481 AAATAACAAG TCGATGAACT ATTCCCCAGC AGGGTCTTTT
1521 CATCTGGGAA AGACATCCAT AAAGAAGCAA TAAAGAAGAG
1561 TGCCACATTT ATTTTTATAT CTATATGTAC TTGTCAAAGA
1601 AGGTTTGTGT TTTTCTGCTT TTGAAATCTG TATCTGTAGT
1641 GAGATAGCAT TGTGAACTGA CAGGCAGCCT GGACATAGAG
1681 AGGGAGAAGA AGTCAGAGAG GGTGACAAGA TAGAGAGCTA
1721 TTTAATGGCC GGCTGGAAAT GCTGGGCTGA CGGTGCAGTC
1761 TGGGTGCTCG CCCACTTGTC CCACTATCTG GGTGCATGAT
1801 CTTGAGCAAG TTCCTTCTGG TGTCTGCTTT CTCCATTGTA
1841 AACCACAAGG CTGTTGCATG GGCTAATGAA GATCATATAC
1881 GTGAAAATTA TTTGAAAACA TATAAAGCAC TATACAGATT
1921 CGAAACTCCA TTGAGTCATT ATCCTTGCTA TGATGATGGT
1961 GTTTTGGGGA TGAGAGGGTG CTATCCATTT CTCATGTTTT
2001 CCATTGTTTG AAACAAAGAA GGTTACCAAG AAGCCTTTCC
2041 TGTAGCCTTC TGTAGGAATT CTTTTGGGGA AGTGAGGAAG
2081 CCAGGTCCAC GGTCTGTTCT TGAAGCAGTA GCCTAACACA
2121 CTCCAAGATA TGGACACACG GGAGCCGCTG GCAGAAGGGA
2161 CTTCACGAAG TGTTGCATGG ATGTTTTAGC CATTGTTGGC
2201 TTTCCCTTAT CAAACTTGGG CCCTTCCCTT CTTGGTTTCC
2241 AAAGGCATTT ATTGCTGAGT TATATGTTCA CTGTCCCCCT
2281 AATATTAGGG AGTAAAACGG ATACCAAGTT GATTTAGTGT
2321 TTTTACCTCT GTCTTGGCTT TCATGTTATT AAACGTATGC
2361 ATGTGAAGAA GGGTGTTTTT CTGTTTTATA TTCAACTCAT
2401 AAGACTTTGG GATAGGAAAA ATGAGTAATG GTTACTAGGC
2441 TTAATACCTG GGTGATTACA TAATCTGTAC AACGAACCCC
2481 CATGATGTAA GTTACCTAT GTAACAAACC TGCACTTATA
2521 CCCATGAACT TAAAATGAAA GTTAAAAATA AAAACATAT
2561 ACAAATAAAA AAAA
```

A sequence of a wild type mouse CD83 gene that can be used in the invention is provided herein as SEQ ID NO:1. SEQ ID NO:1 is provided below with the ATG start codon and the TGA stop codon identified by underlining.

```
   1 GCGCTCCAGC CGCATGTCGC AAGGCCTCCA GCTCCTGTTT
  41 CTAGGCTGCG CCTGCAGCCT GGCACCCGCG ATGGCGATGC
  81 GGGAGGTGAC GGTGGCTTGC TCCGAGACCG CCGACTTGCC
 121 TTGCACAGCG CCCTGGGACC CGCAGCTCTC CTATGCAGTG
 161 TCCTGGGCCA AGGTCTCCGA GAGTGGCACT GAGAGTGTGG
 201 AGCTCCCGGA GAGCAAGCAA AACAGCTCCT TCGAGGCCCC
 241 CAGGAGAAGG GCCTATTCCC TGACGATCCA AAACACTACC
 281 ATCTGCAGCT CGGGCACCTA CAGGTGTGCC CTGCAGGAGC
 321 TCGGAGGGCA GCGCAACTTG AGCGGCACCG TGGTTCTGAA
 361 GGTGACAGGA TGCCCCAAGG AAGCTACAGA GTCAACTTTC
 401 AGGAAGTACA GGGCAGAAGC TGTGTTGCTC TTCTCTCTGG
 441 TTGTTTTCTA CCTGACACTC ATCATTTTCA CCTGCAAATT
 481 TGCACGACTA CAAAGCATTT CCCAGATAT TTCTAAACCT
 521 GGTACGAAC AAGCTTTTCT TCCAGTCACC TCCCCAAGCA
 561 AACATTTGGG GCCAGTGACC CTTCCTAAGA CAGAAACGGT
 601 ATGAGTAGGA TCTCCACTGG TTTTTACAAA GCCAAGGGCA
 641 CATCAGATCA GTGTGCCTGA ATGCCACCCG GACAAGAGAA
 681 GAATGAGCTC CATCCTCAGA TGGCAACCTT TCTTTGAAGT
 721 CCTTCACCTG ACAGTGGGCT CCACACTACT CCCTGACACA
 761 GGGTCTTGAG CACCATCATA TGATCACGAA GCATGGAGTA
 801 TCACCGCTTC TCTGTGGCTG TCAGCTTAAT GTTTCATGTG
 841 GCTATCTGGT CAACCTCGTG AGTGCTTTTC AGTCATCTAC
 881 AAGCTATGGT GAGATGCAGG TGAAGCAGGG TCATGGGAAA
 921 TTTGAACACT CTGAGCTGGC CCTGTGACAG ACTCCTGAGG
 961 ACAGCTGTCC TCTCCTACAT CTGGGATACA TCTCTTTGAA
1001 TTTGTCCTGT TTCGTTGCAC CAGCCCAGAT GTCTCACATC
1041 TGGCGGAAAT TGACAGGCCA AGCTGTGAGC CAGTGGGAAA
1081 TATTTAGCAA ATAATTTCCC AGTGCGAAGG TCCTGCTATT
1121 AGTAAGGAGT ATTATGTGTA CATAGAAATG AGAGGTCAGT
1161 GAACTATTCC CCAGCAGGGC CTTTTCATCT GGAAAAGACA
1201 TCCACAAAAG CAGCAATACA GAGGGATGCC ACATTTATTT
1241 TTTTAATCTT CATGTACTTG TCAAAGAAGA ATTTTTCATG
1281 TTTTTTCAAA GAAGTGTGTT TCTTTCCTTT TTTAAAATAT
1321 GAAGGTCTAG TTACATAGCA TTGCTAGCTG ACAAGCAGCC
1361 TGAGAGAAGA TGGAGAATGT TCCTCAAAAT AGGGACAGCA
1401 AGCTAGAAGC ACTGTACAGT GCCCTGCTGG GAAGGGCAGA
1441 CAATGGACTG AGAAACCAGA AGTCGGCCA CAAGATTGTC
1481 TGTATGATTC TGGACGAGTC ACTTGTGGTT TTCACTCTCT
1521 GGTTAGTAAA CCAGATAGTT TAGTCTGGGT TGAATACAAT
1561 GGATGTGAAG TTGCTTGGGG AAAGCTGAAT GTAGTGAATA
1601 CATTGGCAAC TCTACTGGGC TGTTACCTTG TTGATATCCT
1641 AGAGTTCTGG AGCTGAGCGA ATGCCTGTCA TATCTCAGCT
```

```
1681 TGCCCATCAA TCCAAACACA GGAGGCTACA AAAAGGACAT
1721 GAGCATGGTC TTCTGTGTGA ACTCCTCCTG AGAAACGTGG
1761 AGACTGGCTC AGCGCTTTGC GCTTGAAGGA CTAATCACAA
1801 GTTCTTGAAG ATATGGACCT AGGGGAGCTA TTGCGCCACG
1841 ACAGGAGGAA GTTCTCAGAT GTTGCATTGA TGTAACATTG
1881 TTGCATTTCT TTAATGAGCT GGGCTCCTTC CTCATTTGCT
1921 TCCCAAAGAG ATTTTGTCCC ACTAATGGTG TGCCCATCAC
1961 CCACACTATG AAAGTAAAAG GGATGCTGAG CAGATACAGC
2001 GTGCTTACCT CTCAGCCATG ACTTTCATGC TATTAAAAGA
2041 ATGCATGTGA A
```

Nucleic acids having SEQ ID NO:1 encode a mouse polypeptide having SEQ ID NO:2, provided below.

```
  1 MSQGLQLLFL GCACSLAPAM ANREVTVACS ETADLPCTAP
 41 WDPQLSYAVS WAKVSESGTE SVELPESKQN SSFEAPRRRA
 81 YSLTIQNTTI CSSGTYRCAL QELGGQRNLS GTVVLKVTGC
121 PKEATESTFR KYRAEAVLLF SLVVFYLTLI IFTCKFARLQ
161 SIFPDISKPG TEQAFLPVTS PSKHLGPVTL PKTETV
```

According to the invention, loss or reduction of CD83 activity in vivo results in altered cytokine levels, for example, lower interleukin-2 levels, increased interleukin-4 levels, increased GM-CSF levels and increased interleukin-10 levels. Loss or reduction of CD83 activity in vivo can also result in decreased numbers of T cells.

Moreover, increased CD83 activity in vivo can also result in altered cytokine levels, for example, higher interleukin-2 levels, decreased interleukin-4 levels, decreased GM-CSF levels and decreased interleukin-10 levels. Increased CD83 expression or activity in vivo can also result in increased activation or increased numbers of T cells.

The effect of CD83 on cytokine levels was ascertained through use of a mutant mouse that encodes a mutant CD83. Such a mutant mouse has a CD83 gene encoding SEQ ID NO:4, with added C-terminal sequences provided by SEQ ID NO:8. In contrast to these wild type CD83 nucleic acids and polypeptides, the mutant CD83 gene of the invention has SEQ ID NO:3. SEQ ID NO:3 is provided below with the ATG start codon, the mutation, and the TGA stop codon are identified by underlining.

```
  1 GCGCTCCAGC CGC<u>ATG</u>TCGC AAGGCCTCCA GCTCCTGTTT
 41 CTAGGCTGCG CCTGCAGCCT GGCACCCGCG ATGGCGATGC
 81 GGGAGGTGAC GGTGGCTTGC TCCGAGACCG CCGACTTGCC
121 TTGCACAGCG CCCTGGGACC CGCAGCTCTC CTATGCAGTG
161 TCCTGGGCCA AGGTCTCCGA GAGTGGCACT GAGAGTGTGG
201 AGCTCCCGGA GAGCAAGCAA AACAGCTCCT TCGAGGCCCC
241 CAGGAGAAGG GCCTATTCCC TGACGATCCA AAACACTACC
281 ATCTGCAGCT CGGGCACCTA CAGGTGTGCC CTGCAGGAGC
321 TCGGAGGGCA GCGCAACTTG AGCGGCACCG TGGTTCTGAA
361 GGTGACAGGA TGCCCCAAGG AAGCTACAGA GTCAACTTTC
401 AGGAAGTACA GGGCAGAAGC TGTGTTGCTC TTCTCTCTGG
441 TTGTTTTCTA CCTGACACTC ATCATTTTCA CCTGCAAATT
481 TGCACGACTA CAAAGCATTT TCCCAGATAT TTCTAAACCT
521 GGTACGGAAC AAGCTTTTCT TCCAGTCACC TCCCCAAGCA
561 AACATTTGGG GCCAGTGACC CTTCCTAAGA CAGAAACGGT
601 A<u>A</u>GAGTAGGA TCTCCACTGG TTTTTACAAA GCCAAGGGCA
641 CATCAGATCA GTGTGCCTGA ATGCCACCCG GACAAGAGAA
681 GAATGAGCTC CATCCTCAGA TGGCAACCTT TCTTTGAAGT
721 CCTTCACCTG ACAGTGGGCT CCACACTACT CCCTGACACA
761 GGGTCT<u>TGA</u>G CACCATCATA TGATCACGAA GCATGGAGTA
801 TCACCGCTTC TCTGTGGCTG TCAGCTTAAT GTTTCATGTG
841 GCTATCTGGT CAACCTCGTG AGTGCTTTTC AGTCATCTAC
881 AAGCTATGGT GAGATGCAGG TGAAGCAGGG TCATGGGAAA
921 TTTGAACACT CTGAGCTGGC CCTGTGACAG ACTCCTGAGG
961 ACAGCTGTCC TCTCCTACAT CTGGGATACA TCTCTTTGAA
1001 TTTGTCCTGT TTCGTTGCAC CAGCCCAGAT GTCTCACATC
1041 TGGCGGAAAT TGACAGGCCA AGCTGTGAGC CAGTGGGAAA
1081 TATTTAGCAA ATAATTTCCC AGTGCGAAGG TCCTGCTATT
1121 AGTAAGGAGT ATTATGTGTA CATAGAAATG AGAGGTCAGT
1161 GAACTATTCC CCAGCAGGGC CTTTTCATCT GGAAAAGACA
1201 TCCACAAAAG CAGCAATACA GAGGGATGCC ACATTTATTT
1241 TTTTAATCTT CATGTACTTG TCAAAGAAGA ATTTTTCATG
1281 TTTTTTCAAA GAAGTGTGTT TCTTTCCTTT TTTAAAATAT
1321 GAAGGTCTAG TTACATAGCA TTGCTAGCTG ACAAGCAGCC
1361 TGAGAGAAGA TGGAGAATGT TCCTCAAAAT AGGGACAGCA
1401 AGCTAGAAGC ACTGTACAGT GCCCTGCTGG GAAGGGCAGA
1441 CAATGGACTG AGAAACCAGA AGTCTGGCCA CAAGATTGTC
1481 TGTATGATTC TGGACGAGTC ACTTGTGGTT TTCACTCTCT
1521 GGTTAGTAAA CCAGATAGTT TAGTCTGGGT TGAATACAAT
1561 GGATGTGAAG TTGCTTGGGG AAAGCTGAAT GTAGTGAATA
1601 CATTGGCAAC TCTACTGGGC TGTTACCTTG TTGATATCCT
1641 AGAGTTCTGG AGCTGAGCGA ATGCCTGTCA TATCTCAGCT
1681 TGCCCATCAA TCCAAACACA GGAGGCTACA AAAGGACAT
1721 GAGCATGGTC TTCTGTGTGA ACTCCTCCTG AGAAACGTGG
1761 AGACTGGCTC AGCGCTTTGC GCTTGAAGGA CTAATCACAA
1801 GTTCTTGAAG ATATGGACCT AGGGGAGCTA TTGCGCCACG
1841 ACAGGAGGAA GTTCTCAGAT GTTGCATTGA TGTAACATTG
1881 TTGCATTTCT TTAATGAGCT GGGCTCCTTC CTCATTTGCT
```

-continued

```
1921 TCCCAAAGAG ATTTTGTCCC ACTAATGGTG TGCCCATCAC

1961 CCACACTATG AAAGTAAAAG GGATGCTGAG CAGATACAGC

2001 GTGCTTACCT CTCAGCCATG ACTTTCATGC TATTAAAAGA

2041 ATGCATGTGA A
```

The change from a thymidine in SEQ ID NO:1 to an adenine in SEQ ID NO:3 at the indicated position (602) leads to read-through translation because the stop codon at positions 602-604 in SEQ ID NO:1 is changed to a codon that encodes an arginine. Accordingly, mutant CD83 nucleic acids having SEQ ID NO:3 encode an elongated polypeptide having SEQ ID NO:4, provided below, where the extra amino acids are underlined.

```
  1 MSQGLQLLFL GCACSLAPAN AMREVTVACS ETADLPCTAP

41 WDPQLSYAVS WAKVSESGTE SVELPESKQN SSFEAPRRRA

81 YSLTIQNTTI CSSGTYRCAL QELGGQRNLS GTVVLKVTGC

121 PKEATESTFR KYRAEAVLLF SLVVFYLTLI IFTCKFARLQ

161 SIFPDISKPG TEQAFLPVTS PSKHLGPVTL PKTETVRVGS

201 PLVFTKPRAH QISVPECHPD KRRMSSILRW QPFFEVLHLT

241 VGSTLLPDTG S
```

In another embodiment, the invention provides mutant CD83 nucleic acids that include SEQ ID NO:5.

```
  1 ATGTCGCAAG GCCTCCAGCT CCTGTTTCTA GGCTGCGCCT

41 GCAGCCTGGC ACCCGCGATG GCGATGCGGG AGGTGACGGT

81 GGCTTGCTCC GAGACCGCCG ACTTGCCTTG CACAGCGCCC

121 TGGGACCCGC AGCTCTCCTA TGCAGTGTCC TGGGCCAAGG

161 TCTCCGAGAG TGGCACTGAG AGTGTGGAGC TCCCGGAGAG

201 CAAGCAAAAC AGCTCCTTCG AGGCCCCCAG GAGAAGGGCC

241 TATTCCCTGA CGATCCAAAA CACTACCATC TGCAGCTCGG

281 GCACCTACAG GTGTGCCCTG CAGGAGCTCG GAGGGCAGCG

321 CAACTTGAGC GGCACCGTGG TTCTGAAGGT GACAGGATGC

361 CCCAAGGAAG CTACAGAGTC AACTTTCAGG AAGTACAGGG

401 CAGAAGCTGT GTTGCTCTTC TCTCTGGTTG TTTTCTACCT

441 GACACTCATC ATTTTCACCT GCAAATTTGC ACGACTACAA

481 AGCATTTTCC CAGATATTTC TAAACCTGGT ACGGAACAAG

521 CTTTTCTTCC AGTCACCTCC CCAAGCAAAC ATTTGGGGCC

561 AGTGACCCTT CCTAAGACAG AAACGGTAAG AGTAGGATCT

601 CCACTGGTTT TTACAAAGCC AAGGGCACAT CAGATCAGTG

641 TGCCTGAATG CCACCCGGAC AAGAGAAGAA TGAGCTCCAT

681 CCTCAGATGG CAACCTTTCT TTGAAGTCCT TCACCTGACA

721 GTGGGCTCCA CACTACTCCC TGACACAGGG TCTTGA
```

Nucleic acids having SEQ ID NO:5 also encode a polypeptide having SEQ ID NO:4.

In another embodiment, the invention provides mutant CD83 nucleic acids that include SEQ ID NO:7.

```
  1 AGAGTAGGAT CTCCACTGGT TTTTACAAAG CCAAGGGCAC

41 ATCAGATCAG TGTGCCTGAA TGCCACCCGG ACAAGAGAAG

81 AATGAGCTCC ATCCTCAGAT GGCAACCTTT CTTTGAAGTC

121 CTTCACCTGA CAGTGGGCTC CACACTACTC CCTGACACAG

161 GGTCTTGA
```

The invention also provides a mutant CD83 containing SEQ ID NO:8, provided below.

```
  1 RVGSPLVFTK PRABQISVPE CHPDKRRMSS ILRWQPFFEV

41 LHLTVGSTLL PDTGS
```

SEQ ID NO:8 contains read through sequences that are not present in the wild type CD83 polypeptide but are present in the mutant CD83 gene product provided by the invention.

CD83 Modulation of Cytokine Levels

The invention also provides compositions and methods for increasing interleukin-4 levels, increasing GM-CSF levels, increasing interleukin-10 levels and decreasing interleukin-2 levels in a mammal. Such compositions and methods generally operate by decreasing the expression or function of CD83 gene products in the mammal. Interleukin-4 promotes the differentiation of Th2 cells while decreasing the differentiation of precursor cells into Th1 cells. Th2 cells are involved in helping B lymphocytes and in stimulating production of IgG1 and IgE antibodies. Enhancement of Th2 formation may be useful, for example, in autoimmune diseases and in organ transplantation.

Alternatively, the invention provides compositions and methods for decreasing interleukin-4 levels, decreasing interleukin-10 levels and increasing interleukin-2 levels in a mammal. Such compositions and methods generally increase the expression or function of CD83 gene products in the mammal. Interleukin-2 promotes the differentiation of Th1 cells and decreases the differentiation of Th-2 cells. Th1 cells are, for example, involved in inducing autoimmune and delayed type hypersensitivity responses. Inhibition of Th2 formation may be useful in treating allergic diseases, malignancies and infectious diseases.

CD4+T helper cells are not a homogeneous population but can be divided on the basis of cytokine secretion into at least two subsets termed T helper type 1 (Th1) and T helper type 2 (Th2) (see e.g., Mosmann, T. R. et al. (1986) J. Immunol. 136:2348-2357; Paul, W. E. and Seder, R. A. (1994) Cell 76:241-251; Seder, R. A. and Paul, W. E. (1994) Ann. Rev. Immunol. 12:635-673). Th1 cells secrete interleukin-2 (IL-2) and interferon-γ (IFN-γ) while Th2 cells produce interleukin-4 (IL-4), interleukin-5 (IL-5), interleukin-10 (L-10) and interleukin-13 (IL-13). Both subsets produce cytokines such as tumor necrosis factor (TNF) and granulocyte/macrophage-colony stimulating factor (GM-CSF).

In addition to their different pattern of cytokine expression, Th1 and Th2 cells are thought to have differing functional activities. For example, Th1 cells are involved in inducing delayed type hypersensitivity responses, whereas Th2 cells are involved in providing efficient "help" to B lymphocytes and stimulating production of IgG1 and IgE antibodies.

The ratio of Th1 to Th2 cells is highly relevant to the outcome of a wide array of immunologically-mediated clinical diseases including autoimmune, allergic and infectious diseases. For example, in experimental leishmania infections in mice, animals that are resistant to infection mount predominantly a Th1 response, whereas animals that are susceptible to progressive infection mount predominantly a Th2 response (Heinzel, F. P., et al. (1989) J. Exp. Med. 169:59-72; Locksley, R. M. and Scott, P. (1992) Immunoparasitology Today 1:A58-A61). In murine schistosomiasis, a Th1 to Th2 switch is observed coincident with the release of eggs into the tissues by female parasites and is associated with a worsening of the disease condition (Pearce, E. J., et al. (1991) J. Exp. Med. 173:159-166; Grzych, J-M., et al. (1991) J. Immunol 141:1322-1327; Kullberg, M. C., et al. (1992) J. Immunol. 148:3264-3270).

Many human diseases, including chronic infections (such as with human immunodeficiency virus (HIV) and tuberculosis) and certain metastatic carcinomas, also are characterized by a Th1 to Th2 switch (see e.g., Shearer, G. M. and Clerici, M. (1992) Prog. Chem. Immunol. 54:21-43; Clerici, M and Shearer, G. M. (1993) Immunology Today 14:107-111; Yamamura, M., et al. (1993) J Clin. Invest. 91:1005-1010; Pisa, P., et al. (1992) Proc. Natl. Acad. Sci. USA 89:7708-7712; Fauci, A. S. (1988) Science 239:617-623).

Certain autoimmune diseases have been shown to be associated with a predominant Th1 response. For example, patients with rheumatoid arthritis have predominantly Th1 cells in synovial tissue (Simon, A. K., et al. (1994) Proc. Natl. Acad. Sci. USA 91:8562-8566) and experimental autoimmune encephalomyelitis (EAE) can be induced by autoreactive Th1 cells (Kuchroo, V. K., et al. (1993) J. Immunol. 151:4371-4381).

The ability to alter or manipulate ratios of Th1 and Th2 subsets requires an understanding of the mechanisms by which the differentiation of CD4 T helper precursor cells (Thp), which secrete only IL-2, choose to become Th1 or Th2 effector cells. It is clear that the cytokines themselves are potent Th cell inducers and form an autoregulatory loop (see e.g., Paul, W. E. and Seder, R. A. (1994) Cell 76:241-251; Seder, R. A. and Paul, W. E. (1994) Ann. Rev. Immunol. 12:635-673). Thus, IL4 promotes the differentiation of Th2 cells while preventing the differentiation of precursors into Th1 cells, while IL-12 and IFN-γ have the opposite effect.

According to the invention, one way to alter Th1:Th2 ratios is to increase or decrease the level of selected cytokines by using CD83. Direct administration of cytokines or antibodies to cytokines has been shown to have an effect on certain diseases mediated by either Th1 or Th2 cells. For example, administration of recombinant IL-4 or antibodies to IL-12 ameliorate EAE, a Th1-driven autoimmune disease (see Racke; M. K. et al. (1994) J. Exp. Med. 180:1961-1966; and Leonard, J. P. et al. (1995) J. Exp. Med. 181:381-386), while anti-IL-4 antibodies can ameliorate the Th2-mediated parasitic disease, *Leishmania major* (Sadick, M. D. et al. (1990) J. Exp. Med. 171:115-127).

Numerous disease conditions are associated with either a predominant Th1-type response or a predominant Th2-type response and the individuals suffering from such disease conditions could benefit from treatment with the CD83 related compositions and methods of the invention. Application of the immunomodulatory methods of the invention to such diseases is described in further detail below.

Allergies

Allergies are mediated through IgE antibodies whose production is regulated by the activity of Th2 cells and the cytokines produced thereby. In allergic reactions, IL-4 is produced by Th2 cells, which further stimulates production of IgE antibodies and activation of cells that mediate allergic reactions, i.e., mast cells and basophils. IL-4 also plays an important role in eosinophil mediated inflammatory reactions.

Accordingly, the stimulation of CD83 production by use of the compositions and methods of the invention can be used to inhibit the production of Th2-associated cytokines, for example IL-4, in allergic patients as a means to down-regulate production of pathogenic IgE antibodies. A stimulatory agent may be directly administered to the subject mammal. Alternatively, the CD83 stimulatory agent (e.g. CD83 expression cassette) can be administered to cells (e.g., Thp cells or Th2 cells) that may be obtained from the subject and those modified cells can be readministered to the subject mammal. Moreover, in certain situations it may be beneficial to co-administer the allergen together with the stimulatory agent either to the subject or to cells treated with the stimulatory agent Such co-administration can inhibit (e.g., desensitize) the allergen-specific response. The treatment may be further enhanced by administering Th1-promoting agents, such as the cytokine IL-12 or antibodies to Th2-associated cytokines (e.g., anti-IL-4 antibodies), to the allergic subject in amounts sufficient to further stimulate a Th1-type response.

Cancer

The invention also relates to CD83-related methods for increasing interleukin-10 (IL-10) levels to reduce the spread of neoplastic diseases and/or prevent neoplastic diseases and the growth of a tumor. According to the invention, decreased CD83 activity can dramatically increase the levels of IL-10 in the body and such increased interleukin-10 can be used to treat neoplastic diseases. Hence, the invention provides a method for preventing or treating tumors in a mammal, which involves diminishing CD83 expression or activity in the mammal. In various embodiments, the tumor is IL-2-dependent, a plasmacytoma, or a leukemia, including a lymphocytic leukemia such as a B cell lymphocytic leukemia.

The invention also provides methods for increasing T cell activation or T cell proliferation by increasing CD83 activity or expression. Such methods can also be used to prevent or treat tumors in a mammal.

Infectious Diseases

The expression of Th2-promoting cytokines also has been reported to increase during a variety of infectious diseases. For example, HIV infection, tuberculosis, leishmaniasis, schistosomiasis, filarial nematode infection, intestinal nematode infection and other such infectious diseases are associated with a Th1 to Th2 shift in the immune response. See e.g., Shearer, G. M. and Clerici, M. (1992) Prog. Chem. Immunol. 54:2143; Clerici, M and Shearer, G. M. (1993) Immunology Today 14:107-111; Fauci, A. S. (1988) Science 239:617-623; Locksley, R. M. and Scott, P. (1992) Immunoparasitology Today 1:A58-A61; Pearce, E. J., et al. (1991) J. Exp. Med. 173:159-166; Grzych, J-M., et al. (1991) J. Immunol. 141: 1322-1327; Kullberg, M. C., et al. (1992) J. Immunol. 148: 3264-3270; Bancroft, A. J., et al. (1993) J. Immunol 150: 1395-1402; Pearlman, E., et al. (11993) Infect. Immun. 61:1105-1112; Else, K. J., et al. (1994) J. Exp. Med. 179:347-351.

Accordingly, the stimulatory CD83-related compositions and methods of the invention can be used to inhibit the production of Th2-cells in subjects with infectious diseases to promote an ongoing Th1 response in the patients and to ameliorate the course of the infection. The treatment may be further enhanced by administering other Th1-promoting agents, such as the cytokine IL-12 or antibodies to Th2- associated cytokines (e.g., anti-IL-4 antibodies), to the recipient in amounts sufficient to further stimulate a Th 1-type response.

Hence, for example, infections of the following microbial organisms can be treated by the methods of the invention: *Aeromonas* spp., *Bacillus* spp., *Bacteroides* spp., *Campylobacter* spp., *Clostridium* spp., *Enterobacter* spp., *Enterococcus* spp., *Escherichia* spp., *Gastrospirillum* sp., *Helicobacter* spp., *Klebsiella* spp., *Salmonella* spp., *Shigella* spp., *Staphylococcus* spp., *Pseudomonas* spp., *Vibrio* spp., *Yersinia* spp., and the like. Infections that can be treated by the methods of the invention include those associated with staph infections (*Staphylococcus aureus*), typhus (*Salmonella typhi*), food poisoning (*Escherichia coli*, such as O157:H7), bascillary dysentery (*Shigella dysenteria*), pneumonia (*Psuedomonas aerugenosa* and/or *Pseudomonas cepacia*), cholera (*Vivrio cholerae*), ulcers (*Helicobacter pylori*) and others. *E. coli* serotype 0157:H7 has been implicated in the pathogenesis of diarrhea, hemorrhagic colitis, hemolytic uremic syndrome (HUS) and thrombotic thrombocytopenic purpura (TTP). The methods of the invention are also active against drug-resistant and multiply-drug resistant strains of bacteria, for example, multiply-resistant strains of *Staphylococcus aureus* and vancomycin-resistant strains of *Enterococcus faecium* and *Enterococcus faecalis*.

The methods of the invention are also effective against viruses. The term "virus" refers to DNA and RNA viruses, viroids, and prions. Viruses include both enveloped and non-enveloped viruses, for example, hepatitis A virus, hepatitis B virus, hepatitis C virus, human immunodeficiency virus (HIV), poxviruses, herpes viruses, adenoviruses, papovaviruses, parvoviruses, reoviruses, orbiviruses, picornaviruses, rotaviruses, alphaviruses, rubivirues, influenza virus type A and B, flaviviruses, coronaviruses, paramyxoviruses, morbilliviruses, pneumoviruses, rhabdoviruses, lyssaviruses, orthmyxoviruses, bunyaviruses, phleboviruses, nairoviruses, hepadnaviruses, arenaviruses, retroviruses, enteroviruses, rhinoviruses and the filovirus.

Autoimmune Diseases

The CD83-related compositions and methods of the invention can be used in the treatment of autoimmune diseases that are associated with a Th2-type dysfunction. Many autoimmune disorders are the result of inappropriate activation of T cells that are reactive against "self tissues" and that promote the production of cytokines and autoantibodies involved in the pathology of the diseases. Modulation of T helper-type responses can have an effect on the course of the autoimmune disease. For example, in experimental allergic encephalomyelitis, stimulation of a Th2-type response by administration of IL-4 at the time of the induction of the disease diminishes the intensity of the autoimmune disease (Paul, W. E., et al. (1994) Cell 76:241-251). Furthermore, recovery of the animals from the disease has been shown to be associated with an increase in a Th2-type response as evidenced by an increase of Th2-specific cytokines (Koury, S. J., et al. (1992) J. Exp. Med. 176:1355-1364). Moreover, T cells that can suppress EAE secrete Th2-specific cytokines (Chen, C., et al. (1994) Immunity 1:147-154). Since stimulation of a Th2-type response in experimental allergic encephalomyelitis has a protective effect against the disease, stimulation of a Th2 response in subjects with multiple sclerosis (for which EAE is a model) is likely to be beneficial therapeutically.

Similarly, stimulation of a Th2-type response in type I diabetes in mice provides a protective effect against the disease. Indeed, treatment of NOD mice with IL-4 (which promotes a Th2 response) prevents or delays onset of type I diabetes that normally develops in these mice (Rapoport, M. J., et al. (1993) J. Exp. Med. 178:87-99). Thus, inhibition of CD83 production can stimulate IL-4 production and/or a Th2 response in a subject suffering from or susceptible to diabetes may ameliorate the effects of the disease or inhibit the onset of the disease.

Yet another autoimmune disease in which stimulation of a Th2-type response may be beneficial is rheumatoid arthritis (RA). Studies have shown that patients with rheumatoid arthritis have predominantly Th1 cells in synovial tissue (Simon, A. K., et al., (1994) Proc. Natl. Acad. Sci. USA 91:8562-8566). By stimulating a Th2 response in a subject with rheumatoid arthritis, the detrimental Th1 response can be concomitantly down-modulated to thereby ameliorate the effects of the disease.

Accordingly, the CD83-related compositions and methods of the invention can be used to stimulate production of Th2-associated cytokines in subjects suffering from, or susceptible to, an autoimmune disease in which a Th2-type response is beneficial to the course of the disease. Such compositions and methods would modulate CD83 activity. In some embodiments, the compositions would decrease CD83 activity and thereby increase the level of certain cytokines, for example, IL-4 levels are increased when CD83 activity is diminished. The treatment may be further enhanced by administering other Th2-promoting agents, such as IL-4 itself or antibodies to Th1-associated cytokines, to the subject in amounts sufficient to further stimulate a Th2-type response. The treatment may be further enhanced by administering a Th1-promoting cytokine (e.g., IFN-γ) to the subject in amounts sufficient to further stimulate a Th1-type response.

The efficacy of CD83-related for treating autoimmune diseases can be tested in the animal models provided herein or other models of human diseases (e.g., EAE as a model of multiple sclerosis and the NOD mice as a model for diabetes). Such animal models include the mrl/lpr/lpr mouse as a model for lupus erythematosus, murine collagen-induced arthritis as a model for rheumatoid arthritis, and murine experimental myasthenia gravis (see Paul ed., Fundamental Immunology, Raven Press, New York, 1989, pp. 840-856). A CD83-modulatory (i.e., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Non-limiting examples of autoimmune diseases and disorders having an autoimmune component that may be treated according to the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

Transplantation

While graft rejection or graft acceptance may not be attributable exclusively to the action of a particular T cell subset (i.e., Th1 or Th2 cells) in the graft recipient, studies have implicated a predominant Th2 response in prolonged graft survival and a predominant Th1 response in graft rejection (for a discussion see Dallman, M. J. (1995) Curr. Opin. Immunol. 7:632-638; Takeuchi, T. et al. (1992) Transplantation 53:1281-1291; Tzakis, A. G. et al. (1994) J. Pediatr. Surg. 29:754-756; Thai, N. L. et al. (1995) Transplantation 59:274-281. Additionally, adoptive transfer of cells having a Th2 cytokine phenotype prolongs skin graft survival (Maeda, H. et al. (1994) Int. Immunol. 6:855-862) and reduces graft-versus-host disease (Fowler, D. H. et al. (1994) Blood 84:3540-3549; Fowler, D. H. et al. (1994) Prog. Clin. Biol. Res. 389:533-540). Furthermore, administration of IL-4, which promotes Th2 differentiation, prolongs cardiac allograft survival (Levy, A. E. and Alexander, J. W. (1995) Transplantation 60:405-406), whereas administration of IL-12 in combination with anti-IL-10 antibodies, which promotes Th1 differentiation, enhances skin allograft rejection (Gorczynski, R. M. et al. (1995) Transplantation 60:1337-1341).

As provided herein, loss of CD83 function increases interleukin-4 production, which in turn promotes the differentiation of Th2 cells and depresses the differentiation of precursor cells into Th1 cells. Accordingly, methods of the invention that involve decreasing CD83 function can be used to stimulate production of Th2-associated cytokines in transplant recipients to prolong survival of the graft. These methods can be used both in solid organ transplantation and in bone marrow transplantation (e.g., to inhibit graft-versus-host disease). These methods can involve either direct administration of a CD83 inhibitory agent to the transplant recipient or ex vivo treatment of cells obtained from the subject (e.g., Thp, Th1 cells, B cells, non-lymphoid cells) with an inhibitory agent followed by readministration of the cells to the subject. The treatment may be further enhanced by administering other Th2-promoting agents, such as IL-4 itself or antibodies to Th1-associated cytokines, to the recipient in amounts sufficient to further stimulate a Th2-type response.

Additional Methods of Using CD83

In addition to the foregoing disease situations, the modulatory methods of the invention also are useful for other purposes.

For example, inhibition of CD83 activity or function gives rise to increased granulocyte macrophage-colony stimulating factor (GM-CSF). Granulocyte macrophage colony stimulating factor is a hematopoietic growth factor that promotes the proliferation and differentiation of hematopoietic progenitor cells. GM-CSF is approved for treatment of patients requiring increased proliferation of white blood cells. Data indicates that GM-CSP is also useful as a vaccine adjuvant Morrissey, et al., J. Immunology 139, 1113-1119 (1987). GM-CSF can also be used to treat patients prone to infection such as those undergoing high risk bowel surgery, trauma victims and individuals with HIV.

Accordingly, the invention provides a method of increasing the levels of GM-CSF in a mammal or in a mammalian cell by administering an agent that modulates or inhibits CD83 activity or expression.

The invention also provides a method of decreasing the levels of GM-CSF in a mammal or in a mammalian cell by administering an agent that modulates or stimulates CD83 activity or expression.

Moreover, in other embodiments the CD83 inhibitory methods of the invention can be used to stimulate production of IL-4 or IL-10 in vitro for commercial production of these cytokines. For example, CD4+ T cells with a null or other mutation in the CD83 gene can be cultured and then stimulated to produce cytokines, for example, by use of anti-CD3 and/or anti-CD28 antibodies to activate the mutant CD4+ T cells. Significant amounts of IL-4 and IL-10 can then be isolated from the culture media. Alternatively, CD4+ T cells can be contacted with the CD83 inhibitory agent in vitro to stimulate IL-4 or IL-10 production and the IL-4 or IL-10 can be recovered from the culture supernatant. The isolated IL-4 and/or IL-10 can be further purified if necessary, and packaged for commercial use.

The methods of the invention can be adapted to vaccinations to promote either a Th1 or a Th2 response to an antigen of interest in a subject. That is, CD83 or CD83 modulators of the invention can serve as adjuvants to direct an immune response to a vaccine either to a Th1 response or a Th2 response. For example, to stimulate an antibody response to an antigen of interest (i.e., for vaccination purposes), the antigen and a CD83 inhibitory agent of the invention can be coadministered to a subject to promote a Th2 response to the antigen in the subject, since Th2 responses provide efficient B cell help and promote IgG1 production.

Alternatively, to promote a cellular immune response to an antigen of interest, the antigen and a CD83 stimulating agent of the invention can be coadministered to a subject to promote a Th1 response to the antigen in a subject, since Th1 responses favor the development of cell-mediated immune responses (e.g., delayed hypersensitivity responses).

The antigen of interest and the modulatory agent can be formulated together into a single pharmaceutical composition or in separate compositions.

Thus, in some embodiments, the antigen of interest and the modulatory agent are administered simultaneously to the subject. Alternatively, in certain situations it may be desirable to administer the antigen first and then the modulatory agent or vice versa. For example, in the case of an antigen that naturally evokes a Th1 response, it may be beneficial to first administer the antigen alone to stimulate a Th1 response and then administer a CD83 inhibitory agent, alone or together with a boost of antigen, to shift the immune response to a Th2 response.

According to the invention, any agent that can modulate CD83 to increase or decrease cytokine levels, increase or decrease T cell levels or produce any other CD83-related response can be used in the compositions and methods of the invention. In some embodiments, anti-CD83 antibodies of the invention are used to either activate or inhibit CD83 activity. Activation or inhibition by such antibodies can depend on the epitope to which the antibody binds. Hence, antibodies may play a role in boosting or depressing CD83 activity. These CD83 modulatory agents, including anti-CD83 antibodies, are described in more detail below.

Stimulating or Inhibiting CD83

According to the invention, any agent that can stimulate CD83 to perform its natural functions can be used in the compositions and methods of the invention as a CD83 stimulatory agent. Indicators that CD83 activity is stimulated include increased IL-2 cytokine levels, increased T cell levels, and increased TNF levels relative to unstimulated levels in wild type CD83 cells. Examples of CD83 stimulatory agents include, for example, the CD83 gene product itself, certain anti-CD83 antibodies, CD83-encoding nucleic acids (DNA or RNA), factors that promote CD83 transcription or translation, organic molecules, peptides and the like.

Also, according to the invention, any agent that can inhibit CD83 from performing its natural functions can be used in the compositions and methods of the invention as a CD83 inhibitory agent. Indicators that CD83 activity is inhibited include increased IL-4 cytokine levels, increased IL-10 levels, decreased IL-2 production, decreased T cell levels, and decreased TNF levels relative to uninhibited levels in wild type CD83 cells.

Examples of CD83 inhibitors include anti-CD83 antibodies, CD83 anti-sense nucleic acids (e.g. nucleic acids that can hybridize to CD83 nucleic acids), organic compounds, peptides and agents that can mutate an endogenous CD83 gene. In some embodiments, the CD83 stimulatory or inhibitory agents are proteins, for example, CD83 gene products, anti-CD83 antibody preparations, CD83 inhibitors, peptides and protein factors that can promote CD83 transcription or translation. In other embodiments, the CD83 stimulatory or inhibitory agents are peptides or organic molecules. Such proteins, organic molecules and organic molecules can be prepared and/or purified as described herein or by methods available in the art, and administered as provided herein.

In other embodiments, the CD83 stimulatory or inhibitory agents can be nucleic acids including recombinant expression vectors or expression cassettes encoding CD83 gene products, CD83 transcription factors, CD83 anti-sense nucleic acid, intracellular antibodies capable of binding to CD83 or dominant negative CD83 inhibitors. Such nucleic acids can be operably linked to a promoter that is functional in a mammalian cell, and then introduced into cells of the subject mammal using methods known in the art for introducing nucleic acid (e.g., DNA) into cells.

The "promoter functional in a mammalian cell" or "mammalian promoter" is capable of directing transcription of a polypeptide coding sequence operably linked to the promoter. The promoter should generally be active in T cells and antigen presenting cells and may be obtained from a gene that is expressed in T cells or antigen presenting cells. However, it need not be a T cell-specific or an antigen presenting cell specific-promoter. Instead, the promoter may be selected from any mammalian or viral promoter that can function in a T cell. Hence the promoter may be an actin promoter, an immunoglobulin promoter, a heat-shock promoter, or a viral promoter obtained from the genome of viruses such as adenoviruses, retroviruses, lentiviruses, herpes viruses, including but not limited to, polyoma virus, fowlpox virus, adenovirus 2, bovine papilloma virus, avian sarcoma virus, cytomegalovirus (CMV), hepatitis-B virus, Simian Virus 40 (SV40), Epstein Barr virus (EBV), feline immunedeficiency virus (FIV), and Sr.alpha., or are respiratory synsitial viral promoters (RSV) or long terminal repeats (LTRs) of a retrovirus, i.e., a Moloney Murine Leukemia Virus (MoMuLv) (Cepko et al. (1984) Cell 37:1053-1062). The promoter functional in a mammalian cell can be inducible or constitutive.

Any cloning procedure used by one of skill in the art can be employed to make the expression vectors or expression that comprise a promoter operably linked to a CD83 nucleic acid, CD83 transcription factor or a nucleic acid encoding an anti-CD83 antibody. See, e.g., Sambrook et al., Molecular Cloning, A Laboratory Manual, Cold Spring Harbor Laboratory, N.Y., 1989; Sambrook et al., Molecular Cloning, A Laboratory Manual, Cold Spring Harbor Laboratory, N.Y., 2001.

After constructing an expression vector or an expression cassette encoding CD83 gene products, CD83 transcription factors, CD83 anti-sense nucleic acid, intracellular antibodies capable of binding to CD83 or dominant negative CD83 inhibitors, mammalian cells can be transformed with the vector or cassette. Examples of such methods include:

Direct Injection: Naked DNA can be introduced into cells in vivo by directly injecting the DNA into the cells (see e.g., Acsadi et al. (1991) Nature 332:815-818; Wolff et al. (1990) Science 247:1465-1468). For example, a delivery apparatus (e.g., a "gene gun") for injecting DNA into cells in vivo can be used. Such an apparatus is commercially available (e.g., from BioRad).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids that naturally disrupt endosomes, thereby releasing material into the cytoplasm can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126).

Retroviruses: Defective retroviruses are well characterized for use in gene transfer for gene therapy purposes (for a review see Miller, A. D. (1990) Blood 76:271). A recombinant retrovirus can be constructed having nucleotide sequences of interest incorporated into the retroviral genome. Additionally, portions of the retroviral genome can be removed to render the retrovirus replication defective. The replication defective retrovirus is then packaged into virions that can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are available to those skilled in the art. Examples of suitable packaging virus lines include ΨCrip, ΨCre, Ψ2 and ΨAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are available to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

Transformed mammalian cells can then be identified and administered to the mammal from whence they came to permit expression of a CD83 gene product, CD83 transcription factor, CD83 anti-sense nucleic acid, intracellular antibody capable of binding to CD83 proteins, or dominant negative CD83 inhibitors. The efficacy of a particular expression vector system and method of introducing nucleic acid into a cell can be assessed by standard approaches routinely used in the art. For example, DNA introduced into a cell can be detected by a filter hybridization technique (e.g., Southern blotting). RNA produced by transcription of an introduced DNA can be detected, for example, by Northern blotting, RNase protection or reverse transcriptase-polymerase chain reaction (RT-PCR). The CD83 gene product can be detected by an appropriate assay, for example, by immunological detection of a produced CD83 protein, such as with a CD83-specific antibody.

CD83 Antibodies

The invention provides antibody preparations directed against the mutant and wild type CD83 polypeptides of the invention, for example, against a polypeptide having SEQ ID NO:2, SEQ ID NO:4, SEQ ID NO:7, SEQ ID NO:8 or SEQ ID NO:9. Other antibodies of interest can bind to the cytoplasmic tail of CD83.

In one embodiment, the invention provides antibodies that block the function of CD83 polypeptides. Such antibodies may be used as CD83 inhibitory agents in the methods of the invention as described herein. In another embodiment, the antibodies of the invention can activate CD83 activity. Such activating antibodies may be used as CD83 stimulatory agents.

All antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector function, such as participation of the antibody in antibody dependent cellular toxicity.

An antibody that is contemplated for use in the present invention thus can be in any of a variety of forms, including a whole immunoglobulin, an antibody fragment such as Fv, Fab, and similar fragments, a single chain antibody that includes the variable domain complementarity determining regions (CDR), and the like forms, all of which fall under the broad term "antibody," as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments retain some ability to selectively bind with its antigen or receptor and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The preparation of polyclonal antibodies is well-known to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

The preparation of monoclonal antibodies likewise is conventional. See, for example, Kohler & Milstein, Nature, 256: 495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Methods of in vitro and in vivo manipulation of monoclonal antibodies are also available to those skilled in the art. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from antibody libraries using the techniques described in Clackson et al. Nature 352: 624-628 (1991), as well as in Marks et al., J. Mol. Biol. 222: 581-597 (1991).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Another method for generating antibodies involves a Selected Lymphocyte Antibody Method (SLAM). The SLAM technology permits the generation, isolation and manipulation of monoclonal antibodies without the process of hybridoma generation. The methodology principally involves the growth of antibody forming cells, the physical selection of specifically selected antibody forming cells, the isolation of the genes encoding the antibody and the subsequent cloning and expression of those genes.

More specifically, an animal (rabbit, mouse, rat, other) is immunized with a source of specific antigen. This immunization may consist of purified protein, in either native or recombinant form, peptides, DNA encoding the protein of interest or cells expressing the protein of interest. After a suitable period, during which antibodies can be detected in the serum of the animal (usually weeks to months), blood (or other tissue) from the animal is harvested. Lymphocytes are isolated from the blood and cultured under specific conditions to generate antibody-forming cells, with antibody being secreted into the culture medium. These cells are detected by any of several means (complement mediated lysis of antigen-bearing cells, fluorescence detection or other) and then isolated using micromanipulation technology. The individual antibody forming cells are then processed for eventual single cell PCR to obtain the expressed Heavy and Light chain genes that encode the specific antibody. Once obtained and sequenced, these genes are cloned into an appropriate expression vector and recombinant, monoclonal antibody produced in a heterologous cell system. These antibodies are then purified via standard methodologies such as the use of protein A affinity columns. These types of methods are further described in Babcook, et al., Proc. Natl. Acad. Sci. (USA) 93: 7843-7848 (1996); U.S. Pat. No. 5,627,052; and PCT WO 92/02551 by Schrader.

Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998). The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the antibody is obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad. Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab=monovalent fragments. Alternatively, an enzymatic cleavage using pepsin produces two monovalent Fab' fragments and an Fc fragment directly. These methods are described, for example, in U.S. Pat. No. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11: 1271-77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention further contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies can comprise substantially all of at least one, and typically two, variable domains, in which all or substantially all of the CDR regions correspond to those of a non-human immunoglobulin and all or substantially all of the Fv regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998).

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody.

The antibodies of the invention are isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or non-proteinaceous solutes. The term "isolated antibody" also includes antibodies within recombinant cells because at least one component of the antibody's natural environment will not be present. Ordinarily, however, isolated antibody will be prepared by at least one purification step.

If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain.

The invention also provides antibodies that can bind to CD83 polypeptides. Sequences of complementarity determining regions (CDRs) or hypervariable regions from light and heavy chains of these anti-CD83 antibodies are provided.

For example, a heavy chain variable region having a CDR1 sequence of SYDMT (SEQ ID NO:23), SYDMS (SEQ ID NO:24), DYDLS (SEQ ID NO:25) or SYDMS (SEQ ID NO:26) can be used in an antibody or other binding moiety to bind to CD83 gene products. In other embodiments, a heavy chain variable region having a CDR2 sequence of YASGSTYY (SEQ ID NO:27), SSSGTTYY (SEQ ID NO:28), YASGSTYY (SEQ ID NO:29), AIDGNPYY (SEQ ID NO:30) or STAYNSHY (SEQ ID NO:31) can be used in an antibody or other binding moiety to bind to CD83 gene products. In further embodiments of the invention, a heavy chain variable region having a CDR3 sequence of EHAGYSGDTGH (SEQ ID NO:32), EGAGVSMT (SEQ ID NO:33), EDAGFSNA (SEQ ID NO:34), GAGD (SEQ ID NO:35) or GGSWLD (SEQ ID NO:36) can be used in an antibody or other binding moiety to bind to CD83 gene products.

Moreover, a light chain variable region having a CDR1 sequence of RCAYD (SEQ ID NO:37), RCADVV (SEQ ID NO:38), or RCALV (SEQ ID NO:39) can be used in an antibody or other binding moiety to bind to CD83 gene products. In other embodiments, a light chain variable region having a CDR2 sequence of QSISTY (SEQ ID NO:40), QSVSSY (SEQ ID NO:41), ESISNY (SEQ ID NO:42), KNVYNNNW (SEQ ID NO:43), or QSVYDNDE (SEQ ID NO:43) can be used in an antibody or other binding moiety to bind to CD83 gene products. In further embodiments, a light chain variable region having a CDR3 sequence of QQGYTHSNVDNV (SEQ ID NO:44), QQGYSISDIDNA (SEQ ID NO:45), QCTSGGKFISDGAA (SEQ ID NO:46), AGDYSSSSDNG (SEQ ID NO:47), or QATHYSSDWLTY (SEQ ID NO:48) can be used in an antibody or other binding moiety to bind to CD83 gene products.

Light and heavy chains that can bind CD83 polypeptides are also provided by the invention. For example, in one embodiment, the invention provides a 20D04 light chain that can bind to CD83 polypeptides. The amino acid sequence for this 20D04 light chain is provided below (SEQ ID NO:11).

```
  1 MDMRAPTQLL GLLLLWLPGA RCADVVMTQT PASVSAAVGG

41 TVTINCQASE SISNYLSWYQ QKPGQPPKLL IYRTSTLASG

81 VSSRFKGSGS GTEYTLTISG VQCDDVATYY CQCTSGGKFI

121 SDGAAFGGGT EVVVKGDPVA PTVLLFPPSS DEVATGTVTI

161 VCVANKYFPD VTVTWEVDGT TQTTGIENSK TPQNSADCTY

201 NLSSTLTLTS TQTTSHKEYT CKVTQGTTSV VQSFSRKNC
```

A nucleic acid sequence for this 20D04 anti-CD83 light chain is provided below (SEQ ID NO:12).

```
  1 ATGGACATGA GGGCCCCCAC TCAGCTGCTG GGGCTCCTGC

41 TGCTCTGGCT CCCAGGTGCC AGATGTGCCG ATGTCGTGAT

81 GACCCAGACT CCAGCCTCCG TGTCTGCAGC TGTGGGAGGC

121 ACAGTCACCA TCAATTGCCA GGCCAGTGAA AGCATTAGCA

161 ACTACTTATC CTGGTATCAG CAGAAACCAG GGCAGCCTCC

201 CAAGCTCCTG ATCTACAGGA CATCCACTCT GGCATCTGGG

241 GTCTCATCGC GGTTCAAAGG CAGTGGATCT GGGACAGAGT

281 ACACTCTCAC CATCAGCGGC GTGCAGTGTG ACGATGTTGC

321 CACTTACTAC TGTCAATGCA CTTCTGGTGG GAAGTTCATT
```

-continued

```
361 AGTGATGGTG CTGCTTTCGG CGGAGGGACC GAGGTGGTGG
401 TCAAAGGTGA TCCAGTTGCA CCTACTGTCC TCCTCTTCCC
441 ACCATCTAGC GATGAGGTGG CAACTGGAAC AGTCACCATC
481 GTGTGTGTGG CGAATAAATA CTTTCCCGAT GTCACCGTCA
521 CCTGGGAGGT GGATGGCACC ACCCAAACAA CTGGCATCGA
561 GAACAGTAAA ACACCGCAGA ATTCTGCAGA TTGTACCTAC
601 AACCTCAGCA GCACTCTGAC ACTGACCAGC ACACAGTACA
641 ACAGCCACAA AGAGTACACC TGCAAGGTGA CCCAGGGCAC
681 GACCTCAGTC GTCCAGAGCT TCAGTAGGAA GAACTGTTAA
```

In another embodiment, the invention provides a 20D04 heavy chain that can bind to CD83 polypeptides. The amino acid sequence for this 20D04 heavy chain is provided below (SEQ ID NO:13).

```
  1 METGLRWLLL VAVLKGVQCQ SVEESGGRLV TPGTPLTLTC
 41 TVSGFSLSNN AINWVRQAPG KGLEWIGYIW SGGLTYYANW
 81 AEGRFTISKT STTVDLKMTS PTIEDTATYF CARGINNSAL
121 WGPGTLVTVS SGQPKAPSVF PLAPCCGDTP SSTVTLGCLV
161 KGYLPEPVTV TWNSGTLTNG VRTFPSVRQS SGLYSLSSVV
201 SVTSSSQPVT CNVAHPATNT KVDKTVAPST CSKPTCPPPE
241 LLGGPSVFIF PPKPKDTLMI SRTPEVTCVV VDVSQDDPEV
281 QFTWYINNEQ VRTARPPLRE QQFNSTIRVV STLPIAHQDW
321 LRGKEFKCKV HNKALPAPIE KTISKARGQP LEPKVYTMGP
361 PREELSSRSV SLTCMINGFY PSDISVEWEK NGKAEDNYKT
401 TPAVLDSDGS YFLYNKLSVP TSEWQRGDVF TCSVMHEALH
441 NHYTQKSISR SPGK
```

A nucleic acid sequence for this 20D04 anti-CD83 heavy chain is provided below (SEQ ID NO:14).

```
  1 ATGGAGACAG GCCTGCGCTG GCTTCTCCTG GTCGCTGTGC
 41 TCAAAGGTGT CCAGTGTCAG TCGGTGGAGG AGTCCGGGGG
 81 TCGCCTGGTC ACGCCTGGGA CACCCCTGAC ACTCACCTGC
121 ACCGTCTCTG GATTCTCCCT CAGTAACAAT GCAATAAACT
161 GGGTCCGCCA GGCTCCAGGG AAGGGGCTAG AGTGGATCGG
201 ATACATTTGG AGTGGTGGGC TTACATACTA CGCGAACTGG
241 GCGGAAGGCC GATTCACCAT CTCCAAAACC TCGACTACGG
281 TGGATCTGAA GATGACCAGT CCGACAATCG AGGACACGGC
321 CACCTATTTC TGTGCCAGAG GGATTAATAA CTCCGCTTTG
361 TGGGGCCAG GCACCCTGGT CACCGTCTCC TCAGGGCAAC
401 CTAAGGCTCC ATCAGTCTTC CCACTGGCCC CCTGCTGCGG
441 GGACACACCC TCTAGCACGG TGACCTTGGG CTGCCTGGTC
481 AAAGGCTACC TCCCGGAGCC AGTGACCGTG ACCTGGAACT
521 CGGGCACCCT CACCAATGGG GTACGCACCT TCCCGTCCGT
561 CCGGCAGTCC TCAGGCCTCT ACTCGCTGAG CAGCGTGGTG
601 AGCGTGACCT CAAGCAGCCA GCCCGTCACC TGCAACGTGG
641 CCCACCCAGC CACCAACACC AAAGTGGACA AGACCGTTGC
681 GCCCTCGACA TGCAGCAAGC CCACGTGCCC ACCCCCTGAA
721 CTCCTGGGGG GACCGTCTGT CTTCATCTTC CCCCCAAAAC
761 CCAAGGACAC CCTCATGATC TCACGCACCC CCGAGGTCAC
801 ATGCGTGGTG GTGGACGTGA GCCAGGATGA CCCCGAGGTG
841 CAGTTCACAT GGTACATAAA CAACGAGCAG GTGCGCACCG
881 CCCGGCCGCC GCTACGGGAG CAGCAGTTCA ACAGCACGAT
921 CCGCGTGGTC AGCACCCTCC CCATCGCGCA CCAGGACTGG
961 CTGAGGGGCA AGGAGTTCAA GTGCAAAGTC CACAACAAGG
1001 CACTCCCGGC CCCCATCGAG AAACCATCT CCAAAGCCAG
1041 AGGGCAGCCC CTGGAGCCGA AGGTCTACAC CATGGGCCCT
1081 CCCCGGGAGG AGCTGAGCAG CAGGTCGGTC AGCCTGACCT
1121 GCATGATCAA CGGCTTCTAC CCTTCCGACA TCTCGGTGGA
1161 GTGGGAGAAG AACGGGAAGG CAGAGGACAA CTACAAGACC
1201 ACGCCGGCCG TGCTGGACAG CGACGGCTCC TACTTCCTCT
1241 ACAACAAGCT CTCAGTGCCC ACGAGTGAGT GGCAGCGGGG
1281 CGACGTCTTC ACCTGCTCCG TGATGCACGA GGCCTTGCAC
1321 AACCACTACA CGCAGAAGTC CATCTCCCGC TCTCCGGGTA
1361 AA
```

In another embodiment, the invention provides a 11G05 light chain that can bind to CD83 polypeptides. The amino acid sequence for this 11G05 light chain is provided below (SEQ ID NO:15).

```
  1 MDTRAPTQLL GLLLLWLPGA RCADVVMTQT PASVSAAVGG
 41 TVTINCQSSK NVYNNNWLSW FQQKPGQPPK LLIYYASTLA
 81 SGVPSRFRGS GSGTQFTLTI SDVQCDDAAT YYCAGDYSSS
121 SDNGFGGGTE VVVKGDPVAP TVLLFPPSSD EVATGTVTIV
161 CVANKYFPDV TVTWEVDGTT QTTGIENSKT PQNSADCTYN
201 LSSTLTLTST QYNSHKEYTC KVTQGTTSVV QSFSRKNC
```

A nucleic acid sequence for this 11 G05 anti-CD83 light chain is provided below (SEQ ID NO:16).

```
  1 ATGGACACCA GGGCCCCCAC TCAGCTGCTG GGGCTCCTGC
 41 TGCTCTGGCT CCCAGGTGCC AGATGTGCCG ACGTCGTGAT
 81 GACCCAGACT CCAGCCTCCG TGTCTGCAGC TGTGGGAGGC
121 ACAGTCACCA TCAATTGCCA GTCCAGTAAG AATGTTTATA
161 ATAACAACTG GTTATCCTGG TTTCAGCAGA AACCAGGGCA
201 GCCTCCCAAG CTCCTGATCT ATTATGCATC CACTCTGGCA
```

```
241 TCTGGGGTCC CATCGCGGTT CAGAGGCAGT GGATCTGGGA
281 CACAGTTCAC TCTCACCATT AGCGACGTGC AGTGTGACGA
321 TGCTGCCACT TACTACTGTG CAGGCGATTA TAGTAGTAGT
361 AGTGATAATG GTTTCGGCGG AGGGACCGAG GTGGTGGTCA
401 AAGGTGATCC AGTTGCACCT ACTGTCCTCC TCTTCCCACC
441 ATCTAGCGAT GAGGTGGCAA CTGGAACAGT CACCATCGTG
481 TGTGTGGCGA ATAAATACTT TCCCGATGTC ACCGTCACCT
521 GGGAGGTGGA TGGCACCACC CAAACAACTG GCATCGAGAA
561 CAGTAAAACA CCGCAGAATT CTGCAGATTG TACCTACAAC
601 CTCAGCAGCA CTCTGACACT GACCAGCACA CAGTACAACA
641 GCCACAAAGA GTACACCTGC AAGGTGACCC AGGGCACGAC
681 CTCAGTCGTC CAGAGCTTCA GTAGGAAGAA CTGTTAA
```

In another embodiment, the invention provides a 11G05 heavy chain that can bind to CD83 polypeptides. The amino acid sequence for this 11G05 heavy chain is provided below (SEQ ID NO:17).

```
  1 METGLRWLLL VAVLKGVQCQ SVEESGGRLV TPGTPLTLTC
 41 TVSGFTISDY DLSWVRQAPG EGLKYIGFIA IDGNPYYATW
 81 AKGRFTISKT STTVDLKITA PTTEDTATYF CARGAGDLWG
121 PGTLVTVSSG QPKAPSVFPL APCCGDTPSS TVTLGCLVKG
161 YLPEPVTVTW NSGTLTNGVR TFPSVRQSSG LYSLSSVVSV
201 TSSSQPVTCN VAHPATNTKV DKTVAPSTCS KPTCPPPELL
241 GGPSVFIFPP KPKDTLMISR TPEVTCVVVD VSQDDPEVQF
281 TWYINNEQVR TARPPLREQQ FNSTIRVVST LPIAHQDWLR
321 GKEFKCKVHN KALPAPIEKT ISKARGQPLE PKVYTMGPPR
361 EELSSRSVSL TCMINGFYPS DISVEWEKNG KAEDNYKTTP
401 AVLDSDGSYF LYNKLSVPTS EWQRGDVFTC SVMHEALHNH
441 YTQKSISRSP GK
```

A nucleic acid sequence for this 11G05 anti-CD83 heavy chain is provided below (SEQ ID NO:18).

```
  1 ATGGAGACAG GCCTGCGCTG GCTTCTCCTG GTCGCTGTGC
 41 TCAAAGGTGT CCAGTGTCAG TCGGTGGAGG AGTCCGGGGG
 81 TCGCCTGGTC ACGCCTGGGA CACCCCTGAC ACTCACCTGC
121 ACAGTCTCTG GATTCACCAT CAGTGACTAC GACTTGAGCT
161 GGGTCCGCCA GGCTCCAGGG GAGGGGCTGA AATACATCGG
201 ATTCATTGCT ATTGATGGTA ACCCATACTA CGCGACCTGG
241 GCAAAGGCC GATTCACCAT CTCCAAACC TCGACCACGG
281 TGGATCTGAA AATCACCGCT CCGACAACCG AAGACACGGC
321 CACGTATTTC TGTGCCAGAG GGGCAGGGA CCTCTGGGGC
361 CCAGGGACCC TCGTCACCGT CTCTTCAGGG CAACCTAAGG
```

```
401 CTCCATCAGT CTTCCCACTG GCCCCCTGCT GCGGGGACAC
441 ACCCTCTAGC ACGGTGACCT TGGGCTGCCT GGTCAAAGGC
481 TACCTCCCGG AGCCAGTGAC CGTGACCTGG AACTCGGGCA
521 CCCTCACCAA TGGGGTACGC ACCTTCCCGT CCGTCCGGCA
561 GTCCTCAGGC CTCTACTCGC TGAGCAGCGT GGTGAGCGTG
601 ACCTCAAGCA GCCAGCCCGT CACCTGCAAC GTGGCCCACC
641 CAGCCACCAA CACCAAAGTG GACAAGACCG TTGCGCCCTC
681 GACATGCAGC AAGCCCACGT GCCCACCCCC TGAACTCCTG
721 GGGGGACCGT CTGTCTTCAT CTTCCCCCCA AAACCCAAGG
761 ACACCCTCAT GATCTCACGC ACCCCCGAGG TCACATGCGT
801 GGTGGTGGAC GTGAGCCAGG ATGACCCCGA GGTGCAGTTC
841 ACATGGTACA TAAACAACGA GCAGGTGCGC ACCGCCCGGC
881 CGCCGCTACG GGAGCAGCAG TTCAACAGCA CGATCCGCGT
921 GGTCAGCACC CTCCCCATCG CGCACCAGGA CTGGCTGAGG
961 GGCAAGGAGT TCAAGTGCAA AGTCCACAAC AAGGCACTCC
1001 CGGCCCCCAT CGAGAAAACC ATCTCCAAAG CCAGAGGGCA
1041 GCCCCTGGAG CCGAAGGTCT ACACCATGGG CCCTCCCCGG
1081 GAGGAGCTGA GCAGCAGGTC GGTCAGCCTG ACCTGCATGA
1120 TCAACGGCTT CTACCCTTCC GACATCTCGG TGGAGTGGGA
1161 GAAGAACGGG AAGGCAGAGG ACAACTACAA GACCACGCCG
1201 GCCGTGCTGG ACAGCGACGG CTCCTACTTC CTCTACAACA
1241 AGCTCTCAGT GCCCACGAGT GAGTGGCAGC GGGGCGACGT
1281 CTTCACCTGC TCCGTGATGC ACGAGGCCTT GCACAACCAC
1321 TACACGCAGA AGTCCATCTC CCGCTCTCCG GGTAAA
```

In another embodiment, the invention provides a 14C12 light chain that can bind to CD83 polypeptides. The amino acid sequence for this 14C12 light chain is provided below (SEQ ID NO:19).

```
  1 MDXPAPTQLL GLLLLWLPGA RCALVMTQTP ASVSAAVGGT
 41 VTINCQSSQS VYDNDELSWY QQKPGQPPKL LIYLASKLAS
 81 GVPSRFKGSG SGTQFALTIS GVQCDDAATY YCQATHYSSD
121 WYLTFGGGTE VVVKGDPVAP TVLLFPPSSD EVATGTVTIV
161 CVANKYFPDV TVTWEVDGTT QTTGIENSKT PQNSADCTYN
201 LSSTLTLTST QYNSHKEYTC KVTQGTTSVV QSFSRKNC
```

A nucleic acid sequence for this 14C12 anti-CD83 light chain is provided below (SEQ ID NO:20).

```
  1 ATGGACATRA GGGCCCCCAC TCAGCTGCTG GGGCTCCTGC
 41 TGCTCTGGCT CCCAGGTGCC AGATGTGCCC TTGTGATGAC
 81 CCAGACTCCA GCCTCCGTGT CTGCAGCTGT GGGAGGCACA
121 GTCACCATCA ATTGCCAGTC CAGTCAGAGT GTTTATGATA
```

```
161 ACGACGAATT ATCCTGGTAT CAGCAGAAAC CAGGGCAGCC
201 TCCCAAGCTC CTGATCTATC TGGCATCCAA GTTGGCATCT
241 GGGGTCCCAT CCCGATTCAA AGGCAGTGGA TCTGGGACAC
281 AGTTCGCTCT CACCATCAGC GGCGTGCAGT GTGACGATGC
321 TGCCACTTAC TACTGTCAAG CCACTCATTA TAGTAGTGAT
361 TGGTATCTTA CTTTCGGCGG AGGGACCGAG GTGGTGGTCA
401 AAGGTGATCC AGTTGCACCT ACTGTCCTCC TCTTCCCACC
441 ATCTAGCGAT GAGGTGGCAA CTGGAACAGT CACCATCGTG
481 TGTGTGGCGA ATAAATACTT TCCCGATGTC ACCGTCACCT
521 GGGAGGTGGA TGGCACCACC CAAACAACTG GCATCGAGAA
561 CAGTAAAACA CCGCAGAATT CTGCAGATTG TACCTACAAC
601 CTCAGCAGCA CTCTGACACT GACCAGGACA CAGTACAACA
641 GCCACAAAGA GTACACCTGC AAGGTGACCC AGGGCACGAC
681 CTCAGTCGTC CAGAGCTTCA GTAGGAAGAA CTGTTAA
```

In another embodiment, the invention provides a 14C12 heavy chain that can bind to CD83 polypeptide's. The amino acid sequence for this 14C12 heavy chain is provided below (SEQ ID NO:21).

```
  1 METGLRWLLL VAVLKGVHCQ SVEESGGRLV TPGTPLTLTC
 41 TASGFSRSSY DMSWVRQAPG KGLEWVGVIS TAYNSHYASW
 81 AKGRFTISRT STTVDLKMTS LTTEDTATYF CARGGSWLDL
121 WGQGTLVTVS SGQPKAPSVF PLAPCCGDTP SSTVTLGCLV
161 KGYLPEPVTV TWNSGTLTNG VRTFPSVRQS SGLYSLSSVV
201 SVTSSSQPVT CNVAHPATNT KVDKTVAPST CSKPTCPPPE
241 LLGGPSVFIF PPKPKDTLMI SRTPEVTCVV VDVSQDDPEV
281 QFTWYINNEQ VRTARPPLRE QQFNSTIRVV STLPIAHQDW
321 LRGKEFKCKV HNKALPAPIE KTISKARGQP LEPKVYTMGP
361 PREELSSRSV SLTCMINGFY PSDISVEWEK NGKAEDNYKT
401 TPAVLDSDGS YFLYNKLSVP TSEWQRGDVF TCSVMHEALH
441 NHYTQKSISR SPGK
```

A nucleic acid sequence for this 14C12 anti-CD83 heavy chain is provided below (SEQ ID NO:22).

```
  1 ATGGAGACAG GCCTGCGCTG GCTTCTCCTG GTCGCTGTGC
 41 TCAAAGGTGT CCACTGTCAG TCGGTGGAGG AGTCCGGGGG
 81 TCGCCTGGTC ACGCCTGGGA CACCCCTGAC ACTCACCTGC
121 ACAGCCTCTG GATTCTCCCG CAGCAGCTAC GACATGAGCT
161 GGGTCCGCCA GGCTCCAGGG AAGGGGCTGG AATGGGTCGG
201 AGTCATTAGT ACTGCTTATA ACTCACACTA CGCGAGCTGG
241 GCAAAGGCC GATTCACCAT CTCCAGAACC TCGACCACGG
281 TGGATCTGAA AATGACCAGT CTGACAACCG AAGACACGGC
```

```
 321 CACCTATTTC TGTGCCAGAG GGGGTAGTTG GTTGGATCTC
 361 TGGGGCCAGG GCACCCTGGT CACCGTCTCC TCAGGGCAAC
 401 CTAAGGCTCC ATCAGTCTTC CCACTGGCCC CCTGCTGCGG
 441 GGACACACCC TCTAGCACGG TGACCTTGGG CTGCCTGGTC
 481 AAAGGCTACC TCCCGGAGCC AGTGACCGTG ACCTGGAACT
 521 CGGGCACCCT CACCAATGGG GTACGCACCT TCCCGTCCGT
 561 CCGGCAGTCC TCAGGCCTCT ACTCGCTGAG CAGCGTGGTG
 601 AGCGTGACCT CAAGCAGCCA GCCCGTCACC TGCAACGTGG
 641 CCCACCCAGC CACCAACACC AAAGTGGACA AGACCGTTGC
 681 GCCCTCGACA TGCAGCAAGC CCACGTGCCC ACCCCCTGAA
 721 CTCCTGGGGG GACCGTCTGT CTTCATCTTC CCCCCAAAAC
 761 CCAAGGACAC CCTCATGATC TCACGCACCC CCGAGGTCAC
 801 ATGCGTGGTG GTGGACGTGA GCCAGGATGA CCCCGAGGTG
 841 CAGTTCACAT GGTACATAAA CAACGAGCAG GTGCGCACCG
 881 CCCGGCCGCC GCTACGGGAG CAGCAGTTCA ACAGCACGAT
 921 CCGCGTGGTC AGCACCCTCC CCATCGCGCA CCAGGACTGG
 961 CTGAGGGCA AGGAGTTCAA GTGCAAAGTC CACAACAAGG
1001 CACTCCCGGC CCCCATCGAG AAAACCATCT CCAAAGCCAG
1041 AGGGCAGCCC CTGGAGCCGA AGGTCTACAC CATGGGCCCT
1081 CCCCGGGAGG AGCTGAGCAG CAGGTCGGTC AGCCTGACCT
1121 GCATGATCAA CGGCTTCTAC CCTTCCGACA TCTCGGTGGA
1161 GTGGGAGAAG AACGGGAAGG CAGAGGACAA CTACAAGACC
1200 ACGCCGGCCG TGCTGGACAG CGACGGCTCC TACTTCCTCT
1241 ACAACAAGCT CTCAGTGCCC ACGAGTGAGT GGCAGCGGGG
1281 CGACGTCTTC ACCTGCTCCG TGATGCACGA GGCCTTGCAC
1321 AACCACTACA CGCAGAAGTC CATCTCCCGC TCTCCGGGTA
1361 AA
```

In another embodiment, the invention provides a M83 020B08L light chain that can bind to CD83 polypeptides. The amino acid sequence for this M83 020B08L light chain is provided below (SEQ ID NO:58).

```
  1 MDMRAPTQLL GLLLLWLPGA RCAYDMTQTP ASVEVAVGGT
 41 VTIKCQASQS ISTYLDWYQQ KPGQPPKLLI YDASDLASGV
 81 PSRFKGSGSG TQFTLTISDL ECADAATYYC QQGYTHSNVD
121 NVFGGGTEVV VKGDPVAPTV LLFPPSSDEV ATGTVTIVCV
161 ANKYFPDVTV TWEVDGTTQT TGIENSKTPQ NSADCTYNLS
201 STLTLTSTQY NSHKEYTCKV TQGTTSVVQS FSRKNC
```

A nucleic acid sequence for this M83 020B08L anti-CD83 light chain is provided below (SEQ ID NO:59).

```
  1 ATGGACATGA GGGCCCCCAC TCAGCTGCTG GGGCTCCTGC
 41 TGCTCTGGCT CCCAGGTGCC AGATGTGCCT ATGATATGAC
 81 CCAGACTCCA GCCTCTGTGG AGGTAGCTGT GGGAGGCACA
121 GTCACCATCA AGTGCCAGGC CAGTCAGAGC ATTAGTACCT
161 ACTTAGACTG GTATCAGCAG AAACCAGGGC AGCCTCCCAA
201 GCTCCTGATC TATGATGCAT CCATGCTGGC ATCTGGGGTC
241 CCATCGCGGT TCAAAGGCAG TGGATCTGGG ACACAGTTCA
281 CTCTCACCAT CAGCGACCTG GAGTGTGCCG ATGCTGCCAC
321 TTACTACTGT CAACAGGGTT ATACACATAG TAATGTTGAT
361 AATGTTTTCG GCGGAGGGAC CGAGGTGGTG GTCAAAGGTG
401 ATCCAGTTGC ACCTACTGTC CTCCTCTTCC CACCATCTAG
441 CGATGAGGTG GCAACTGGAA CAGTCACCAT CGTGTGTGTG
481 GCGAATAAAT ACTTTCCCGA TGTCACCGTC ACCTGGGAGG
521 TGGATGGCAC CACCCAAACA ACTGGCATCG AGAACAGTAA
561 AACACCGCAG AATTCTGCAG ATTGTACCTA CAACCTCAGC
601 AGCACTCTGA CACTGACCAG CACACAGTAC AACAGCCACA
641 AAGAGTACAC CTGCAAGGTG ACCCAGGGCA CGACCTCAGT
681 CGTCCAGAGC TTCAGTAGGA AGAACTGTTA A
```

In another embodiment, the invention provides a M83 020B08H heavy chain that can bind to CD83 polypeptides. The amino acid sequence for this M83 020B08H heavy chain is provided below (SEQ ID NO:60).

```
  1 METGLRWLLL VAVLKGVQCQ SVEESGGRLV TPGTPLTLTC
 41 TVSGFSLSSY DMTWVRQAPQ KGLEWIGIIY ASGTTYYANW
 81 AKGRFTISKT STTVDLKVTS PTIGDTATYF CAREGAGVSM
121 TLWGPGTLVT VSSGQPKAPS VFPLAPCCGD TPSSTVTLGC
161 LVKGYLPEPV TVTWNSGTLT NGVRTFPSVR QSSGLYSLSS
201 VVSVTSSSQP VTCNVAHPAT NTKVDKTVAP STCSKPTCPP
241 PELLGGPSVF IFPPKPKDTL MISRTPEVTC VVVDVSQDDP
281 EVQFTWYINN EQVRTARPPL REQQFNSTIR VVSTLPIAHQ
321 DWLRGKEFKC KVHNKALPAP IEKTISKARG QPLEPKVYTM
361 GPPREELSSR SVSLTCMING FYPSDISVEW EKNGKAEDNY
401 KTTPAVLDSD GSYFLYNKLS VPTSEWQRGD VFTCSVMHEA
441 LHNHYTQKSI SRSPGK
```

A nucleic acid sequence for this M83 020B08H anti-CD83 heavy chain is provided below (SEQ ID NO:61).

```
  1 ATGGAGACAG GCCTGCGCTG GCTTCTCCTG GTCGCTGTGC
 41 TCAAGGTGT CCAGTGTCAG TCGGTGGAGG AGTCCGGGGG
 81 TCGCCTGGTC ACGCCTGGGA CACCCCTGAC ACTCACCTGC
121 ACAGTCTCTG GATTCTCCCT CAGCAGCTAC GACATGACCT
161 GGGTCCGCCA GGCTCCAGGG AAGGGGCTGG AATGGATCGG
201 AATCATTTAT GCTAGTGGTA CCACATACTA CGCGAACTGG
241 GCGAAAGGCC GATTCACCAT CTCCAAAACC TCGACCACGG
281 TGGATCTGAA AGTCACCAGT CCGACAATCG GGGACACGGC
321 CACCTATTTC TGTGCCAGAG AGGGGGCTGG TGTTAGTATG
361 ACCTTGTGGG GCCCAGGCAC CCTGGTCACC GTCTCCTCAG
401 GGCAACCTAA GGCTCCATCA GTCTTCCCAC TGGCCCCCTG
441 CTGCGGGGAC ACACCCTCTA GCACGGTGAC CTTGGGCTGC
481 CTGGTCAAAG GCTACCTCCC GGAGCCAGTG ACCGTGACCT
521 GGAACTCGGG CACCCTCACC AATGGGGTAC GCACCTTCCC
561 GTCCGTCCGG CAGTCATCAG GCCTCTACTC GCTGAGCAGC
601 GTGGTGAGCG TGACCTCAAG CAGCCAGCCC GTCACCTGCA
641 ACGTGGCCCA CCCAGCCACC AACACCAAAG TGGACAAGAC
681 CGTTGCGCCC TCGACATGCA GCAAGCCCAC GTGCCCACCC
721 CCTGAACTCC TGGGGGGACC GTCTGTCTTC ATCTTCCCCC
761 CAAAACCCAA GGACACCCTC ATGATCTCAC GCACCCCCGA
801 GGTCACATGC GTGGTGGTGG ACGTGAGCCA GGATGACCCC
841 GAGGTGCAGT TCACATGGTA CATAAACAAC GAGCAGGTGC
881 GCACCGCCCG GCCGCCGCTA CGGGAGCAGC AGTTCAACAG
921 CACGATCCGC GTGGTCAGCA CCCTCCCCAT CGCGCACCAG
961 GACTGGCTGA GGGGCAAGGA GTTCAAGTGC AAAGTCCACA
1001 ACAAGGCACT CCCGGCCCCC ATCGAGAAAA CCATCTCCAA
1041 AGCCAGAGGG CAGCCCCTGG AGCCGAAGGT CTACACCATG
1081 GGCCCTCCCC GGGAGGAGCT GAGCAGCAGG TCGGTCAGCC
1121 TGACCTGCAT GATCAACGGC TTCTACCCTT CCGACATCTC
1161 GGTGGAGTGG GAGAAGAACG GGAAGGCAGA GGACAACTAC
1201 AAGACCACGC CGGCCGTGCT GGACAGCGAC GGCTCCTACT
1241 TCCTCTACAA CAAGCTCTCA GTGCCCACGA GTGAGTGGCA
1281 GCGGGGCGAC GTCTTCACCT GCTCCGTGAT GCACGAGGCC
1321 TTGCACAACC ACTACACGCA GAAGTCCATC TCCCGCTCTC
1361 CGGGTAAA
```

In another embodiment, the invention provides a M83 006G05L light chain that can bind to CD83 polypeptides. The amino acid sequence for this M83 006G05L light chain is provided below (SEQ ID NO:62).

```
  1 MDMRAPTQLL GLLLLWLPGA RCAYDMTQTP ASVEVAVGGT
 41 VAIKCQASQS VSSYLAWYQQ KPGQPPKPLI YEASMLAAGV
 81 SSRFKGSGSG TDFTLTISDL ECDDAATYYC QQGYSISDID
121 NAFGGGTEVV VKGDPVAPTV LLFPPSSDEV ATGTVTIVCV
```

-continued

```
161 ANKYFPDVTV TWEVDGTTQT TGIENSKTPQ NSADCTYNLS

201 STLTLTSTQY NSHKEYTCKV TQGTTSVVQS FSRKNC
```

A nucleic acid sequence for M83 006G05L anti-CD83 light chain is provided below (SEQ ID NO:63).

```
  1 ATGGACATGA GGGCCCCCAC TCAACTGCTG GGGCTCCTGC
 41 TGCTCTGGCT CCCAGGTGCC AGATGTGCCT ATGATATGAC
 81 CCAGACTCCA GCCTCTGTGG AGGTAGCTGT GGGAGGCACA
121 GTCGCCATCA AGTGCCAGGC CAGTCAGAGC GTTAGTAGTT
161 ACTTAGCCTG GTATCAGCAG AAACCAGGGC AGCCTCCCAA
201 GCCCCTGATC TACGAAGCAT CCATGCTGGC GGCTGGGGTC
241 TCATCGCGGT TCAAAGGCAG TGGATCTGGG ACAGACTTCA
281 CTCTCACCAT CAGCGACCTG GAGTGTGACG ATGCTGCCAC
321 TTACTATTGT CAACAGGGTT ATTCTATCAG TGATATTGAT
361 AATGCTTTCG GCGGAGGGAC CGAGGTGGTG GTCAAAGGTG
401 ATCCAGTTGC ACCTACTGTC CTCCTCTTCC CACCATCTAG
441 CGATGAGGTG GCAACTGGAA CAGTCACCAT CGTGTGTGTG
481 GCGAATAAAT ACTTTCCCGA TGTCACCGTC ACCTGGGAGG
521 TGGATGGCAC CACCCAAACA ACTGGCATCG AGAACAGTAA
561 AACACCGCAG AATTCTGCAG ATTGTACCTA CAACCTCAGC
601 AGCACTCTGA CACTGACCAG CACACAGTAC AACAGCCACA
641 AAGAGTACAC CTGCAAGGTG ACCCAGGGCA CGACCTCAGT
681 CGTCCAGAGC TTCAGTAGGA AGAACTGTTA A
```

In another embodiment, the invention provides a M83 006G05L heavy chain that can bind to CD83 polypeptides. The amino acid sequence for this M83 006G05L heavy chain is provided below (SEQ ID NO:64).

```
  1 METGLRWLLL VAVLKGVQCQ SVEESGGRLV SPGTPLTLTC
 41 TASGFSLSSY DMSWVRQAPG KGLEYIGIIS SSGSTYYASW
 81 AKGRFTISKT STTVDLEVTS LTTEDTATYF CSREHAGYSG
121 DTGHLWGPGT LVTVSSGQPK APSVFPLAPC CGDTPSSTVT
161 LGCLVKGYLP EPVTVTWNSG TLTNGVRTFP SVRQSSGLYS
201 LSSVVSVTSS SQPVTCNVAH PATNTKVDKT VAPSTCSKPT
241 CPPPELLGGP SVFIFPPKPK DTLMISRTPE VTCVVVDVSQ
281 DDPEVQFTWY INNEQVRTAR PPLREQQFNS TIRVVSTLPI
321 AHQDWLRGKE FKCKVHNKAL PAPIEKTISK ARGQPLEPKV
361 YTMGPPREEL SSRSVSLTCM INGFYPSDIS VEWEKNGKAE
401 DNYKTTPAVL DSDGSYFLYN KLSVPTSEWQ RGDVFTCSVM
441 HEALHNHYTQ KSISRSPGK
```

A nucleic acid sequence for this M83 006G05L anti-CD83 heavy chain is provided below (SEQ ID NO:65).

```
   1 ATGGAGACAG GCCTGCGCTG GCTTCTCCTG GTCGCTGTGC
  41 TCAAAGGTGT CCAGTGTCAG TCGGTGGAGG AGTCCGGGGG
  81 TCGCCTGGTC TCGCCTGGGA CACCCCTGAC ACTCACCTGC
 121 ACAGCCTCTG GATTCTCCCT CAGTAGCTAC GACATGAGCT
 161 GGGTCCGCCA GGCTCCAGGG AAGGGGCTGG AATACATCGG
 201 AATCATTAGT AGTAGTGGTA GCACATACTA CGCGAGCTGG
 241 GCGAAAGGCC GATTCACCAT CTCCAAAACC TCGACCACGG
 281 TGGATCTGGA AGTGACCAGT CTGACAACCG AGGACACGGC
 321 CACCTATTTC TGTAGTAGAG AACATGCTGG TTATAGTGGT
 361 GATACGGGTC ACTTGTGGGG CCCAGGCACC CTGGTCACCG
 401 TCTCCTCGGG GCAACCTAAG GCTCCATCAG TCTTCCCACT
 441 GGCCCCCTGC TGCGGGGACA CACCCTCTAG CACGGTGACC
 481 TTGGGCTGCC TGGTCAAAGG CTACCTCCCG GAGCCAGTGA
 521 CCGTGACCTG GAACTCGGGC ACCCTCACCA ATGGGGTACG
 561 CACCTTCCCG TCCGTCCGGC AGTCCTCAGG CCTCTACTCG
 601 CTGAGCAGCG TGGTGAGCGT GACCTCAAGC AGCCAGCCCG
 641 TCACCTGCAA CGTGGCCCAC CCAGCCACCA ACACCAAAGT
 681 GGACAAGACC GTTGCGCCCT CGACATGCAG CAAGCCCACG
 721 TGCCCACCCC CTGAACTCCT GGGGGGACCG TCTGTCTTCA
 761 TCTTCCCCCC AAAACCCAAG GACACCCTCA TGATCTCACG
 801 CACCCCCGAG GTCACATGCG TGGTGGTGGA CGTGAGCCAG
 841 GATGACCCCG AGGTGCAGTT CACATGGTAC ATAAACAACG
 881 AGCAGGTGCG CACCGCCCGG CCGCCGCTAC GGGAGCAGCA
 921 GTTCAACAGC ACGATCCGCG TGGTCAGCAC CCTCCCCATC
 961 GCGCACCAGG ACTGGCTGAG GGGCAAGGAG TTCAAGTGCA
1001 AAGTCCACAA CAAGGCACTC CCGGCCCCCA TCGAGAAAAC
1041 CATCTCCAAA GCCAGAGGGC AGCCCCTGGA GCCGAAGGTC
1081 TACACCATGG GCCCTCCCCG GGAGGAGCTG AGCAGCAGGT
1121 CGGTCAGCCT GACCTGCATG ATCAACGGCT TCTACCCTTC
1162 CGACATCTCG GTGGAGTGGG AGAAGAACGG GAAGGCAGAG
1201 GACAACTACA AGACCACGCC GGCCGTGCTG GACAGCGACG
1241 GCTCCTACTT CCTCTACAAC AAGCTCTCAG TGCCCACGAG
1281 TGAGTGGCAG CGGGGCGACG TCTTCACCTG CTCCGTGATG
1321 CACGAGGCCT TGCACAACCA CTACACGCAG AAGTCCATCT
1361 CCCGCTCTCC GGGTAAA
```

Anti-Sense Nucleic Acids

Anti-sense nucleic acids can be used to inhibit the function of CD83. In general, the function of CD83 RNA is inhibited, for example, by administering to a mammal a nucleic acid that can inhibit the functioning of CD83 RNA. Nucleic acids that can inhibit the function of a CD83 RNA can be generated from coding and non-coding regions of the CD83 gene. However, nucleic acids that can inhibit the function of a CD83 RNA are often selected to be complementary to CD83 nucleic acids that are naturally expressed in the mammalian cell to be treated with the methods of the invention. In some embodiments, the nucleic acids that can inhibit CD83 RNA functions are complementary to CD83 sequences found near the 5' end of the CD83 coding region. For example, nucleic acids that can inhibit the function of a CD83 RNA can be complementary to the 5' region of SEQ ID NO:1, SEQ ID NO:3, SEQ ID NO:5 or SEQ ID NO:10.

A nucleic acid that can inhibit the functioning of a CD83 RNA need not be 100% complementary to SEQ ID NO:1, SEQ ID NO:3, SEQ ID NO:5 or SEQ ID NO:10. Instead, some variability the sequence of the nucleic acid that can inhibit the functioning of a CD83 RNA is permitted. For example, a nucleic acid that can inhibit the functioning of a CD83 RNA from a human can be complementary to a nucleic acid encoding either a human or a mouse CD83 gene product.

Moreover, nucleic acids that can hybridize under moderately or highly stringent hybridization conditions to a nucleic acid comprising SEQ ID NO:1, SEQ ID NO:3, SEQ ID NO:5 or SEQ ID NO:10 are sufficiently complementary to inhibit the functioning of a CD83 RNA and can be utilized in the methods of the invention.

"Stringent hybridization conditions" and "stringent hybridization wash conditions" in the context of nucleic acid hybridization are somewhat sequence dependent, and may differ depending upon the environmental conditions of the nucleic acid. For example, longer sequences tend to hybridize specifically at higher temperatures. An extensive guide to the hybridization of nucleic acids is found in Tijssen, Laboratory Techniques in Biochemistry and Molecular biology-Hybridization with Nucleic Acid Probes, page 1, chapter 2 "Overview of principles of hybridization and the strategy of nucleic acid probe assays" Elsevier, N.Y. (1993). See also, J. Sambrook et al., Molecular Cloning: A Laboratory Manual, Cold Spring Harbor Press, N.Y., pp 9.31-9.58 (1989); J. Sambrook et al., Molecular Cloning: A Laboratory Manual, Cold Spring Harbor Press, N.Y. (3rd ed. 2001).

Generally, highly stringent hybridization and wash conditions are selected to be about 5° C. lower than the thermal melting point ($T_m$) for the specific double-stranded sequence at a defined ionic strength and pH. For example, under "highly stringent conditions" or "highly stringent hybridization conditions" a nucleic acid will hybridize to its complement to a detectably greater degree than to other sequences (e.g., at least 2-fold over background). By controlling the stringency of the hybridization and/or washing conditions nucleic acids that are 100% complementary can be hybridized. For DNA-DNA hybrids, the $T_m$ can be approximated from the equation of Meinkoth and Wahl Anal. Biochem. 138:267-284 (1984):

$T_m$ 81.5° C.+16.6 (log M)+0.41 (% GC)−0.61 (% form)−500/L where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe.

Very stringent conditions are selected to be equal to the $T_m$ for a particular probe.

Alternatively, stringency conditions can be adjusted to allow some mismatching in sequences so that lower degrees of similarity can hybridize. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl and 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

The degree of complementarity or sequence identity of hybrids obtained during hybridization is typically a function of post-hybridization washes, the critical factors being the ionic strength and temperature of the final wash solution. The type and length of hybridizing nucleic acids also affects whether hybridization will occur and whether any hybrids formed will be stable under a given set of hybridization and wash conditions.

An example of stringent hybridization conditions for hybridization of complementary nucleic acids that have more than 100 complementary residues on a filter in a Southern or Northern blot is 50% formamide with 1 mg of heparin at 42° C., with the hybridization being carried out overnight. An example of highly stringent conditions is 0.15 M NaCl at 72° C. for about 15 minutes. An example of stringent wash conditions is a 0.2×SSC wash at 65° C. for 15 minutes (see also, Sambrook, infra). Often, a high stringency wash is preceded by a low stringency wash to remove background probe signal. An example of medium stringency for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C.

Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to detect and isolate homologous nucleic acids that are substantially identical to reference nucleic acids of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

In general, T$_m$ is reduced by about 1° C. for each 1% of mismatching. Thus, T$_m$, hybridization, and/or wash conditions can be adjusted to hybridize to sequences of the desired sequence identity. For example, if sequences with >90% identity are sought, the T$_m$ can be decreased 10° C. Generally, stringent conditions are selected to be about 5° C. lower than the thermal melting point (T$_m$) for the specific sequence and its complement at a defined ionic strength and pH. However, severely stringent conditions can utilize a hybridization and/or wash at 1, 2, 3, or 4° C. lower than the thermal melting point (T$_m$); moderately stringent conditions can utilize a hybridization and/or wash at 6, 7, 8, 9, or 10° C. lower than the thermal melting point (T$_m$); low stringency conditions can utilize a hybridization and/or wash at 11, 12, 13, 14, 15, or 20° C. lower than the thermal melting point (T$_m$).

If the desired degree of mismatching results in a T$_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology-Hybridization with Nucleic Acid Probes, Part 1, Chapter 2 (Elsevier, N.Y.); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.). Using these references and the teachings herein on the relationship between T$_m$, mismatch, and hybridization and wash conditions, those of ordinary skill can generate variants of the present homocysteine S-methyltransferase nucleic acids.

Precise complementarity is therefore not required for successful duplex formation between a nucleic acid that can inhibit a CD83 RNA and the complementary coding sequence of a CD83 RNA. Inhibitory nucleic acid molecules that comprise, for example, 2, 3, 4, or 5 or more stretches of contiguous nucleotides that are precisely complementary to a CD83 coding sequence, each separated by a stretch of contiguous nucleotides that are not complementary to adjacent CD83 coding sequences, can inhibit the function of CD83 RNA. In general, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an anti-sense nucleic acid hybridized to a sense nucleic acid to determine the degree of mismatching that will be tolerated between a particular anti-sense nucleic acid and a particular CD83 RNA.

Nucleic acids that complementary a CD83 RNA can be administered to a mammal or to directly to the site of the inappropriate immune system activity. Alternatively, nucleic acids that are complementary to a CD83 RNA can generated by transcription from an expression cassette that has been administered to a mammal. For example, a complementary RNA can be transcribed from a CD83 nucleic acid that has been inserted into an expression cassette in the 3' to 5' orientation, that is, opposite to the usual orientation employed to generate sense RNA transcripts. Hence, to generate a complementary RNA that can inhibit the function of an endogenous CD83 RNA, the promoter would be positioned to transcribe from a 3' site towards the 5' end of the CD83 coding region.

In some embodiments an RNA that can inhibit the function of an endogenous CD83 RNA is an anti-sense oligonucleotide. The anti-sense oligonucleotide is complementary to at least a portion of the coding sequence of a gene comprising SEQ ID NO:1, SEQ ID NO:3, SEQ ID NO:5 or SEQ ID NO:10. Such anti-sense oligonucleotides are generally at least six nucleotides in length, but can be about 8, 12, 15, 20, 25, 30, 35, 40, 45, or 50 nucleotides long. Longer oligonucleotides can also be used. CD83 anti-sense oligonucleotides can be provided in a DNA construct and introduced into cells whose division is to be decreased, for example, into CD4+ T cells, Th-1 cells, Th-2 cells or lymphocyte precursor cells.

Anti-sense oligonucleotides can be composed of deoxyribonucleotides, ribonucleotides, or a combination of both. Oligonucleotides can be synthesized endogenously from transgenic expression cassettes or vectors as described herein. Alternatively, such oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994, Meth. Mol. Biol. 20:1-8; Sonveaux, 1994, Meth. Mol. Biol. 26:1-72; Uhlmann et al., 1990, Chem. Rev. 90:543-583.

CD83 anti-sense oligonucleotides can be modified without affecting their ability to hybridize to a CD83 RNA. These modifications can be internal or at one or both ends of the anti-sense molecule. For example, internucleoside phosphate linkages can be modified by adding peptidyl, cholesteryl or diamine moieties with varying numbers of carbon residues between these moities and the terminal ribose. Modified bases and/or sugars, such as arabinose instead of ribose, or a 3',5'-substituted oligonucleotide in which the 3' hydroxyl group or the 5' phosphate group are substituted, can also be employed in a modified anti-sense oligonucleotide. These modified oligonucleotides can be prepared by methods available in the art. Agrawal et al., 1992, Trends Biotechnol. 10:152-158; Uhlmann et al., 1990, Chem. Rev. 90:543-584; Uhlmann et al., 1987, Tetrahedron. Lett. 215:3539-3542.

In one embodiment of the invention, expression of a CD83 gene is decreased using a ribozyme. A ribozyme is an RNA molecule with catalytic activity. See, e.g., Cech, 1987, Science 236: 1532-1539; Cech, 1990, Ann. Rev. Biochem. 59:543-568; Cech, 1992, Curr. Opin. Struct. Biol. 2: 605-609; Couture and Stinchcomb, 1996, Trends Genet. 12: 510-515. Ribozymes can be used to inhibit gene function by cleaving an RNA sequence, as is known in the art (see, e.g., Haseloff et al., U.S. Pat. No. 5,641,673).

CD83 nucleic acids complementary to SEQ ID NO:1, SEQ ID NO:3, SEQ ID NO:5 or SEQ ID NO:10 can be used to generate ribozymes that will specifically bind to mRNA transcribed from a CD83 gene. Methods of designing and constructing ribozymes that can cleave other RNA molecules in trans in a highly sequence specific manner have been developed and described in the art (see Haseloff et al. (1988), Nature 334:585-591). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201). The target sequence can be a segment of about 10, 12, 15, 20, or 50 contiguous nucleotides selected from a nucleotide sequence shown in SEQ ID NO:1, SEQ ID NO:3, SEQ ID NO:5 or SEQ ID NO:10. Longer complementary sequences can be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target.

Other CD83 Modulating Molecules

A wide variety of molecules may be used to modulate CD83 activity or function. Such molecules can also be used to modulate the immune system independent of CD83. Compositions and methods for modulating CD83 activity or expression can include these molecules as well as other components. Representative examples that are discussed in more detail below include transciption factors, RNA-binding factors, organic molecules, or peptides.

RNA-Binding Factors:

One class of molecules that can be used to modulate cytokine levels or GM-CSF levels by way of the CD83 gene is the RNA binding factors. Such factors include those described in PCT/EP01/14820 and other sources.

For example, the HuR protein (Genbank accession number U38175) has the ability to specifically bind to CD83 RNA at AU-rich elements or sites. Such AU-rich elements comprise sequences such as AUUUA (SEQ ID NO:49), AUUUUA (SEQ ID NO:50) and AUUUUUA (SEQ ID NO:51). Binding by such HuR proteins to CD83 mRNA is thought to increase the stability, transport and translation of CD83 mRNA, and thereby increase the expression of CD83 polypeptides. Hence, CD83 expression may be increase by administering HuR proteins or nucleic acids to a mammal.

Conversely, CD83 expression may be decreased by administering factors that block HuR binding to CD83 mRNA. Factors that block HuR binding include proteins or nucleic acids that can bind to the AU-rich elements normally bound by HuR, for example, nucleic acids or anti-sense nucleic acids that are complementary to AU-rich elements.

Organic Molecules:

Numerous organic molecules may be used to modulate the immune system. These compounds include any compound that can interact with a component of the immune system. Such compounds may interact directly with CD83, indirectly with CD83 or with some other polypeptide, cell or factor that plays a role in the function of the immune system. In some embodiments, the organic molecule can bind to a CD83 polypeptide or a CD83 nucleic acid.

Organic molecules can be tested or assayed for their ability to modulate CD83 activity, CD83 function or for their ability to modulate components of the immune system. For example, within one embodiment of the invention suitable organic molecules may be selected either from a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries," WO 95/16209; Lerner, R. et al., "Encoded combinatorial chemical libraries," WO 93/20242; Pavia, M. R. et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips, G. B. and G. P. Wei, "Solid-phase Synthesis of Benzimidazoles," *Tet. Letters* 37:4887-90, 1996; Ruhland, B. et al., "Solid-supported Combinatorial Synthesis of Structurally Diverse □□-Lactams," *J. Amer. Chem. Soc.* 111:2534, 1996; Look, G. C. et al., "The Indentification of Cyclooxygenase-1 Inhibitors from 4-Thiazolidinone Combinatorial Libraries," *Bioorg and Med. Chem. Letters* 6:707-12, 1996.

Peptides:

Peptide molecules that modulate the immune system may be obtained through the screening of combinatorial peptide libraries. Such libraries may either be prepared by one of skill in the art (see e.g. U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

Methods of Using the CD83 Mutant Mouse

In one embodiment, the invention provides a method for identifying ligands, receptors, therapeutic drugs and other molecules that can modulate the phenotype of the mutant CD83 in vivo. This method involves administering a test compound to the mutant CD83 mouse of the invention and observing whether the compound causes a change in the phenotype of the mutant mouse. Changes in phenotype that are of interest include increases or decreases in T cells (especially CD4+ T cells), increases or decreases in GMCSF, IL-2, IL-4 or IL-10 cytokine production, increases or decreases in inflammation, increases or decreases in dendritic cell function and other T cell responses known to one of skill in the art.

Test compounds can be screened in vitro to ascertain whether they interact directly with CD83. In vitro screening can, for example, identify whether a test compound or molecule can bind to the cytoplasmic tail or the membrane-associated portions of CD83. Such information, combined with observation of the in vivo phenotype before and after administration of the test compound provides further insight into the function of CD83 and provides targets for manipulation T cell activation and other functions modulated by CD83.

The invention is not limited to identification of molecules that directly associate with CD83. The in vivo screening methods provided herein can, also identify test compounds that have an indirect effect on CD83, or that partially or completely replace a function of CD83.

Increases or decreases in T cell numbers can be observed in blood samples or in samples obtained from thymus, spleen or lymph node tissues. In order to observe the activation of T cells and/or the interaction of T cells and dendritic cells, dendritic cells can be pulsed with antigens ex vivo and then injected into mice to prime CD4+ T cells in draining lymphoid organs. See Inaba et al., J. Exp. Med. 172: 631-640, 1990; Liu, et al., J. Exp. Med. 177: 1299-1307, 1993; Sornasse et al., J. Exp. Med. 175: 15-21, 1992. Antigens can also be deposited intramuscularly and dendritic cells from the corresponding afferent lymphatics can carry that antigen in a form stimulatory for T cells. Bujdoso et al., J. Exp. Med. 170: 1285-1302, 1989. According to the invention, factors stimulating the interaction of dendritic cells with T cells in vivo can be identified by administering antigens in this manner and then observing how T cell respond, e.g. by observing whether T cell activation occurs.

Increases or decreases in cytokine levels can be observed by methods provided herein or by other methods available in the art.

Compositions

The CD83 polypeptides and antibodies of the invention, including their salts, are administered so as to achieve a reduction in at least one symptom associated with an infection, indication or disease.

To achieve the desired effect(s), the polypeptide or antibody, a variant thereof or a combination thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the polypeptide or antibody chosen, the disease, the weight, the physical condition, the health, the age of the mammal, whether prevention or treatment is to be achieved, and if the polypeptide or antibody is chemically modified. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the CD83 polypeptides and antibodies of the invention may be essentially continuous over a preselected period of time or may be in a series of spaced doses. Both local and systemic administration is contemplated.

To prepare the composition, CD83 polypeptides and antibodies are synthesized or otherwise obtained, purified as necessary or desired and then lyophilized and stabilized. The polypeptide or antibody can then be adjusted to the appropriate concentration, and optionally combined with other agents. The absolute weight of a given polypeptide or antibody included in a unit dose can vary widely. For example, about 0.01 to about 2 g, or about 0.1 to about 500 mg, of at least one polypeptide or antibody of the invention, or a plurality of CD83 polypeptides and antibodies specific for a particular cell type can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the CD83 polypeptides or antibodies of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic CD83 polypeptides or antibodies of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic CD83 polypeptides or antibodies may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic CD83 polypeptides or antibodies of the invention are prepared for oral administration, they are generally combined with a pharmaceutically acceptable carrier, diluent or excipient to form a pharmaceutical formulation, or unit dosage form. For oral administration, the CD83 polypeptides or antibodies may be present as a powder, a granular formulation, a solution, a suspension, an emulsion or in a natural or synthetic polymer or resin for ingestion of the active ingredients from a chewing gum. The active CD83 polypeptides or antibodies may also be presented as a bolus, electuary or paste. Orally administered therapeutic CD83 polypeptides or antibodies of the invention can also be formulated for sustained release, e.g., the CD83 polypeptides or antibodies can be coated, micro-encapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic CD83 polypeptides or antibodies of the invention can be prepared by procedures known in the art using well-known and readily available ingredients. For example, the polypeptide or antibody can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the CD83 polypeptides or antibodies of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one polypeptide or antibody of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more CD83 polypeptides or antibodies of the invention are designed to resist disintegration in the stomach and dissolve in the more neutral to alkaline environment of the duodenum.

The therapeutic CD83 polypeptides or antibodies of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic CD83 polypeptides or antibodies of the invention can also take the form of an aqueous or anhydrous solution or dispersion, or alternatively the form of an emulsion or suspension or salve.

Thus, the therapeutic CD83 polypeptides or antibodies may be formulated for parenteral administration (e.g., by injection, for example, bolus injection or continuous infusion) and may be presented in unit dose form in ampules, pre-filled syringes, small volume infusion containers or in multi-dose containers. As noted above, preservatives can be added to help maintain the shelve life of the dosage form. The active CD83 polypeptides or antibodies and other ingredients may form suspensions, solutions, or emulsions in oily or aqueous vehicles, and may contain formulatory agents such as suspending, stabilizing and/or dispersing agents. Alternatively, the active CD83 polypeptides or antibodies and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Also contemplated are combination products that include one or more CD83 polypeptides or antibodies of the present invention and one or more other anti-microbial agents. For example, a variety of antibiotics can be included in the pharmaceutical compositions of the invention, such as aminoglycosides (e.g., streptomycin, gentamicin, sisomicin, tobramycin and amicacin), ansamycins (e.g. rifamycin), antimycotics (e.g. polyenes and benzofuran derivatives), β-lactams (e.g. penicillins and cephalosporins), chloramphenical (including thiamphenol and azidamphenicol), linosamides (lincomycin, clindamycin), macrolides (erythromycin, oleandomycin, spiramycin), polymyxins, bacitracins, tyrothycin, capreomycin, vancomycin, tetracyclines (including oxytetracycline, minocycline, doxycycline), phosphomycin and fusidic acid.

Additionally, the CD83 polypeptides or antibodies are well suited to formulation as sustained release dosage forms and the like. The formulations can be so constituted that they release the active polypeptide or antibody, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic CD83 polypeptides or antibodies of the invention can be delivered via patches or bandages for dermal administration. Alternatively, the polypeptide or antibody can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active CD83 polypeptides or antibodies can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic CD83 polypeptides or antibodies in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic polypeptide or antibody may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The CD83 polypeptides or antibodies of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newinan, S. P. in *Aerosols and the Lung*, Clarke, S. W. and Davia, D. eds., pp. 197-224, Butterworths, London, England, 1984).

Therapeutic CD83 polypeptides or antibodies of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the CD83 polypeptides or antibodies of the present invention specific for the indication or disease to be treated. Dry aerosol in the form of finely divided solid polypeptide or antibody or nucleic acid particles that are not dissolved or suspended in a liquid are also useful in the practice of the present invention. CD83 polypeptides or antibodies of the present invention may be formulated as dusting powders and comprise finely divided particles having an average particle size of between about 1 and 5 μm, alternatively between 2 and 3 μm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic CD83 polypeptides or antibodies of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

The present invention further pertains to a packaged pharmaceutical composition for controlling microbial infections such as a kit or other container. The kit or container holds a therapeutically effective amount of a pharmaceutical composition for controlling microbial infections and instructions for using the pharmaceutical composition for control of the microbial infection. The pharmaceutical composition includes at least one polypeptide or antibody of the present invention, in a therapeutically effective amount such that the selected disease or immunological condition is controlled.

The invention will be further described by reference to the following detailed examples, which are given for illustration of the invention, and are not intended to be limiting thereof.

EXAMPLE 1

Mouse Mutation and Characterization

Mutant Generation

Male C57BL6 mice received 3 weekly injections of N-ethyl-N-nitrosourea (ENU) at a concentration of 100 mg/kg. N-Ethyl-N-nitrosourea was quantified prior to injection by spectrophotometry. Mice that regained fertility after a minimum period of 12 weeks were then used to generate pedigree founder G1 animals. G1 male mice were crossed to C57BL6J females and their female progeny (G2 animals) crossed back to their fathers to generate G3 animals for screening.

G3 mice were weaned at 3 weeks of age. Each animal then underwent a series of screens designed to assess a number of parameters, including immune function, inflammatory response and bone development. In the initial screen, conducted at 6 weeks of age, 150-200 ul of whole blood was collected by retro-orbital bleed into heparinized tubes. Cells were pelleted and red blood cells lysed. Samples were then stained with antibodies to cell surface markers expressed on distinct lymphoid and myeloid sub-populations. These samples were analyzed by flow-cytometry.

Mutant Identification

A group of 27 G3 mice from 2 different pedigrees, pedigree 9 and pedigree 57 (i.e. derived from 2 distinct G1 fathers)

were analyzed in this screen. Two animals from pedigree 9 were identified as having a reduced (>2 standard deviation from normal) percentage of CD4+ T cells in peripheral blood (FIG. 1). Both animals were descended from the same G1 and shared the same mother. All other animals screened on that day had a normal percentage of CD4+ T cells. The number of phenodeviants identified (2 from a litter of 9 animals) was suggestive of a trait controlled by a single gene and inherited in a Mendelian fashion.

A second litter generated from Pedigree 9 bred to G2 daughter #4 exhibited an identical phenotype with reduced numbers of CD4+ T cells, further suggesting that the trait had a genetic basis. The phenotype was designated LCD4.1 (Low CD4 Mutant # 1) and was used for mapping experiments.

Mutation Mapping

In order to map the LCD4.1 mutant phenotype, affected G3 male mice (presumptive homozygous for the mutation) were bred to female animals from the C3HeB/FeJ strain to generate F1 progeny. These F1 females (presumptively heterozygous for the mutation) were then mated back to their affected father to generate N2 progeny.

Blood was collected from N2 animals and flow cytometric analysis was performed to identify CD4+ T cells. For a phenotype controlled by a single gene, breeding homozygous fathers to heterozygous daughters should yield 50% normal N2 animals and 50% affected N2 animals. This ratio of normal to affected animals was observed in the N2 generation: Multiple N2 animals exhibited a reduced percentage of CD4+ T cells, indicating that the phenotype was heritable (FIG. 2).

DNA samples were prepared from samples of tail tissue collected from these N2 mice and used for a genome scan, using a collection of assembled markers, and performed on the ABI 3100 DNA analyzer. Initial genetic linkage was seen to the tip of chromosome 13, where the closest microsatellite marker was D13Mit139 with a LOD score of 8.2. By calculating upper and lower confidence limits, the mutant gene was located between 13.4 and 29.6 cM on chromosome 13. Through additional genotyping, this region was reduced to an 11 cM interval on chromosome 13. No significant linkage to other chromosomal regions was seen.

Mutation Identification

A candidate gene, CD83, was identified for gene-testing based upon its reported position within the interval. CD83 has previously been used as a marker of dendritic cell activation, suggesting that it might play a role in dendritic cell function and hence in regulating T cell development and function.

Sequence analysis of the mutant DNA revealed a mutation in the stop codon of CD83. All affected animals were homozygous for this mutation while non-affected animals carried one wild-type allele and one mutant allele (FIG. 3 and FIG. 4). The mutation destroyed the stop codon and resulted in the addition of a unique 55 amino acid tail to the C-terminus of CD83 (FIG. 5).

Additional Functional Data

A reduction in CD4+ T cells was seen in peripheral blood, spleen tissues and lymph nodes from homozygous LCD4.1 mice. Although there was a reduced number of CD4+ T cells in the thymus there is no overt block in the developmental process and there was no alteration in B cell development in the bone marrow. Histological evaluation of thymus, spleen and lymph nodes from affected mice revealed no gross alteration in tissue architecture.

Dendritic cells can be differentiated from bone marrow of wild type mice by culture in GM-CSF. These cells can be characterized by the surface expression of dendritic cell markers, including CD86 and CD11c. Both LCD4.1 affected and normal animals were capable of giving rise to CD86+ CD11c+ cells under these culture conditions. LCD4.1 mutant mice thus were capable of generating dendritic cells under in vitro culture conditions. These data suggest that the phenotype seen in LCD4.1 mice is not due to a failure of dendritic cells to develop but rather may reflect a defect in function.

To track dendritic cells the sensitizing agent FITC was applied to the dorsal surface of the ears of LCD4.1 affected and wild-type mice. FITC was picked up by dendritic cells that then migrated to the draining auricular lymph nodes, where the presence of the FITC label on the dendritic cell surface permitted detection by flow-cytometry. FITC labeled cells expressing CD86 were detected in equal proportions in draining lymph node from normal and affected LCD4.1 mice. These data indicate that LCD4.1 mutant animals are capable of generating dendritic cells in vivo and that these cells are able to pick up antigen in the ear and travel to the draining lymph node.

EXAMPLE 2

CD83 and CD4+ T Cell Function

Materials and Methods

Spleens were removed from wild type and mutant mice and digested with collagenase to liberate dendritic cells. Spleens were stained for surface expression of CD4 (helper T cells) and CD11c (dendritic cells). Cells expressing these markers were purified by fluorescence activated cell sorting (FACS sorting). CD11c and CD4+ positive cells were also purified from an allogeneic mouse strain, BALBc.

Mixed lymphocyte cultures were set up using purified cell populations. Dendritic cells from BALBc animals were used to stimulate CD4+ T cells from wild type and mutant mice. In a reciprocal experiment dendritic cells prepared from wild type and mutant mice were used to stimulate BALBc CD4+ T cells. After 5 days in culture proliferative responses were measured by incorporation of tritiated thymidine.

Figure 6A:
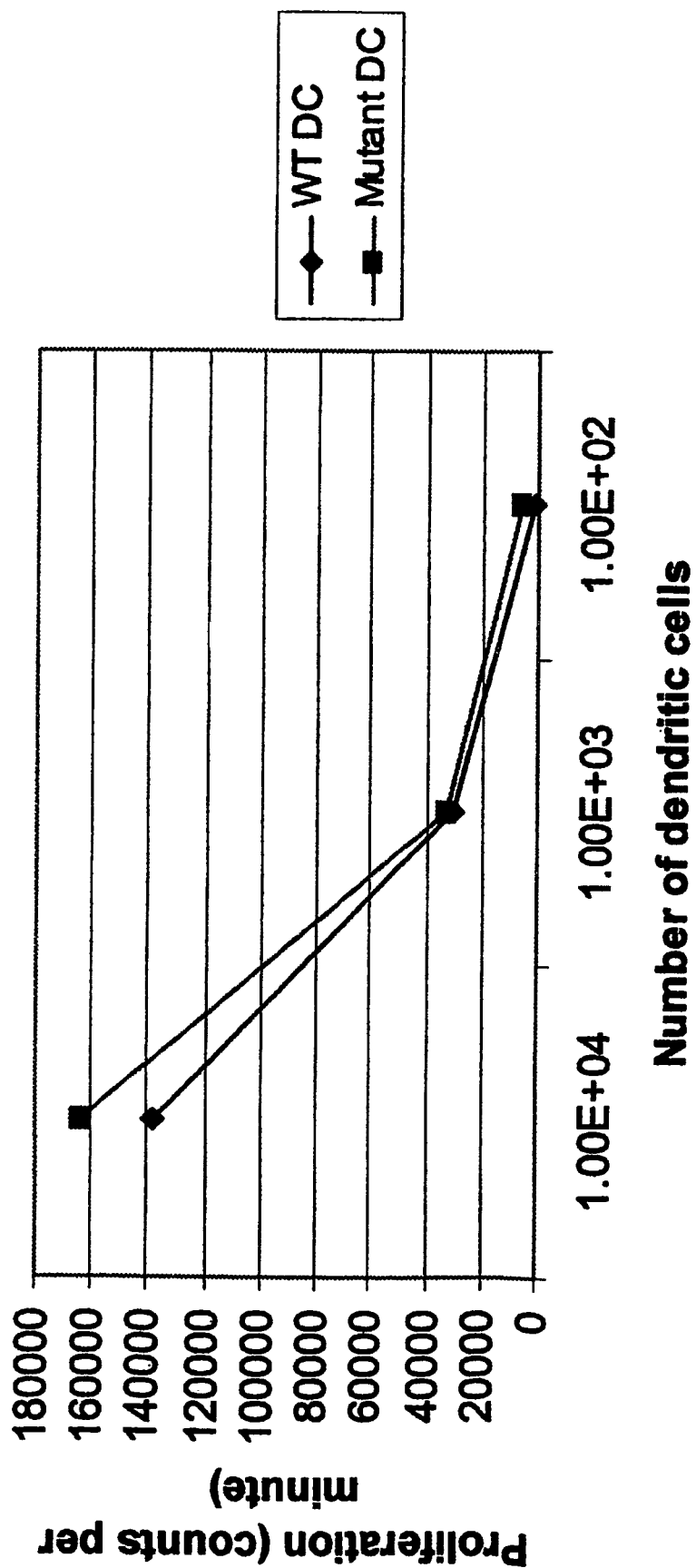
FIG. 6A illustrates that dendritic cells from wild type (♦, WT DC) and mutant (■, mutant DC) mice are capable of the allogeneic activation of CD4+ T cells. CD4+ T cells were stimulated with 10,000, 1000 or 100 dendritic cells for 5 days and proliferation measured by incorporation of tritiated thymidine.
Figure 6B:
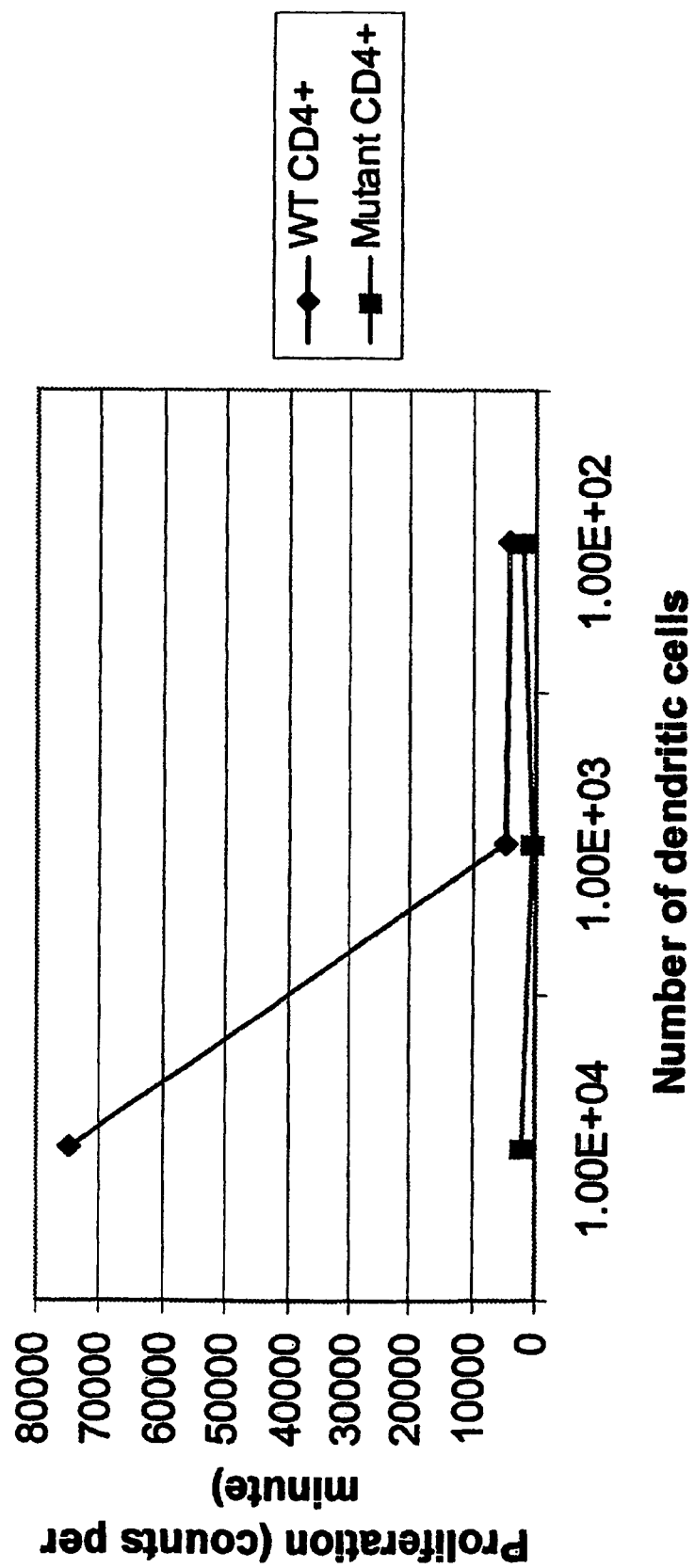
FIG. 6B illustrates that CD4+ T cells from mutant mice (■, mutant CD4) fail to respond to allogeneic stimulation with BALBc dendritic cells, although wild type animals (♦, WT CD4+) respond normally. CD4+ T cells were stimulated with 10,000, 1000 or 100 dendritic cells for 5 days and proliferation measured by incorporation of tritiated thymidine.

Dendritic cells from wild type and mutant mice were both capable of activating allogeneic T cells, suggesting that dendritic cell function was unimpaired in the mutant animal (FIG. 6a). In contrast CD4+ T cells from mutant animals exhibited a diminished response after 5 days of stimulation (FIG. 6b).

These data suggest that the mutation in the CD83 gene has minimal effect on dendritic cells intrinsic function but rather has a profound effect upon T cell activity. The CD4+ T cell therefore may have a novel requirement for CD83 functionality on T cells during allogeneic activation. CD83 may be influencing the extent of CD4+ T cell activation or altering the duration of the CD4+ T cell proliferative response. The therapeutic manipulation of CD83 may thus represent a mechanism for the specific regulation of T cell function in the treatment of T cell mediated diseases, including autoimmune disorders. Antibodies capable of blocking CD83 function may be used as therapeutics in the treatment of immune diseases whilst the activation of CD83 may have utility in enhancing immune responses in cancer and other circumstances.

Conclusion

Although CD83 has been described as a marker of dendritic cell activation there is little data as to its function in vivo. The mutation provided by the invention destabilizes or inactivates the protein and leads to impaired surface expression. As a consequence, CD4+ T cell function is impaired although the development of dendritic cells is not inhibited and mutant dendritic cells retain functionality. This results in the impaired development of CD4+ T cells. This impaired ability to activate T cells is also seen in a slight decrease in contact sensitivity responses in LCD4.1 mutant mice.

EXAMPLE 3

Mutant CD83 Have Different Cytokine Levels than Wild Type Mice

This Example demonstrates that CD4+ T-cells from CD83 mutant animals express higher levels of IL-4 and lower levels of IL-2 compared to CD4+ T-cells from CD83 wild type animals.

Methods for Cell Activation and Cytokine Measurements:

Spleens cells from 6-8-week-old homozygous CD83 wild type or CD83 mutant (LCD4.1) mice were used to isolate CD4+ T-cells by positive selection using magnetic beads (Miltenyi Biotec). A 96 round bottom plate was coated with 50 µL per well of a solution containing either 1 or 10 µg/mL of anti-CD3 and 0.1 or 0.2 µg/mL of anti-CD28 antibodies (both from Pharmingen) in PBS overnight. This plate was then washed using 150 µL of PBS three times. To this precoated plate, 20,000 CD4+ T-cells (either wild type or CD83 mutant) were added in a 200 µL final volume of RPMI containing 10% FBS, 55 µM β-mercaptoethanol and antibiotics. The plates were then incubated in a $CO_2$ incubator at 37° C. for 44 to 72 hours. For determination of cytokine levels, supernatants were harvested and cytokines were measured using either a Cytometric Bead Array system (Pharmingen) or ELISA (R&D). For RNA measurements, the cells were harvested and RNA was isolated using Tri reagent (Sigma). IL-10 and IL-4 mRNA levels were measured by reverse transcription and TaqMan (Applied Biosystems) analysis.

Figure 7:
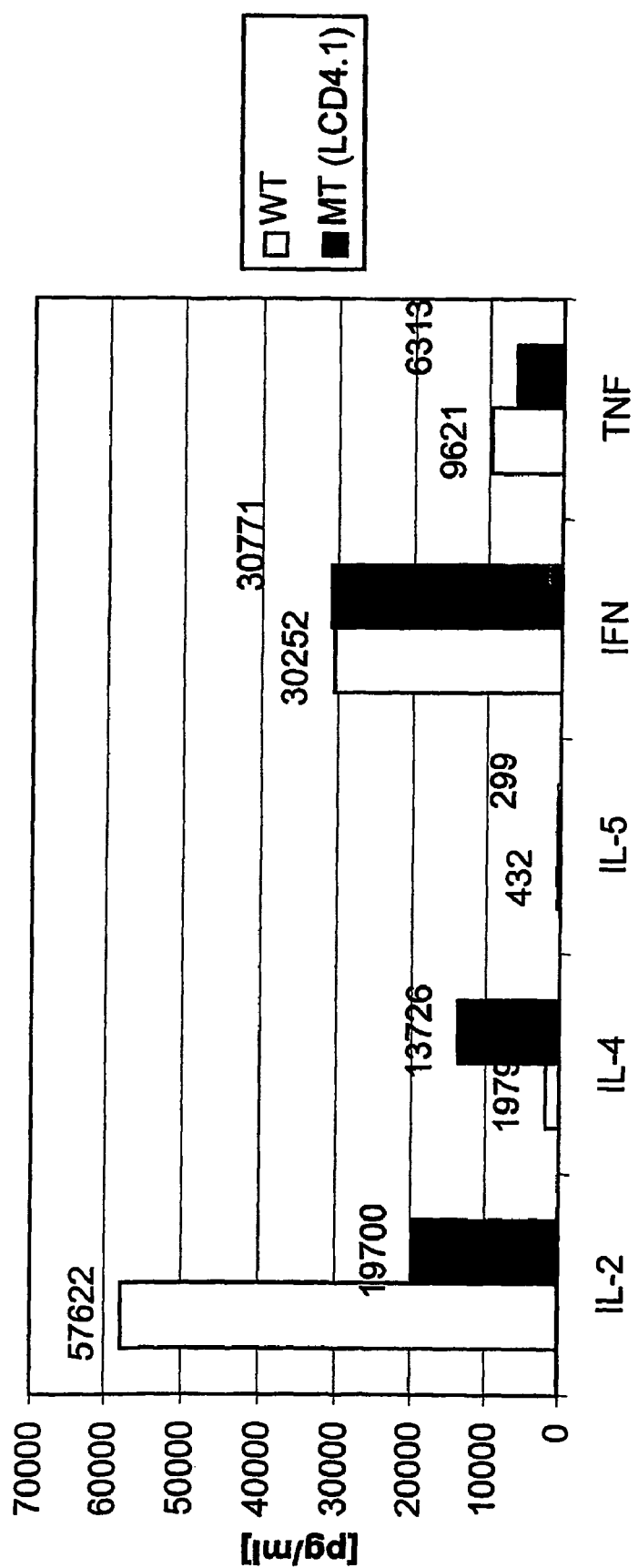
FIG. 7 provides a bar graph illustrating IL-2, IL-4, IL-5, TNFα, and IFNγ production from wild type CD4+ T cells (white bar) or CD83 mutant CD4+ T cells (dark bar) that had been stimulated with 1 μg/ml of anti-CD3 antibodies and 0.2 μg/ml of anti-CD28 antibodies for 72 hours. As illustrated, IL-2 levels are lower, and IL-4 levels are higher in the CD83 mutant T cells.

Results:

FIG. 7 shows the IL-2, IL-4, IL-5, TNFα and IFN-γ levels produced by either wild type or CD83 mutant CD4+ T-cells. Purified cells were incubated as described above in the presence of 1 µg/mL of anti-CD3 and 0.2 µg/mL of anti-CD28 antibodies for 72 hours. The supernatants were then simultaneously analyzed for production of IL-2, IL-4, IL-5, TNFα and IFN-γ using the cytometric bead array system from Pharmingen.

Figure 8:
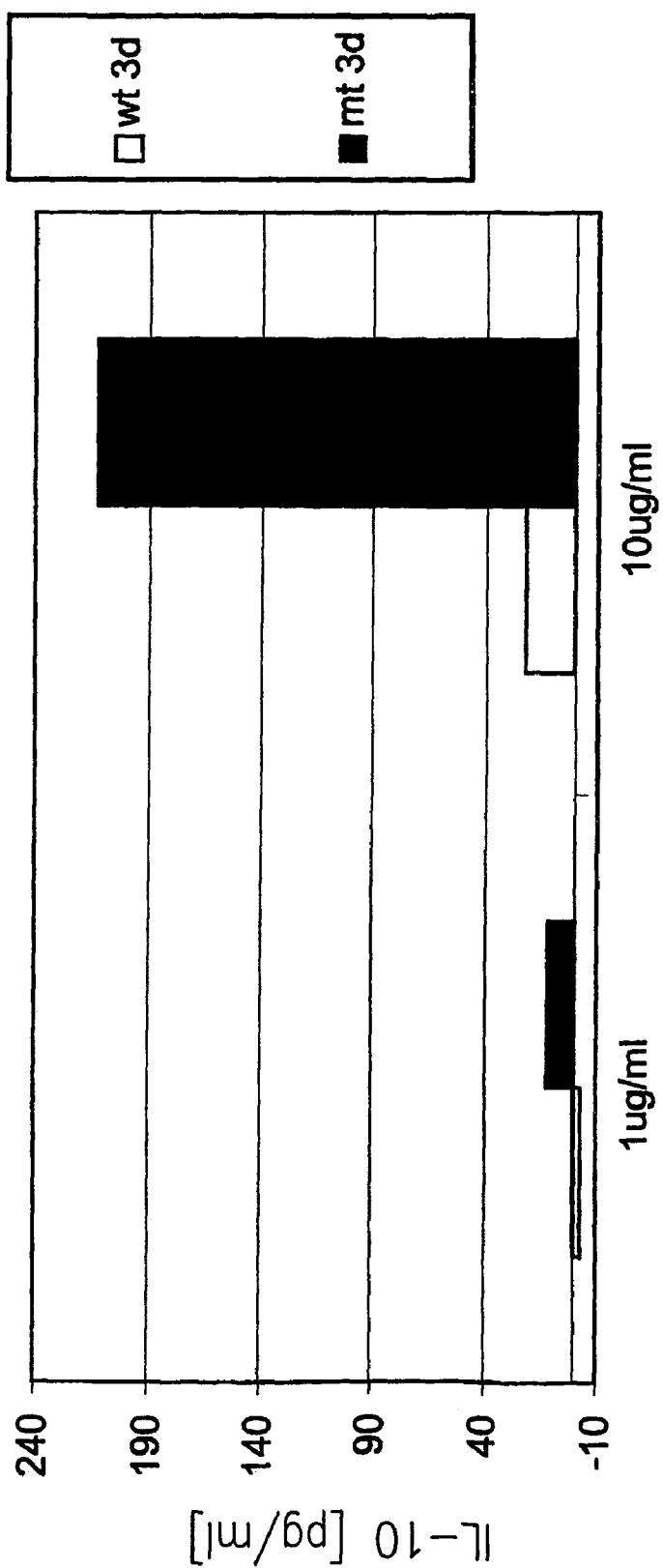
FIG. 8 provides a bar graph illustrating IL-10 production from wild type CD4+ T cells (white bar) or CD83 mutant CD4+ T cells (dark bar) that had been stimulated with 0.1 μg/ml of anti-CD28 antibodies and 1 to 10 μg/ml of anti-CD3 antibodies for 72 hours. As illustrated, IL-10 levels are higher in the CD83 mutant T cells.
Figure 9:
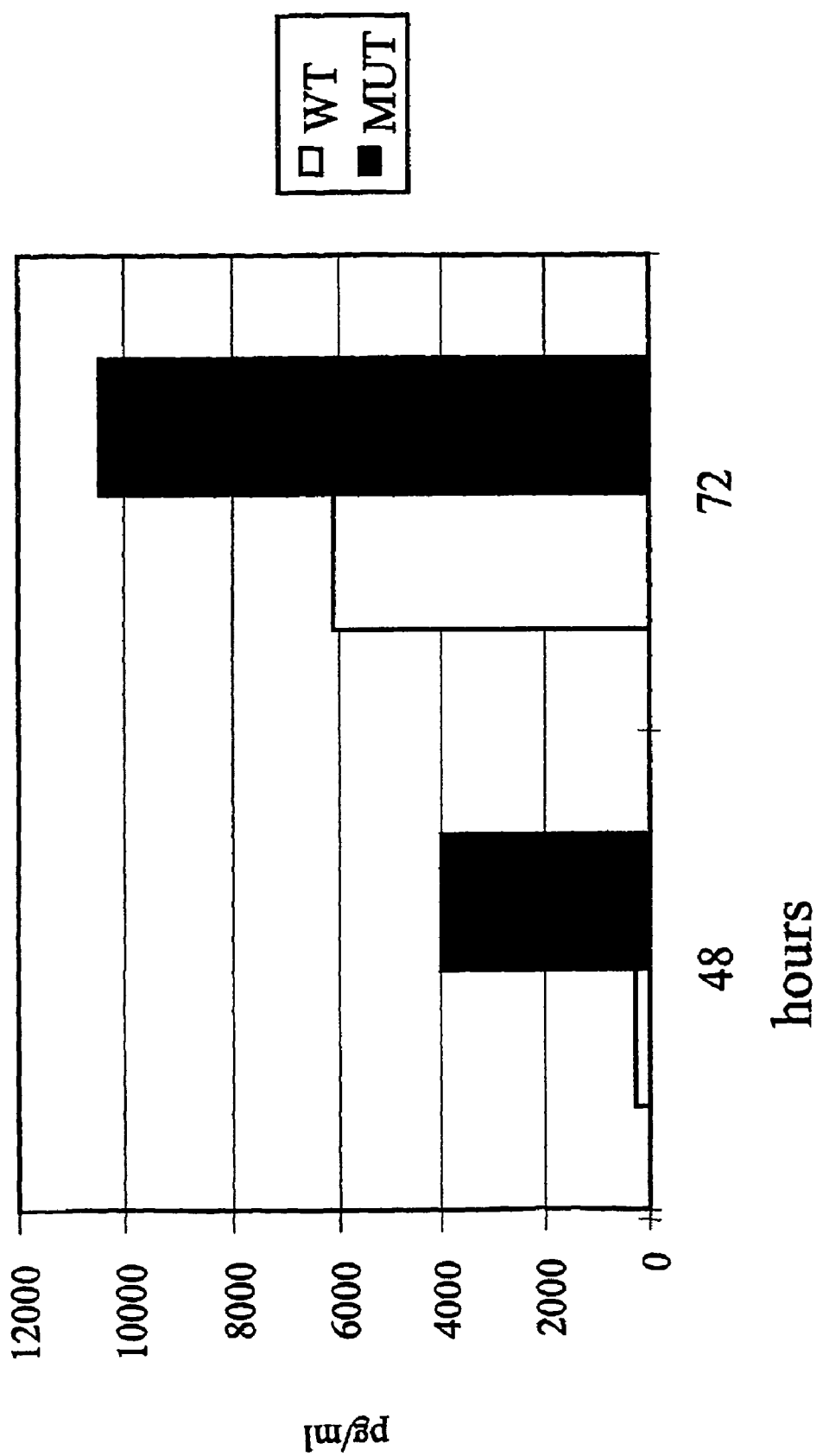
FIG. 9 provides a bar graph illustrating GM-CSF production from wild type CD4+ T cells (white bar) or CD83 mutant CD4+ T cells (dark bar) that had been stimulated with anti-CD3 and anti-CD28 antibodies. As illustrated, GM-CSF production is higher in the CD83 mutant cells than in wild type cells.
Figure 10B:
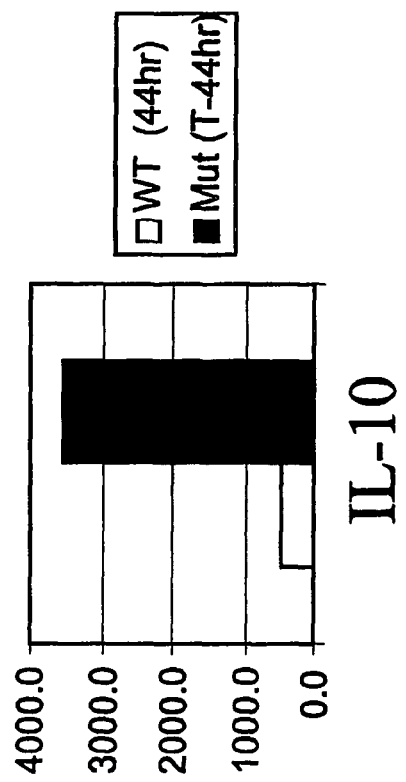
FIG. 10B provides a bar graph illustrating IL-10 mRNA levels from wild type CD4+ T cells (white bar) or CD83 mutant CD4+ T cells (dark bar) that had been stimulated with anti-CD3 and anti-CD28 antibodies. As illustrated, the IL-10 mRNA levels are higher in the CD83 mutant cells.
Figure 10A:
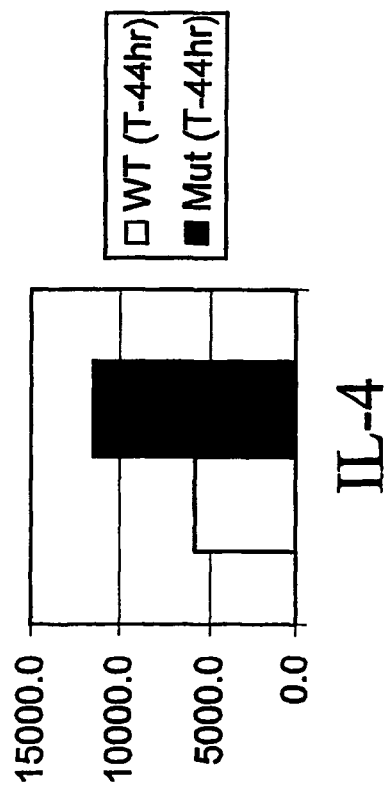
FIG. 10A provides a bar graph illustrating IL-4 mRNA levels from wild type CD4+ T cells (white bar) or CD83 mutant CD4+ T cells (dark bar) that had been stimulated with anti-CD3 and anti-CD28 antibodies. As illustrated, the IL-4 mRNA levels are higher in the CD83 mutant cells.

FIG. 7 demonstrates that CD4+ T-cells from CD83 mutant animals expressed higher levels of IL-4 and lower levels of IL-2 compared to CD4+ T-cells from CD83 wild type animals. Other cytokines and a new set of stimulation assays were analyzed including the production levels of IL-10 and GMCSF by these cells (FIGS. 8 and 9). In both cases, cells from mutant animals produce larger amounts of IL-10 and GMCSF than did wild type animals. FIG. 10 shows that mRNA levels for both IL-4 and IL-10 were increased in cells from activated mutant CD83, CD4+ T-cells compared with cells from wild type animals.

EXAMPLE 4

Anti-CD83 Antibodies May Mimic the Effects of the CD83 Mutation

Methods for Antibody Testing:

For modulation of cytokine production by anti-CD83 antibodies, CD4+ T-cells were isolated and activated as mentioned above in the presence of increasing concentrations of anti-CD83 antibodies. For proliferation assays, CD4+ T-cells were isolated from an OT2tg [transgenic mice with a T-cell receptor specific for chicken ovalbumin (OVA) 323-339 peptide]. Dendritic cells were isolated from a C57BL6 mouse by a negative selection using B220 magnetic beads (Miltenyi Biotec) followed by positive selection using CD11-c magnetic beads (Milteny Biotec). Five thousand CD4+ T-cells were then mixed with five thousand dendritic cells in a 96 well plate in the presences of 1 µM OVA peptide using RPMI (55 µM BME, 10% FBS plus antibiotics) in a final 200 uL volume. These cells were then incubated for 48 to 72 hours in a $CO_2$ incubator at 37° C. and pulsed using [$^3$H] thymidine for 8 hours. Cells were then harvested and [$^3$H] thymidine incorporation was quantified using a top counter.

Figure 11:
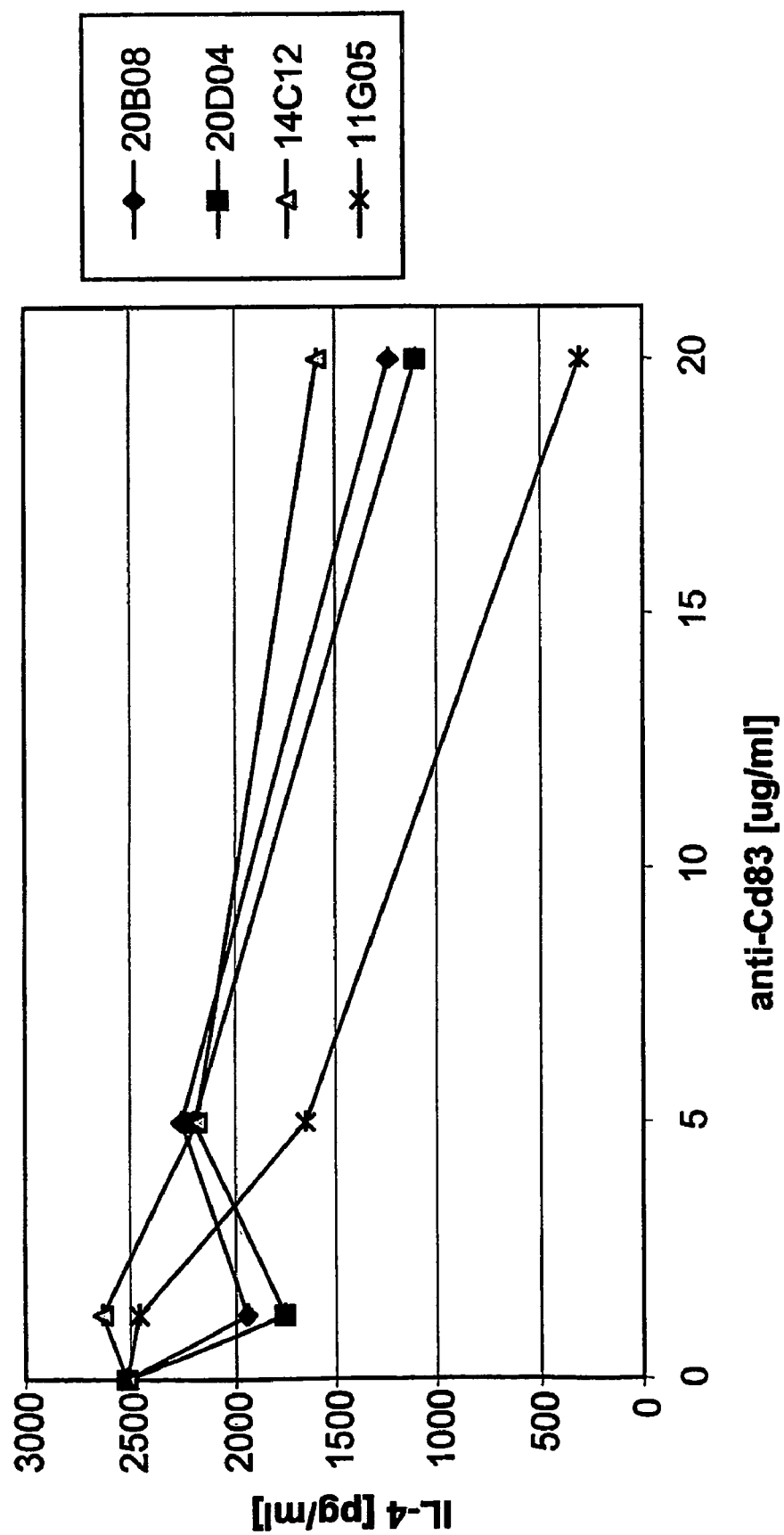
FIG. 11 provides a graph illustrating that various preparations of anti-CD83 antibodies inhibit IL-4 production in anti-CD3 and anti-CD28 antibody stimulated T cells. The amount of IL-4 produced by T cells in pg/ml is plotted versus the concentration of different anti-CD83 antibody preparations, including the 20B08 (♦) anti-CD83 preparation, the 20D04 (■) anti-CD83 preparation, the 14C12 (▲) anti-CD83 preparation and the 11G05 (X) anti-CD83 antibody preparation.

Results:

In some assays, anti-CD83 antibodies decreased production of IL-4 by activated CD4+ T-cells in a dose dependent manner. Different antibody preparations did provide somewhat different degrees of inhibition of IL-4 production (FIG. 11). Accordingly, the epitope and/or degree of affinity of the antibodies for the CD83 antigen may influence whether or not IL-4 production is significantly inhibited.

Figure 12:
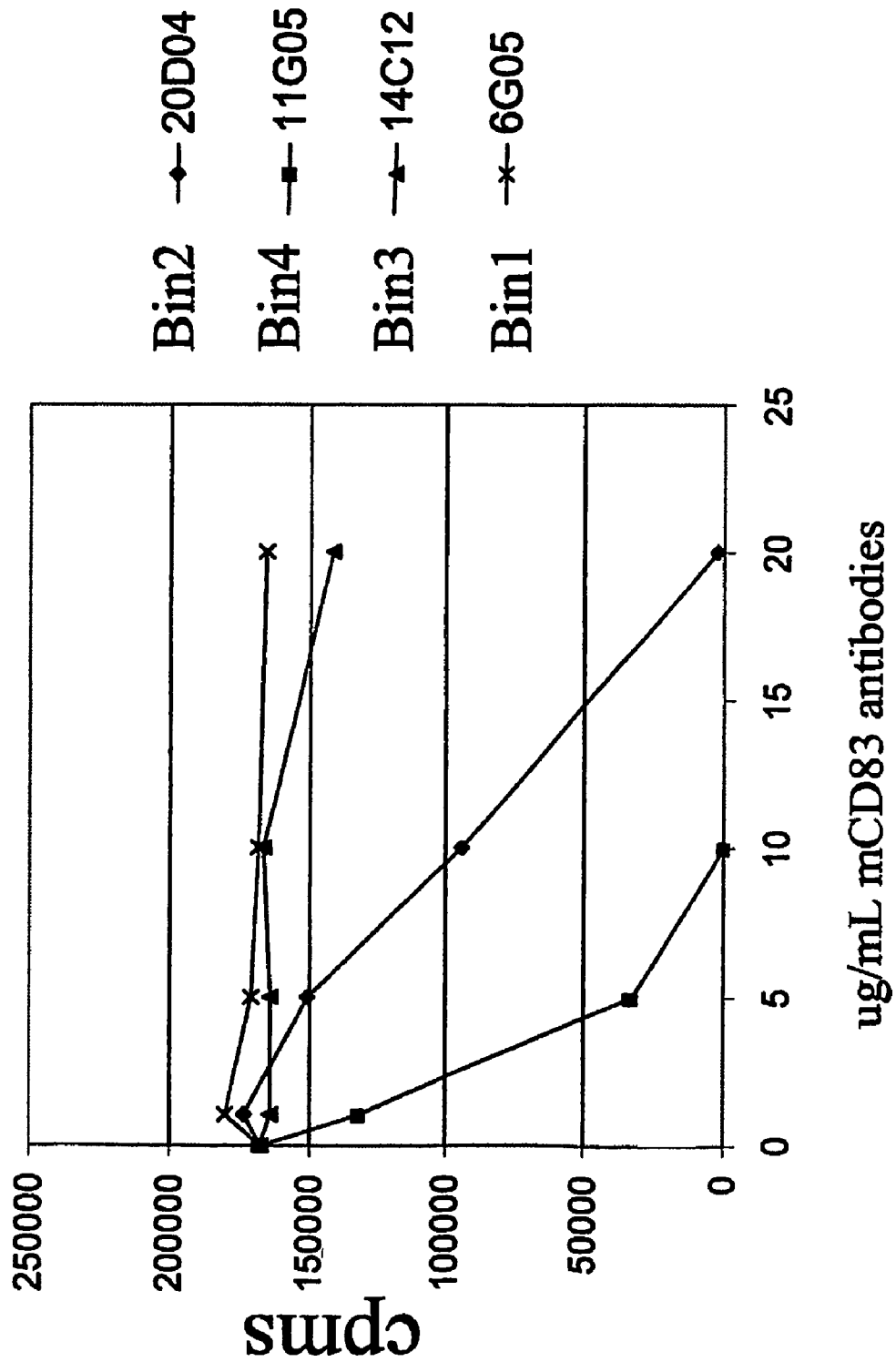
FIG. 12 provides a graph illustrating that various preparations of anti-CD83 antibodies inhibit T cell proliferation. The graph plots the incorporation of radioactive thymidine in cpms, which was used as an indicator of the amount of T cell proliferation, versus the concentration of the different anti-CD83 antibody preparations, including the 20D04 (♦) anti-CD83 preparation, the 11G05 (■) anti-CD83 antibody preparation, the 14C12 (♦) anti-CD83 preparation and the 6G05 anti-CD83 preparation (X).

The effects of anti CD83 antibodies on proliferation of a peptide specific T-cell proliferation assay using the OT2 T-cell receptor (TCR) transgenic system were also observed. CD4+ T-cells derived from these TCR transgenic animals express high levels of a T-cell receptor specific for chicken ovalbumin (OVA) 323-339 peptide and thus have high levels of proliferation when mixed with antigen presenting cells (dendritic cells were used) in the presence of the OVA peptide. In such assays, anti-CD83 antibodies were able to decrease proliferation of CD4+ T-cells in this system (FIG. 12). However, different antibody preparations had somewhat different effects on the proliferation of CD4+ T-cells. Accordingly, the CD83 epitope and/or degree of affinity of the antibodies for the CD83 antigen may influence whether or not CD4+ T-cell proliferation is significantly inhibited.

EXAMPLE 5

Increased T-Cell Proliferation by Transgenic Expression of CD83

This Example illustrates that over expression of CD83 in transgenic mice leads to increased T-cell proliferation.

Materials and Methods

A 34.3 kb fragment of normal mouse genomic DNA, including the ~18 kb coding region of the CD83 gene, as well as ~10.6 kb of upstream flanking sequences and ~5.7 kb of downstream sequences was microinjected into normal mouse one-cell embryos. Four individual founder animals were generated. Transgenic mice were then crossed to a male OT2tg mouse. Male offspring carrying both the CD83 and OT2 transgene were used to analyze peptide specific T-cell proliferation.

For proliferation assays, CD4+ T-cells and dendritic cells were isolated to from either OT2tg [transgenic mice with a T-cell receptor specific for chicken ovalbumin (OVA) 323-339 peptide] CD83 wild type or from OT2tg CD83 transgenic mice as described above (Example 4). Five thousand O2tg CD4+ T-cells from either wild type or CD83 transgenic animals were then mixed with five thousand wild type dendritic cells or five thousand CD83 transgenic dendritic cells in a 96 well plate in the presence of increasing concentrations of OVA peptide using RPMI (55 µM BME, 10% FBS plus antibiotics) in a final 200 uL volume. These cells were then incubated for 48 to 72 hours in a $CO_2$ incubator at 37C and pulsed using [$^3$H] thymidine for 8 hours. Cells were then harvested and [$^3$H] thymidine incorporation was quantified using a top counter.

Figure 13:
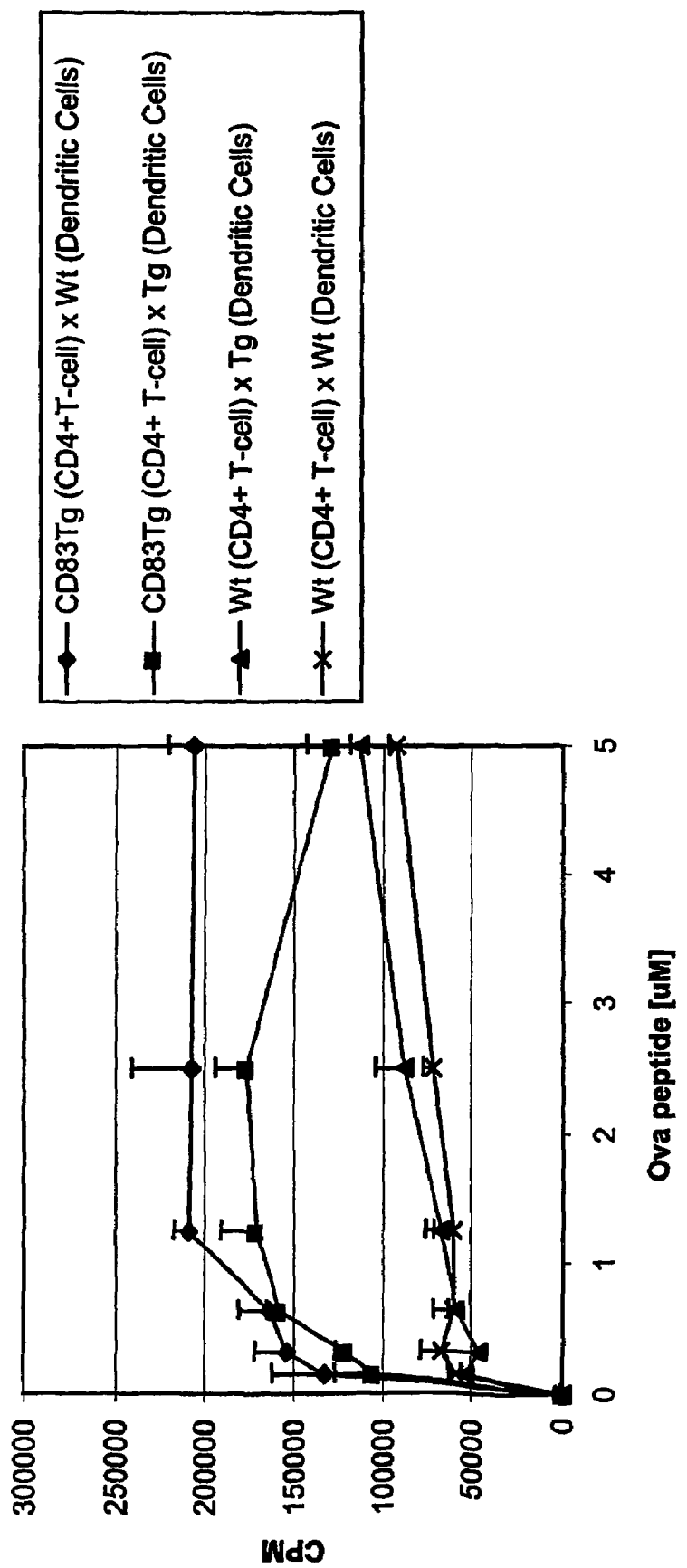
FIG. 13 provides a graph illustrating that transgenic mice that over-express wild type CD83 have increased T cell proliferation. The graph plots the incorporation of radioactive thymidine in cpms, which was used as an indicator of the amount of T cell proliferation, versus the concentration of OVA peptide. The transgenic mice utilized had a T-cell receptor specific for chicken ovalbumin (OVA) 323-339 peptide that can activate T-cells. When mixed with either transgenic or wild type dendritic cells in the presence of OVA peptide, transgenic CD4+ T cells had increased T-cell proliferation. However, transgenic dendritic cells could not substantially increase wild type CD4+ T cell proliferation. Transgenic CD83 CD4+ T cells mixed with wild type dendritic cells (♦); transgenic CD83 CD4+ T cells mixed with transgenic dendritic cells (■); wild type CD4+ T cells mixed with transgenic dendritic cells (▲); and wild type CD4+ T cells mixed with wild type dendritic cells (X).

Results:

OT2tg CD4$^+$ T-cells derived from CD83 transgenic mice proliferated at higher rates than the same cell population derived from a CD83 wild type animal (FIG. 13). This increased proliferation was seen at all the concentrations of OVA peptide tested. Whereas OT2tg CD4$^+$ T-cells derived from CD83 transgenic animals exhibited increased proliferation, dendritic cells from CD83 transgenic animals did not exhibit a substantial increase in proliferation. Therefore, it appears that transgenic expression in the CD4$^+$ T-cell, and not in dendritic cells is what led to the increased proliferation of CD4$^+$ T-cells.

EXAMPLE 6

Inhibition of Proliferation of PHA Activated Human PBMCs by Protein A Purified Rabbit Anti Mouse CD83 Polyclonal Sera This Example shows that antibodies raised against the mouse CD83 protein can inhibit proliferation of human peripheral blood mononuclear cells.

Materials and Methods

Figure 14:
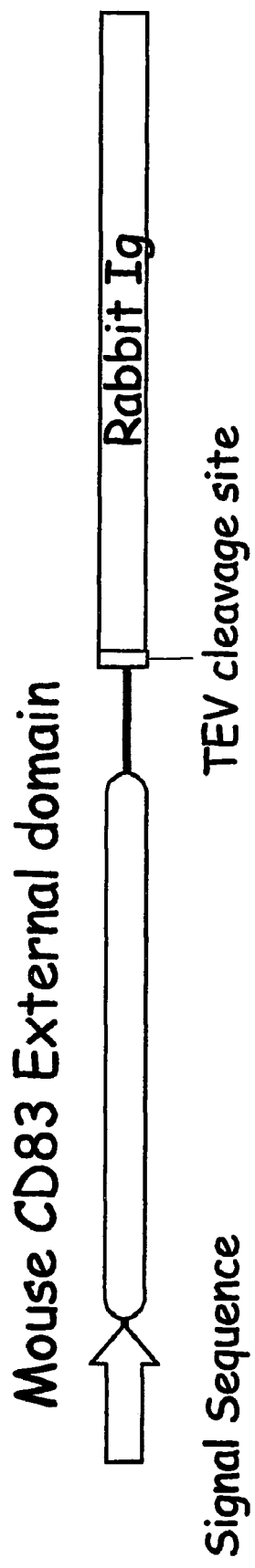
FIG. 14 provides a schematic diagram of the structural elements included in the mouse CD83 protein used for generating antibodies.
Figure 15:
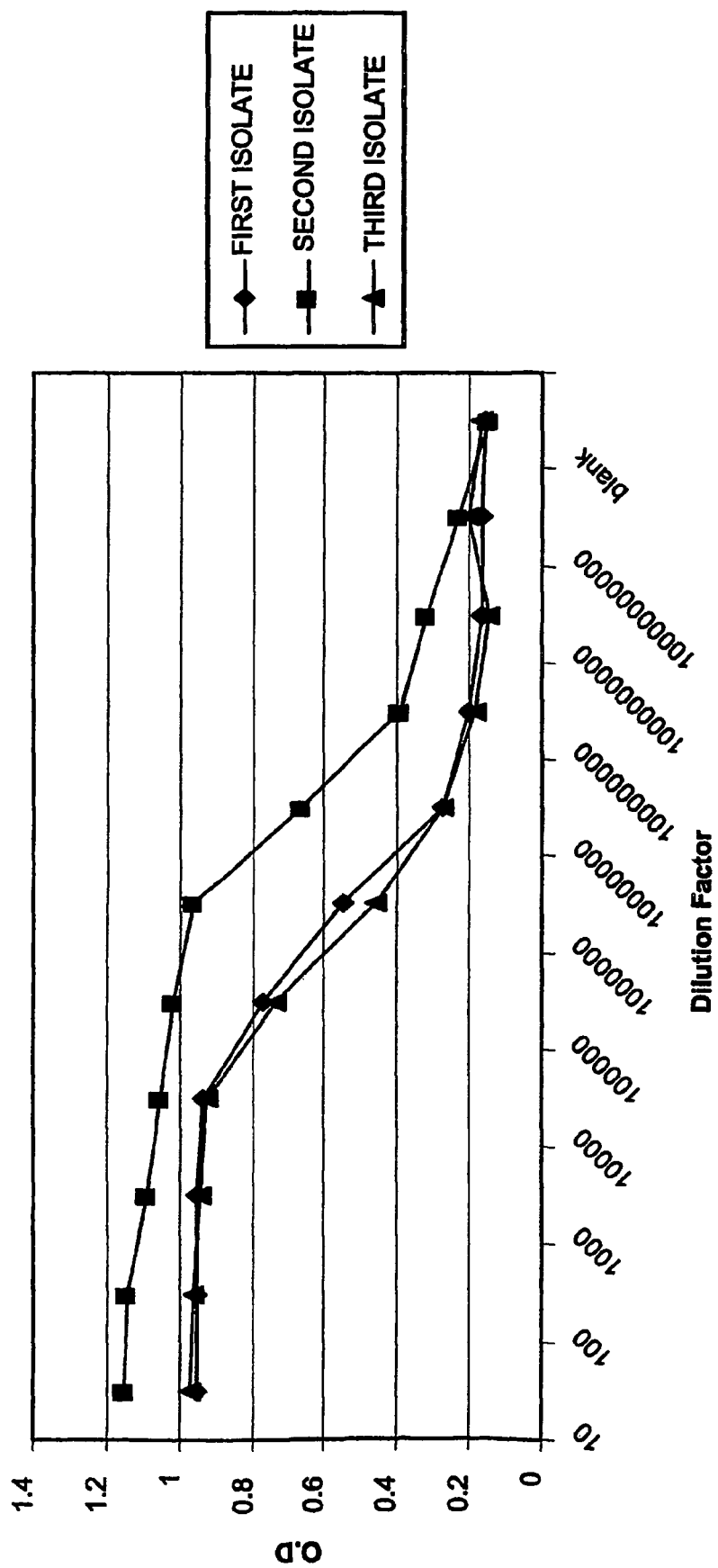
FIG. 15 provides a graph of ELISA data illustrating the titer obtained for different isolates of polyclonal anti-CD83 anti-sera. The first (♦), second (■) and third (▲) isolates had similar titers, though the titer of the second isolate (■) was somewhat higher.

Rabbit polyclonal sera was raised against mouse CD83 protein by immunizing rabbits using a mouse CD83 external domain protein fused to a rabbit Ig domain (FIG. 14). Pre-immune sera and anti-mouse polyclonal sera were then purified using a protein A column (Pharmacia Biotech) as described by the manufacturer, then dialyzed against PBS and stored at 4° C. To monitor the recognition of mouse CD83 protein by the polyclonal sera, which was obtained at different dates post immunization, a titer was obtained using an antigen specific ELISA (FIG. 15). As illustrated by FIG. 15, a good polyclonal response was obtained against the mouse CD83 protein.

Human peripheral blood mononuclear cells (PBMCs) were isolated using a Ficoll gradient (Ficoll Paque Plus, Pharmacia) and washed with PBS buffer. For activation and proliferation studies, five thousand cells were incubated in 200 µL of media (RPMI, 10% FBS, antibiotics) and 5 ug/mL of *Phaseolus vulgaris* leucoagglutinin (PHA) in the presence or absence of increasing concentrations of Protein A purified pre-immune sera or with similarly purified anti-CD83 polyclonal antibodies. After 48 hours at 37° C. in a $CO_2$ incubator the cells were pulsed with [$^3$H] thymidine for ~8 hours and harvested. Thymidine incorporation into the PBMCs was measured using a top counter for analysis.

Results

Figure 16:
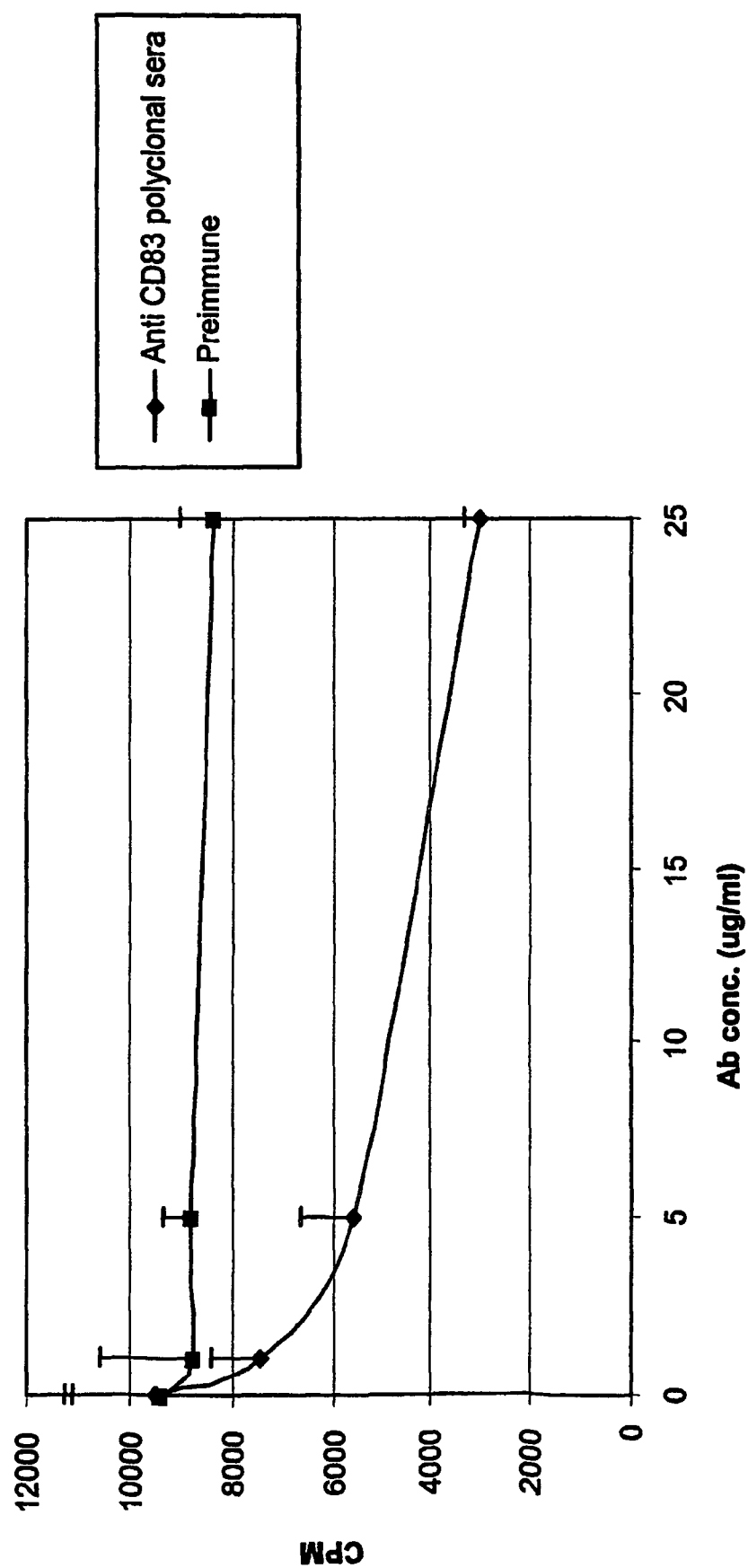
FIG. 16 illustrates that proliferation of PHA-activated human PBMCs was inhibited by antibodies raised against the external region of the mouse CD83 protein (♦). Pre-immune serum (■) had little effect on the proliferation of human PBMCs.

FIG. 16 illustrates that proliferation of PHA-activated human PBMCs was inhibited by antibodies raised against the external region of the mouse CD83 protein. Proliferation of PHA-activated human PBMCs was not affected by addition of increasing concentrations of protein A purified rabbit pre-immune sera. When increasing concentrations of protein A purified rabbit polyclonal sera raised against the mouse CD83 protein was added, a concentration dependent decrease in proliferation was observed.

These data indicate that antibodies raised against the mouse protein are able to cross-react with the human protein. Moreover, antibodies raised against the mouse protein are able to inhibit proliferation of PHA-activated human PBMCs.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An antibody that can bind to a CD83 polypeptide of SEQ ID NO:9, wherein activated CD4+ T-cells produce lower levels of interleukin-4 when said T-cells are contacted with the antibody, wherein said antibody comprises a light chain and a heavy chain, and wherein the antibody comprises a light chain sequence set forth in SEQ ID NO:58.

2. An antibody that can bind to a CD83 polypeptide of SEQ ID NO:9, wherein CD4+ T-cell proliferation is decreased when said T-cells are contacted with the antibody, wherein said antibody comprises a light chain and a heavy chain, and wherein the antibody comprises a light chain sequence set forth in SEQ ID NO:58.

3. The antibody of claim 1, wherein the heavy chain variable region CDR1 of the antibody comprises the sequence SYDMT (SEQ ID NO:23).

4. An antibody that can bind to a CD83 polypeptide of SEQ ID NO:9, wherein activated CD4+ T-cells produce lower levels of interleukin-4 when said T-cells are contacted with the antibody, wherein said antibody comprises a light chain and a heavy chain, and wherein the antibody comprises the heavy chain sequence set forth in SEQ ID NO:60.

5. An antibody that can bind to a CD83 polypeptide of SEQ ID NO:9, wherein CD4+ T-cell proliferation is decreased when said T-cells are contacted with the antibody, wherein said antibody comprises a light chain and a heavy chain, and wherein the antibody comprises the heavy chain sequence set forth in SEQ ID NO:60.

6. An antibody that modulates the activity or expression of a CD83 polypeptide of SEQ ID NO:9, wherein said antibody comprises a light chain and a heavy chain, and wherein the antibody comprises the heavy chain sequence set forth in SEQ ID NO:60.

7. An antibody according to claim 6 comprising a light chain variable region comprising a CDR1 sequence of RCAYD (SEQ ID NO:37).

8. An antibody according to claim 6, wherein the light chain comprises the sequence of SEQ ID NO:58.

9. An antibody according to any one of claims 1-2, 3-8 or wherein the antibody is a polyclonal antibody.

10. An antibody according to any one of claims 1-2, 3-8 or wherein the antibody is a monoclonal antibody.

11. The antibody of claim 1, wherein the heavy chain variable region CDR2 of the antibody comprises the sequence YASGSTYY (SEQ ID NO:27).

12. The antibody of claim 1, wherein the heavy chain variable region CDR3 of the antibody comprises the sequence EHAGYSGDTGH (SEQ ID NO:32).

13. The antibody of claim 1, wherein the heavy chain variable region comprises one or more of the CDR1 of the antibody comprising sequence SYDMT (SEQ ID NO:23), the CDR2 of the antibody comprising sequence YASGSTYY (SEQ ID NO:27) or the CDR3 of the antibody comprising sequence EHAGYSGDTGH (SEQ ID NO:32).

14. The antibody of claim 2, wherein the heavy chain variable region CDR1 of the antibody comprises the sequence SYDMT (SEQ ID NO:23).

15. The antibody of claim 2, wherein the heavy chain variable region CDR2 of the antibody comprises the sequence YASGSTYY (SEQ ID NO:27).

16. The antibody of claim 2, wherein the heavy chain variable region CDR3 of the antibody comprises the sequence EHAGYSGDTGH (SEQ ID NO:32).

17. The antibody of claim 2, wherein the heavy chain variable region comprises one or more of the CDR1 of the antibody comprising sequence SYDMT (SEQ ID NO:23), the CDR2 of the antibody comprising sequence YASGSTYY (SEQ ID NO:27) or the CDR3 of the antibody comprising sequence EHAGYSGDTGH (SEQ ID NO:32).

18. The antibody of claim 4 wherein the light chain variable region CDR1 of the antibody comprises the sequence RCAYD (SEQ ID NO:37).

19. The antibody of claim 4 wherein the light chain variable region CDR2 of the antibody comprises the sequence OSISTY (SEQ ID NO:40.

20. The antibody of claim 4 wherein the light chain variable region CDR3 of the antibody comprises the sequence QQGYTHSNVDNV (SEQ ID NO:44).

21. The antibody of claim 4, wherein the light chain variable region comprises one or more of the CDR1 of the antibody comprising sequence RCAYD (SEQ ID NO:37), the CDR2 of the antibody comprising sequence OSISTY (SEQ ID NO:40, or the CDR3 of the antibody comprising sequence QQGYTHSNVDNV (SEQ ID NO:44).

22. The antibody of claim 4, wherein the light chain comprises the sequence set forth in SEQ ID NO:58.

23. The antibody of claim 5 wherein the light chain variable region CDR1 of the antibody comprises the sequence RCAYD (SEQ ID NO:37).

24. The antibody of claim 5 wherein the light chain variable region CDR2 of the antibody comprises a-the sequence OSISTY (SEQ ID NO:40.

25. The antibody of claim 5 wherein the light chain variable region CDR3 of the antibody comprises the sequence QQGYTHSNVDNV (SEQ ID NO:44).

26. The antibody of claim 5, wherein the light chain variable region comprises one or more of the CDR1 of the antibody comprising sequence RCAYD (SEQ ID NO:37); the CDR2 of the antibody comprising sequence OSISTY (SEQ ID NO:40 or the CDR3 of the antibody comprising sequence QQGYTHSNVDNV (SEQ ID NO:44).

27. The antibody of claim 5, wherein the light chain comprises the sequence set forth in SEQ ID NO:58.

28. An antibody according to claim 6 comprising a light chain variable region comprising a CDR2 sequence of OSISTY (SEQ ID NO:40).

29. An antibody according to claim 6 comprising a light chain variable region comprising a CDR3 sequence of QQGYTHSNVDNV (SEQ ID NO:44).

30. The antibody of claim 6, wherein the light chain variable region comprises one or more of the CDR1 of the antibody comprising sequence RCAYD (SEQ ID NO:37); the CDR2 of the antibody comprising sequence OSISTY (SEQ ID NO:40 or the CDR3 of the antibody comprising sequence QQGYTHSNVDNV (SEQ ID NO:44).

31. An antibody that modulates the activity or expression of a CD83 polypeptide of SEQ ID NO:9, wherein said antibody comprises a light chain and a heavy chain, and wherein the antibody comprises the light chain sequence set forth in SEQ ID NO:58.

32. The antibody of claim 31, wherein the heavy chain variable region CDR1 of the antibody comprises the sequence SYDMT (SEQ ID NO:23).

33. The antibody of claim 31, wherein the heavy chain variable region CDR2 of the antibody comprises the sequence YASGSTYY (SEQ ID NO:27).

34. The antibody of claim 31, wherein the heavy chain variable region CDR3 of the antibody comprises the sequence EHAGYSGDTGH (SEQ ID NO:32).

35. The antibody of claim 31, wherein the heavy chain variable region comprises one or more of the CDR1 of the antibody comprising sequence SYDMT (SEQ ID NO:23), the CDR2 of the antibody comprising sequence YASGSTYY (SEQ ID NO:27) or the CDR3 of the antibody comprising sequence EHAGYSGDTGH (SEQ ID NO:32).

* * * * *

UNITED STATES PATENT AND TRADEMARK OFFICE
CERTIFICATE OF CORRECTION

PATENT NO. : 7,618,629 B2 Page 1 of 1
APPLICATION NO. : 10/496284
DATED : November 17, 2009
INVENTOR(S) : Ramsdell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 534 days.

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,618,629 B2 | Page 1 of 2 |
| APPLICATION NO. | : 10/496284 | |
| DATED | : November 17, 2009 | |
| INVENTOR(S) | : Fred Ramsdell et al. | |

It is certified that error appears in the above-identified patent and that said Letters Patent is hereby corrected as shown below:

Col. 30, lines 24-25; should read; KNVYNNNW (SEQ ID NO.:43), or QSVYDNDE can be used in an antibody or other binding moiety to Col. 123; lines 61-62; should read;
9. An antibody according to anyone of claims 1-2, [[3-8]] 4-6 or 31 wherein the antibody is a polyclonal antibody.

Col. 123; lines 63-64; should read;
10. An antibody according to anyone of claims 1-2 [[3-8]] 4-6 or 31 wherein the antibody is a monoclonal antibody.

Col. 124; lines 51-53; should read;
19. The antibody of claim 4 wherein the light chain variable region CDR2 of the antibody comprises the sequence [[O]]QSISTY (SEQ ID NO: 40).

Col. 124; lines 57-62; should read;
21. The antibody of claim 4, wherein the light chain variable region comprises one or more of the CDR1 of the antibody comprising sequence RCAYD (SEQ ID NO: 37), the CDR2 of the antibody comprising sequence [[0]]QSISTY (SEQ ID NO:40), or the CDR3 of the antibody comprising sequence QQGYTHSNVDNV (SEQ ID NO: 44).

Col. 125; lines 1-3; should read;
24. The antibody of claim 5 wherein the light chain variable region CDR2 of the antibody comprises [[a]] the sequence [[0]QSISTY (SEQ ID NO:40).

Signed and Sealed this
Eighteenth Day of January, 2011

David J. Kappos
*Director of the United States Patent and Trademark Office*

Col. 125; lines 7-12; should read;
26. The antibody of claim 5, wherein the light chain variable region comprises one or more of the CDR1 of the antibody comprising sequence RCAYD (SEQ ID NO: 37); the CDR2 of the antibody comprising sequence [[0]]QSISTY (SEQ ID NO: 40) or the CDR3 of the antibody comprising sequence QQGYTHSNVDNV (SEQ ID NO:44).

Col. 125; lines 15-17; should read;
28. An antibody according to claim 77 comprising a light chain variable region comprising a CDR2 sequence of [[O]]QSISTY (SEQ ID NO:40).

Cols. 125-126; lines 21-2; should read;
30. The antibody of claim 77, wherein the light chain variable region comprises one or more of the CDR1 of the antibody comprising sequence RCAYD (SEQ ID NO:37); the CDR2 of the antibody comprising sequence [[0]]QSISTY (SEQ ID NO: 40) or the CDR3 of the antibody comprising sequence QQGYTHSNVDNV (SEQ ID NO:44).

SEQUENCE LISTING

<160> NUMBER OF SEQ ID NOS: 69

<210> SEQ ID NO 1
<211> LENGTH: 2051
<212> TYPE: DNA
<213> ORGANISM: Mus musculus

<400> SEQUENCE: 1

```
gcgctccagc cgcatgtcgc aaggcctcca gctcctgttt ctaggctgcg cctgcagcct      60
ggcacccgcg atggcgatgc gggaggtgac ggtggcttgc tccgagaccg ccgacttgcc     120
ttgcacagcg ccctgggacc cgcagctctc ctatgcagtg tcctgggcca aggtctccga     180
gagtggcact gagagtgtgg agctcccgga gagcaagcaa aacagctcct tcgaggcccc     240
caggagaagg gcctattccc tgacgatcca aaacactacc atctgcagct cgggcaccta     300
caggtgtgcc ctgcaggagc tcggagggca gcgcaacttg agcggcaccg tggttctgaa     360
ggtgacagga tgccccaagg aagctacaga gtcaactttc aggaagtaca gggcagaagc     420
tgtgttgctc ttctctctgg ttgttttcta cctgacactc atcattttca cctgcaaatt     480
tgcacgacta caaagcattt tcccagatat ttctaaacct ggtacggaac aagcttttct     540
```

-continued

```
tccagtcacc tccccaagca aacatttggg gccagtgacc cttcctaaga cagaaacggt    600
atgagtagga tctccactgg ttttacaaa gccaagggca catcagatca gtgtgcctga    660
atgccaccg gacaagagaa gaatgagctc catcctcaga tggcaacctt tctttgaagt    720
ccttcacctg acagtgggct ccacactact ccctgacaca gggtcttgag caccatcata    780
tgatcacgaa gcatggagta tcaccgcttc tctgtggctg tcagcttaat gtttcatgtg    840
gctatctggt caacctcgtg agtgcttttc agtcatctac aagctatggt gagatgcagg    900
tgaagcaggg tcatgggaaa tttgaacact ctgagctggc cctgtgacag actcctgagg    960
acagctgtcc tctcctacat ctgggataca tctctttgaa tttgtcctgt ttcgttgcac   1020
cagcccagat gtctcacatc tggcggaaat tgacaggcca agctgtgagc agtgggaaa   1080
tatttagcaa ataatttccc agtgcgaagg tcctgctatt agtaaggagt attatgtgta   1140
catagaaatg agaggtcagt gaactattcc ccagcagggc cttttcatct ggaaaagaca   1200
tccacaaaag cagcaataca gagggatgcc acatttattt ttttaatctt catgtacttg   1260
tcaaagaaga attttcatg ttttttcaaa gaagtgtgtt tctttccttt tttaaaatat   1320
gaaggtctag ttacatagca ttgctagctg acaagcagcc tgagagaaga tggagaatgt   1380
tcctcaaaat agggacagca agctagaagc actgtacagt gccctgctgg aagggcaga   1440
caatggactg agaaaccaga agtctggcca aagattgtc tgtatgattc tggacgagtc   1500
acttgtggtt ttcactctct ggttagtaaa ccagatagtt tagtctgggt tgaatacaat   1560
ggatgtgaag ttgcttgggg aaagctgaat gtagtgaata cattggcaac tctactgggc   1620
tgttaccttg ttgatatcct agagttctgg agctgagcga atgcctgtca tatctcagct   1680
tgcccatcaa tccaaacaca ggaggctaca aaaaggacat gagcatggtc ttctgtgtga   1740
actcctcctg agaaacgtgg agactggctc agcgctttgc gcttgaagga ctaatcacaa   1800
gttcttgaag atatggacct agggggagcta ttgcgccacg acaggaggaa gttctccagat   1860
gttgcattga tgtaacattg ttgcatttct ttaatgagct gggctccttc ctcatttgct   1920
tcccaaagag attttgtccc actaatggtg tgcccatcac ccacactatg aaagtaaaag   1980
ggatgctgag cagatacagc gtgcttacct ctcagccatg actttcatgc tattaaaaga   2040
atgcatgtga a                                                        2051
```

<210> SEQ ID NO 2
<211> LENGTH: 196
<212> TYPE: PRT
<213> ORGANISM: Mus musculus

<400> SEQUENCE: 2

Met Ser Gln Gly Leu Gln Leu Leu Phe Leu Gly Cys Ala Cys Ser Leu
1               5                   10                  15

Ala Pro Ala Met Ala Met Arg Glu Val Thr Val Ala Cys Ser Glu Thr
            20                  25                  30

Ala Asp Leu Pro Cys Thr Ala Pro Trp Asp Pro Gln Leu Ser Tyr Ala
        35                  40                  45

Val Ser Trp Ala Lys Val Ser Glu Ser Gly Thr Glu Ser Val Glu Leu
    50                  55                  60

Pro Glu Ser Lys Gln Asn Ser Ser Phe Glu Ala Pro Arg Arg Arg Ala
65                  70                  75                  80

Tyr Ser Leu Thr Ile Gln Asn Thr Thr Ile Cys Ser Ser Gly Thr Tyr
                85                  90                  95

Arg Cys Ala Leu Gln Glu Leu Gly Gly Gln Arg Asn Leu Ser Gly Thr

```
                100             105             110
        Val Val Leu Lys Val Thr Gly Cys Pro Lys Glu Ala Thr Glu Ser Thr
                115                     120                 125

Phe Arg Lys Tyr Arg Ala Glu Ala Val Leu Leu Phe Ser Leu Val Val
                130                     135                 140

Phe Tyr Leu Thr Leu Ile Ile Phe Thr Cys Lys Phe Ala Arg Leu Gln
        145                     150                 155                 160

Ser Ile Phe Pro Asp Ile Ser Lys Pro Gly Thr Glu Gln Ala Phe Leu
                        165                 170                 175

Pro Val Thr Ser Pro Ser Lys His Leu Gly Pro Val Thr Leu Pro Lys
                180                     185                 190

Thr Glu Thr Val
                195

<210> SEQ ID NO 3
<211> LENGTH: 2051
<212> TYPE: DNA
<213> ORGANISM: Artificial Sequence
<220> FEATURE:
<223> OTHER INFORMATION: Mutant CD83 sequence

<400> SEQUENCE: 3
gcgctccagc cgcatgtcgc aaggcctcca gctcctgttt ctaggctgcg cctgcagcct      60
ggcacccgcg atggcgatgc gggaggtgac ggtggcttgc tccgagaccg ccgacttgcc     120
ttgcacagcg ccctgggacc cgcagctctc ctatgcagtg tcctgggcca aggtctccga     180
gagtggcact gagagtgtgg agctcccgga gagcaagcaa acagctcctc tcgaggcccc     240
caggagaagg gcctattccc tgacgatcca aaacactacc atctgcagct cgggcaccta     300
caggtgtgcc ctgcaggagc tcggagggca gcgcaacttg agcggcaccg tggttctgaa     360
ggtgacagga tgccccaagg aagctacaga gtcaactttc aggaagtaca gggcagaagc     420
tgtgttgctc ttctctctgg ttgttttcta cctgacactc atcattttca cctgcaaatt     480
tgcacgacta caaagcattt tcccagatat ttctaaacct ggtacggaac aagcttttct     540
tccagtcacc tccccaagca acatttgggc cagtgaccc ttcctaaga cagaaacggt     600
aagagtagga tctccactgg ttttacaaa gccaagggca catcagatca gtgtgcctga     660
atgccacccg gacaagagaa gaatgagctc catcctcaga tggcaacctt tctttgaagt     720
ccttcacctg acagtgggct ccacactact ccctgacaca gggtcttgag caccatcata     780
tgatcacgaa gcatggagta tcaccgcttc tctgtggctg tcagcttaat gtttcatgtg     840
gctatctggt caacctcgtg agtgcttttc agtcatctac aagctatggt gagatgcagg     900
tgaagcaggt catgggaaa tttgaacact ctgagctggc cctgtgacag actcctgagg     960
acagctgtcc tctcctacat ctgggataca tctctttgaa tttgtcctgt tcgttgcac    1020
cagcccagat gtctcacatc tggcggaaat tgacaggcca agctgtgagc agtgggaaa    1080
tatttagcaa ataatttccc agtgcgaagg tcctgctatt agtaaggagt attatgtgta    1140
catagaaatg agaggtcagt gaactattcc ccagcagggc cttttcatct ggaaaagaca    1200
tccacaaaag cagcaataca gagggatgcc acatttattt ttttaatctt catgtacttg    1260
tcaaagaaga atttttcatg ttttttcaaa gaagtgtgtt tctttccttt tttaaaatat    1320
gaaggtctag ttacatagca ttgctagctg acaagcagcc tgagagaaga tggagaatgt    1380
tcctcaaaat agggacagca agctagaagc actgtacagt gccctgctgg aagggcaga    1440
caatggactg agaaaccaga agtctggcca caagattgtc tgtatgattc tggacgagtc    1500
```

```
acttgtggtt ttcactctct ggttagtaaa ccagatagtt tagtctgggt tgaatacaat    1560
ggatgtgaag ttgcttgggg aaagctgaat gtagtgaata cattggcaac tctactgggc    1620
tgttaccttg ttgatatcct agagttctgg agctgagcga atgcctgtca tatctcagct    1680
tgcccatcaa tccaaacaca ggaggctaca aaaaggacat gagcatggtc ttctgtgtga    1740
actcctcctg agaaacgtgg agactggctc agcgctttgc gcttgaagga ctaatcacaa    1800
gttcttgaag atatggacct aggggagcta ttgcgccacg acaggaggaa gttctcagat    1860
gttgcattga tgtaacattg ttgcatttct ttaatgagct gggctccttc ctcatttgct    1920
tcccaaagag attttgtccc actaatggtg tgcccatcac ccacactatg aaagtaaaag    1980
ggatgctgag cagatacagc gtgcttacct ctcagccatg actttcatgc tattaaaaga    2040
atgcatgtga a                                                         2051
```

<210> SEQ ID NO 4
<211> LENGTH: 251
<212> TYPE: PRT
<213> ORGANISM: Artificial Sequence
<220> FEATURE:
<223> OTHER INFORMATION: Mutant CD83 sequence

<400> SEQUENCE: 4

```
Met Ser Gln Gly Leu Gln Leu Leu Phe Leu Gly Cys Ala Cys Ser Leu
 1               5                  10                  15

Ala Pro Ala Met Ala Met Arg Glu Val Thr Val Ala Cys Ser Glu Thr
            20                  25                  30

Ala Asp Leu Pro Cys Thr Ala Pro Trp Asp Pro Gln Leu Ser Tyr Ala
        35                  40                  45

Val Ser Trp Ala Lys Val Ser Glu Ser Gly Thr Glu Ser Val Glu Leu
    50                  55                  60

Pro Glu Ser Lys Gln Asn Ser Ser Phe Glu Ala Pro Arg Arg Arg Ala
65                  70                  75                  80

Tyr Ser Leu Thr Ile Gln Asn Thr Thr Ile Cys Ser Ser Gly Thr Tyr
                85                  90                  95

Arg Cys Ala Leu Gln Glu Leu Gly Gly Gln Arg Asn Leu Ser Gly Thr
            100                 105                 110

Val Val Leu Lys Val Thr Gly Cys Pro Lys Glu Ala Thr Glu Ser Thr
        115                 120                 125

Phe Arg Lys Tyr Arg Ala Glu Ala Val Leu Leu Phe Ser Leu Val Val
    130                 135                 140

Phe Tyr Leu Thr Leu Ile Ile Phe Thr Cys Lys Phe Ala Arg Leu Gln
145                 150                 155                 160

Ser Ile Phe Pro Asp Ile Ser Lys Pro Gly Thr Glu Gln Ala Phe Leu
                165                 170                 175

Pro Val Thr Ser Pro Ser Lys His Leu Gly Pro Val Thr Leu Pro Lys
            180                 185                 190

Thr Glu Thr Val Arg Val Gly Ser Pro Leu Val Phe Thr Lys Pro Arg
        195                 200                 205

Ala His Gln Ile Ser Val Pro Glu Cys His Pro Asp Lys Arg Arg Met
    210                 215                 220

Ser Ser Ile Leu Arg Trp Gln Pro Phe Phe Glu Val Leu His Leu Thr
225                 230                 235                 240

Val Gly Ser Thr Leu Leu Pro Asp Thr Gly Ser
                245                 250
```

<210> SEQ ID NO 5
<211> LENGTH: 756
<212> TYPE: DNA
<213> ORGANISM: Artificial Sequence
<220> FEATURE:
<223> OTHER INFORMATION: Mutant CD83 sequence

<400> SEQUENCE: 5

```
atgtcgcaag gcctccagct cctgtttcta ggctgcgcct gcagcctggc acccgcgatg      60
gcgatgcggg aggtgacggt ggcttgctcc gagaccgccg acttgccttg cacagcgccc     120
tgggacccgc agctctccta tgcagtgtcc tgggccaagg tctccgagag tggcactgag     180
agtgtggagc tcccggagag caagcaaaac agctccttcg aggcccccag agaagggcc      240
tattccctga cgatccaaaa cactaccatc tgcagctcgg caccatacag gtgtgccctg     300
caggagctcg agggcagcg caacttgagc ggcaccgtgg ttctgaaggt gacaggatgc     360
cccaaggaag ctacagagtc aactttcagg aagtacaggg cagaagctgt gttgctcttc     420
tctctggttg ttttctacct gacactcatc attttcacct gcaaatttgc acgactacaa    480
agcattttcc cagatatttc taaacctggt acggaacaag cttttcttcc agtcacctcc    540
ccaagcaaac atttggggcc agtgaccctt cctaagacag aaacggtaag agtaggatct    600
ccactggttt ttacaaagcc aagggcacat cagatcagtg tgcctgaatg ccacccggac    660
aagagaagaa tgagctccat cctcagatgg caacctttct ttgaagtcct tcacctgaca    720
gtgggctcca cactactccc tgacacaggg tcttga                              756
```

<210> SEQ ID NO 6

<400> SEQUENCE: 6

000

<210> SEQ ID NO 7
<211> LENGTH: 168
<212> TYPE: DNA
<213> ORGANISM: Artificial Sequence
<220> FEATURE:
<223> OTHER INFORMATION: Mutant CD83 sequence

<400> SEQUENCE: 7

```
agagtaggat ctccactggt ttttacaaag ccaagggcac atcagatcag tgtgcctgaa      60
tgccacccgg acaagagaag aatgagctcc atcctcagat ggcaaccttt ctttgaagtc     120
cttcacctga cagtgggctc cacactactc cctgacacag ggtcttga                  168
```

<210> SEQ ID NO 8
<211> LENGTH: 55
<212> TYPE: PRT
<213> ORGANISM: Artificial Sequence
<220> FEATURE:
<223> OTHER INFORMATION: Mutant CD83 sequence

<400> SEQUENCE: 8

```
Arg Val Gly Ser Pro Leu Val Phe Thr Lys Pro Arg Ala His Gln Ile
  1               5                  10                  15
Ser Val Pro Glu Cys His Pro Asp Lys Arg Arg Met Ser Ser Ile Leu
             20                  25                  30
Arg Trp Gln Pro Phe Phe Glu Val Leu His Leu Thr Val Gly Ser Thr
         35                  40                  45
Leu Leu Pro Asp Thr Gly Ser
```

<210> SEQ ID NO 9
<211> LENGTH: 205
<212> TYPE: PRT
<213> ORGANISM: Homo sapiens

<400> SEQUENCE: 9

Met Ser Arg Gly Leu Gln Leu Leu Leu Ser Cys Ala Tyr Ser Leu
1               5                   10                  15

Ala Pro Ala Thr Pro Glu Val Lys Val Ala Cys Ser Glu Asp Val Asp
            20                  25                  30

Leu Pro Cys Thr Ala Pro Trp Asp Pro Gln Val Pro Tyr Thr Val Ser
        35                  40                  45

Trp Val Lys Leu Leu Glu Gly Gly Glu Glu Arg Met Glu Thr Pro Gln
    50                  55                  60

Glu Asp His Leu Arg Gly Gln His Tyr His Gln Lys Gly Gln Asn Gly
65                  70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
            100                 105                 110

Asp Gly Gln Arg Asn Leu Ser Gly Lys Val Ile Leu Arg Val Thr Gly
        115                 120                 125

Cys Pro Ala Gln Arg Lys Glu Glu Thr Phe Lys Lys Tyr Arg Ala Glu
    130                 135                 140

Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
            180                 185                 190

His Leu Gly Leu Val Thr Pro His Lys Thr Glu Leu Val
        195                 200                 205

<210> SEQ ID NO 10
<211> LENGTH: 2574
<212> TYPE: DNA
<213> ORGANISM: Homo sapiens

<400> SEQUENCE: 10
cctggcgcag ccgcagcagc gacgcgagcg aactcggccg ggcccgggcg cgcgggggcg      60
ggacgcgcac gcggcgaggg cggcgggtga gccgggggcg gggacggggg cgggacgggg     120
gcgaaggggg cggggacggg ggcgcccgcc ggcctaacgg gattaggagg gcgcgccacc     180
cgcttccgct gcccgccggg gaatccccg ggtggcgccc agggaagttc ccgaacgggc      240
gggcataaaa gggcagccgc gccggcgccc cacagctctg cagctcgtgg cagcggcgca     300
gcgctccagc catgtcgcgc ggcctccagc ttctgctcct gagctgcgcc tacagcctgg     360
ctcccgcgac gccggaggtg aaggtggctt gctccgaaga tgtggacttg ccctgcaccg     420 cccccctggga tccgcaggtt ccctacacgg tctcctgggt caagttattg gagggtggtg     480
aagagaggat ggagacaccc caggaagacc acctcagggg acagcactat catcagaagg     540
ggcaaaatgg ttcttttgac gccccaatg aaaggcccta ttccctgaag atccgaaaca      600
ctaccagctg caactcgggg acatacaggt gcactctgca ggaccggat gggcagagaa      660

-continued

```
acctaagtgg caaggtgatc ttgagagtga caggatgccc tgcacagcgt aaagaagaga      720
cttttaagaa atacagagcg gagattgtcc tgctgctggc tctggttatt ttctacttaa      780
cactcatcat tttcacttgt aagtttgcac ggctacagag tatcttccca gattttccta     840
aagctggcat ggaacgagct tttctcccag ttacctcccc aaataagcat ttagggctag      900
tgactcctca caagacagaa ctggtatgag caggatttct gcaggttctt cttcctgaag      960
ctgaggctca ggggtgtgcc tgtctgttac actggaggag agaagaatga gcctacgctg     1020
aagatggcat cctgtgaagt ccttcacctc actgaaaaca tctggaaggg gatcccaccc     1080
catttctgt gggcaggcct cgaaaaccat cacatgacca catagcatga ggccactgct      1140
gcttctccat ggccaccttt tcagcgatgt atgcagctat ctggtcaacc tcctggacat     1200
tttttcagtc atataaaagc tatggtgaga tgcagctgga aagggtcttt gggaaatatg     1260
aatgccccca gctggcccgt gacagactcc tgaggacagc tgtcctcttc tgcatcttgg     1320
ggacatctct ttgaatttc tgtgttttgc tgtaccagcc cagatgtttt acgtctggga     1380
gaaattgaca gatcaagctg tgagacagtg ggaaatattt agcaaataat tcctggtgt      1440
gaaggtcctg ctattactaa ggagtaatct gtgtacaaag aaataacaag tcgatgaact     1500
attccccagc agggtctttt catctgggaa agacatccat aaagaagcaa taagaagag     1560
tgccacattt attttatat ctatatgtac ttgtcaaaga aggtttgtgt ttttctgctt      1620
ttgaaatctg tatctgtagt gagatagcat tgtgaactga caggcagcct ggacatagag     1680
agggagaaga agtcagagag ggtgacaaga tagagagcta tttaatggcc ggctggaaat     1740
gctgggctga cggtgcagtc tgggtgctcg cccacttgtc ccactatctg ggtgcatgat     1800
cttgagcaag ttccttctgg tgtctgcttt ctccattgta aaccacaagg ctgttgcatg     1860
ggctaatgaa gatcatatac gtgaaaatta tttgaaaaca tataaagcac tatacagatt     1920
cgaaactcca ttgagtcatt atccttgcta tgatgatggt gttttgggga tgagagggtg     1980
ctatccattt ctcatgtttt ccattgtttg aaacaaagaa ggttaccaag aagccttcc      2040
tgtagccttc tgtaggaatt cttttgggga agtgaggaag ccaggtccac ggtctgttct     2100
tgaagcagta gcctaacaca ctccaagata tggacacacg ggagccgctg gcagaaggga    2160
cttcacgaag tgttgcatgg atgttttagc cattgttggc tttcccttat caaacttggg    2220
cccttccctt cttggtttcc aaaggcattt attgctgagt tatatgttca ctgtcccct    2280
aatattaggg agtaaaacgg ataccaagtt gatttagtgt ttttacctct gtcttggctt    2340
tcatgttatt aaacgtatgc atgtgaagaa gggtgttttt ctgttttata ttcaactcat    2400
aagactttgg gataggaaaa atgagtaatg gttactaggc ttaatacctg ggtgattaca    2460
taatctgtac aacgaacccc catgatgtaa gtttacctat gtaacaaacc tgcacttata    2520
cccatgaact taaaatgaaa gttaaaaata aaaacatat acaaataaaa aaaa            2574
```

<210> SEQ ID NO 11
<211> LENGTH: 239
<212> TYPE: PRT
<213> ORGANISM: Oryctolagus cuniculus

<400> SEQUENCE: 11

```
Met Asp Met Arg Ala Pro Thr Gln Leu Leu Gly Leu Leu Leu Trp
  1               5                  10                  15

Leu Pro Gly Ala Arg Cys Ala Asp Val Val Met Thr Gln Thr Pro Ala
                 20                  25                  30

Ser Val Ser Ala Ala Val Gly Gly Thr Val Thr Ile Asn Cys Gln Ala
```

-continued

```
                35                  40                  45
Ser Glu Ser Ile Ser Asn Tyr Leu Ser Trp Tyr Gln Gln Lys Pro Gly
 50                  55                  60

Gln Pro Pro Lys Leu Leu Ile Tyr Arg Thr Ser Thr Leu Ala Ser Gly
 65                  70                  75                  80

Val Ser Ser Arg Phe Lys Gly Ser Gly Ser Gly Thr Glu Tyr Thr Leu
                 85                  90                  95

Thr Ile Ser Gly Val Gln Cys Asp Asp Val Ala Thr Tyr Tyr Cys Gln
                100                 105                 110

Cys Thr Ser Gly Gly Lys Phe Ile Ser Asp Gly Ala Ala Phe Gly Gly
            115                 120                 125

Gly Thr Glu Val Val Val Lys Gly Asp Pro Val Ala Pro Thr Val Leu
        130                 135                 140

Leu Phe Pro Pro Ser Ser Asp Glu Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
210                 215                 220

Gln Gly Thr Thr Ser Val Val Gln Ser Phe Ser Arg Lys Asn Cys
225                 230                 235

<210> SEQ ID NO 12
<211> LENGTH: 720
<212> TYPE: DNA
<213> ORGANISM: Oryctolagus cuniculus

<400> SEQUENCE: 12
atggacatga gggccccccac tcagctgctg gggctcctgc tgctctggct cccaggtgcc      60
agatgtgccg atgtcgtgat gacccagact ccagcctccg tgtctgcagc tgtgggaggc     120
acagtcacca tcaattgcca ggccagtgaa agcattagca actacttatc ctggtatcag     180
cagaaaccag ggcagcctcc caagctcctg atctacagga catccactct ggcatctggg     240
gtctcatcgc ggttcaaagg cagtggatct gggacagagt acactctcac catcagcggc     300
gtgcagtgtg acgatgttgc cacttactac tgtcaatgca cttctggtgg aagttcatt     360 agtgatggtg ctgctttcgg cggagggacc gaggtggtgg tcaaaggtga tccagttgca     420
cctactgtcc tcctcttccc accatctagc gatgaggtgg caactggaac agtcaccatc     480
gtgtgtgtgg cgaataaata ctttcccgat gtcaccgtca cctgggaggt ggatggcacc     540
acccaaacaa ctggcatcga gaacagtaaa acaccgcaga attctgcaga ttgtacctac     600
aacctcagca gcactctgac actgaccagc acacagtaca acagccacaa agagtacacc     660
tgcaaggtga cccagggcac gacctcagtc gtccagagct tcagtaggaa gaactgttaa     720

<210> SEQ ID NO 13
<211> LENGTH: 454
<212> TYPE: PRT
<213> ORGANISM: Oryctolagus cuniculus

<400> SEQUENCE: 13

Met Glu Thr Gly Leu Arg Trp Leu Leu Leu Val Ala Val Leu Lys Gly
```

```
          1               5                  10                 15
Val Gln Cys Gln Ser Val Glu Glu Ser Gly Gly Arg Leu Val Thr Pro
                20                  25                 30

Gly Thr Pro Leu Thr Leu Thr Cys Thr Val Ser Gly Phe Ser Leu Ser
                35                  40                 45

Asn Asn Ala Ile Asn Trp Val Arg Gln Ala Pro Gly Lys Gly Leu Glu
        50                  55                 60

Trp Ile Gly Tyr Ile Trp Ser Gly Gly Leu Thr Tyr Tyr Ala Asn Trp
65                      70                 75                 80

Ala Glu Gly Arg Phe Thr Ile Ser Lys Thr Ser Thr Val Asp Leu
                        85                 90                 95

Lys Met Thr Ser Pro Thr Ile Glu Asp Thr Ala Thr Tyr Phe Cys Ala
                100                 105                110

Arg Gly Ile Asn Asn Ser Ala Leu Trp Gly Pro Gly Thr Leu Val Thr
                115                 120                125

Val Ser Ser Gly Gln Pro Lys Ala Pro Ser Val Phe Pro Leu Ala Pro
        130                 135                140

Cys Cys Gly Asp Thr Pro Ser Ser Thr Val Thr Leu Gly Cys Leu Val
145                     150                 155                160

Lys Gly Tyr Leu Pro Glu Pro Val Thr Val Thr Trp Asn Ser Gly Thr
                    165                 170                175

Leu Thr Asn Gly Val Arg Thr Phe Pro Ser Val Arg Gln Ser Ser Gly
                180                 185                190

Leu Tyr Ser Leu Ser Ser Val Val Ser Val Thr Ser Ser Gln Pro
        195                 200                 205

Val Thr Cys Asn Val Ala His Pro Ala Thr Asn Thr Lys Val Asp Lys
        210                 215                 220

Thr Val Ala Pro Ser Thr Cys Ser Lys Pro Thr Cys Pro Pro Pro Glu
225                     230                 235                240

Leu Leu Gly Gly Pro Ser Val Phe Ile Phe Pro Pro Lys Pro Lys Asp
                    245                 250                255

Thr Leu Met Ile Ser Arg Thr Pro Glu Val Thr Cys Val Val Val Asp
                260                 265                270

Val Ser Gln Asp Asp Pro Glu Val Gln Phe Thr Trp Tyr Ile Asn Asn
        275                 280                 285

Glu Gln Val Arg Thr Ala Arg Pro Pro Leu Arg Glu Gln Gln Phe Asn
        290                 295                 300

Ser Thr Ile Arg Val Val Ser Thr Leu Pro Ile Ala His Gln Asp Trp
305                     310                 315                320

Leu Arg Gly Lys Glu Phe Lys Cys Lys Val His Asn Lys Ala Leu Pro
                    325                 330                335

Ala Pro Ile Glu Lys Thr Ile Ser Lys Ala Arg Gly Gln Pro Leu Glu
                340                 345                350

Pro Lys Val Tyr Thr Met Gly Pro Pro Arg Glu Glu Leu Ser Ser Arg
                355                 360                365

Ser Val Ser Leu Thr Cys Met Ile Asn Gly Phe Tyr Pro Ser Asp Ile
        370                 375                380

Ser Val Glu Trp Glu Lys Asn Gly Lys Ala Glu Asp Asn Tyr Lys Thr
385                     390                 395                400

Thr Pro Ala Val Leu Asp Ser Asp Gly Ser Tyr Phe Leu Tyr Asn Lys
                    405                 410                415

Leu Ser Val Pro Thr Ser Glu Trp Gln Arg Gly Asp Val Phe Thr Cys
                420                 425                430
```

Ser Val Met His Glu Ala Leu His Asn His Tyr Thr Gln Lys Ser Ile
        435                 440                 445

Ser Arg Ser Pro Gly Lys
    450

<210> SEQ ID NO 14
<211> LENGTH: 1362
<212> TYPE: DNA
<213> ORGANISM: Oryctolagus cuniculus

<400> SEQUENCE: 14

```
atggagacag gcctgcgctg gcttctcctg gtcgctgtgc tcaaaggtgt ccagtgtcag      60
tcggtggagg agtccggggg tcgcctggtc acgcctggga ccccctgac actcacctgc     120
accgtctctg gattctccct cagtaacaat gcaataaact gggtccgcca ggctccaggg    180
aaggggctag agtggatcgg atacatttgg agtggtgggc ttacatacta cgcgaactgg    240
gcggaaggcc gattcaccat ctccaaaacc tcgactacgt ggatctgaa gatgaccagt    300
ccgacaatcg aggacacggc caccatttc tgtgccagag ggattaataa ctccgctttg    360
tggggcccag gcaccctggt caccgtctcc tcagggcaac taaggctcc atcagtcttc    420
ccactggccc cctgctgcgg ggacacaccc tctagcacgg tgaccttggg ctgcctggtc    480
aaaggctacc tcccggagcc agtgaccgtg acctggaact cgggcaccct caccaatggg    540
gtacgcacct tcccgtccgt ccggcagtcc tcaggcctct actcgctgag cagcgtggtg    600
agcgtgacct caagcagcca gcccgtcacc tgcaacgtgg cccacccagc caccaacacc    660
aaagtggaca gaccgttgc gccctcgaca tgcagcaagc ccacgtgccc acccccctgaa    720
ctcctggggg gaccgtctgt cttcatcttc cccccaaaac ccaaggacac cctcatgatc    780
tcacgcaccc ccgaggtcac atgcgtggtg gtggacgtga gccaggatga ccccgaggtg    840
cagttcacat ggtacataaa caacgagcag gtgcgcaccg cccggccgcc gctacgggag    900
cagcagttca acagcacgat ccgcgtggtc agcaccctcc ccatcgcgca ccaggactgg    960
ctgagggcag aggagttcaa gtgcaaagtc acaacaagg cactcccggc ccccatcgag   1020
aaaaccatct ccaaagccag agggcagccc ctggagccga aggtctacac catgggccct   1080
cccgggagg agctgagcag caggtcggtc agcctgacct gcatgatcaa cggcttctac   1140
ccttccgaca tctcggtgga gtgggagaag acgggaagg cagaggacaa ctacaagacc   1200
acgccggccg tgctggacag cgacggctcc tacttcctct acaacaagct ctcagtgccc   1260
acgagtgagt ggcagcgggg cgacgtcttc acctgctccg tgatgcacga ggccttgcac   1320
aaccactaca cgcagaagtc catctcccgc tctccgggta aa                     1362
```

<210> SEQ ID NO 15
<211> LENGTH: 238
<212> TYPE: PRT
<213> ORGANISM: Oryctolagus cuniculus

<400> SEQUENCE: 15

Met Asp Thr Arg Ala Pro Thr Gln Leu Leu Gly Leu Leu Leu Leu Trp
  1               5                  10                  15

Leu Pro Gly Ala Arg Cys Ala Asp Val Val Met Thr Gln Thr Pro Ala
               20                  25                  30

Ser Val Ser Ala Ala Val Gly Gly Thr Val Thr Ile Asn Cys Gln Ser
           35                  40                  45

Ser Lys Asn Val Tyr Asn Asn Asn Trp Leu Ser Trp Phe Gln Gln Lys

```
                50                  55                  60
Pro Gly Gln Pro Pro Lys Leu Leu Ile Tyr Tyr Ala Ser Thr Leu Ala
65                  70                  75                  80

Ser Gly Val Pro Ser Arg Phe Arg Gly Ser Gly Ser Gly Thr Gln Phe
                85                  90                  95

Thr Leu Thr Ile Ser Asp Val Gln Cys Asp Asp Ala Ala Thr Tyr Tyr
            100                 105                 110

Cys Ala Gly Asp Tyr Ser Ser Ser Asp Asn Gly Phe Gly Gly Gly
        115                 120                 125

Thr Glu Val Val Val Lys Gly Asp Pro Val Ala Pro Thr Val Leu Leu
    130                 135                 140

Phe Pro Pro Ser Ser Asp Glu Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Ser Arg Lys Asn Cys
225                 230                 235
```

<210> SEQ ID NO 16
<211> LENGTH: 717
<212> TYPE: DNA
<213> ORGANISM: Oryctolagus cuniculus

<400> SEQUENCE: 16

```
atggacacca gggccccccac tcagctgctg gggctcctgc tgctctggct cccaggtgcc    60
agatgtgccg acgtcgtgat gacccagact ccagcctccg tgtctgcagc tgtgggaggc   120
acagtcacca tcaattgcca gtccagtaag aatgtttata taacaactg gttatcctgg   180
tttcagcaga aaccagggca gcctcccaag ctcctgatct attatgcatc cactctggca   240
tctggggtcc catcgcggtt cagaggcagt ggatctggga cacagttcac tctcaccatt   300
agcgacgtgc agtgtgacga tgctgccact tactactgtg caggcgatta tagtagtagt   360
agtgataatg gttcggcgg agggaccgag gtggtggtca aggtgatcc agttgcacct   420
actgtcctcc tcttcccacc atctagcgat gaggtggcaa ctggaacagt caccatcgtg   480
tgtgtggcga ataaatactt tcccgatgtc accgtcacct gggaggtgga tggcaccacc   540
caaacaactg gcatcgagaa cagtaaaaca ccgcagaatt ctgcagattg tacctacaac   600
ctcagcagca ctctgacact gaccagcaca gtacaacaa gccacaaaga gtacacctgc   660
aaggtgaccc agggcacgac ctcagtcgtc cagagcttca gtaggaagaa ctgttaa    717
```

<210> SEQ ID NO 17
<211> LENGTH: 452
<212> TYPE: PRT
<213> ORGANISM: Oryctolagus cuniculus

<400> SEQUENCE: 17

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
```

-continued

```
                    20                  25                  30
Gly Thr Pro Leu Thr Leu Thr Cys Thr Val Ser Gly Phe Thr Ile Ser
                35                  40                  45
Asp Tyr Asp Leu Ser Trp Val Arg Gln Ala Pro Gly Glu Gly Leu Lys
 50                  55                  60
Tyr Ile Gly Phe Ile Ala Ile Asp Gly Asn Pro Tyr Tyr Ala Thr Trp
 65                  70                  75                  80
Ala Lys Gly Arg Phe Thr Ile Ser Lys Thr Ser Thr Thr Val Asp Leu
                 85                  90                  95
Lys Ile Thr Ala Pro Thr Thr Glu Asp Thr Ala Thr Tyr Phe Cys Ala
                100                 105                 110
Arg Gly Ala Gly Asp Leu Trp Gly Pro Gly Thr Leu Val Thr Val Ser
            115                 120                 125
Ser Gly Gln Pro Lys Ala Pro Ser Val Phe Pro Leu Ala Pro Cys Cys
            130                 135                 140
Gly Asp Thr Pro Ser Ser Thr Val Thr Leu Gly Cys Leu Val Lys Gly
145                 150                 155                 160
Tyr Leu Pro Glu Pro Val Thr Val Thr Trp Asn Ser Gly Thr Leu Thr
                165                 170                 175
Asn Gly Val Arg Thr Phe Pro Ser Val Arg Gln Ser Ser Gly Leu Tyr
            180                 185                 190
Ser Leu Ser Ser Val Val Ser Val Thr Ser Ser Ser Gln Pro Val Thr
            195                 200                 205
Cys Asn Val Ala His Pro Ala Thr Asn Thr Lys Val Asp Lys Thr Val
210                 215                 220
Ala Pro Ser Thr Cys Ser Lys Pro Thr Cys Pro Pro Pro Glu Leu Leu
225                 230                 235                 240
Gly Gly Pro Ser Val Phe Ile Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Asp Asp Pro Glu Val Gln Phe Thr Trp Tyr Ile Asn Asn Glu Gln
            275                 280                 285
Val Arg Thr Ala Arg Pro Pro Leu Arg Glu Gln Gln Phe Asn Ser Thr
            290                 295                 300
Ile Arg Val Val Ser Thr Leu Pro Ile Ala His Gln Asp Trp Leu Arg
305                 310                 315                 320
Gly Lys Glu Phe Lys Cys Lys Val His Asn Lys Ala Leu Pro Ala Pro
                325                 330                 335
Ile Glu Lys Thr Ile Ser Lys Ala Arg Gly Gln Pro Leu Glu Pro Lys
            340                 345                 350
Val Tyr Thr Met Gly Pro Pro Arg Glu Glu Leu Ser Ser Arg Ser Val
            355                 360                 365
Ser Leu Thr Cys Met Ile Asn Gly Phe Tyr Pro Ser Asp Ile Ser Val
            370                 375                 380
Glu Trp Glu Lys Asn Gly Lys Ala Glu Asp Asn Tyr Lys Thr Thr Pro
385                 390                 395                 400
Ala Val Leu Asp Ser Asp Gly Ser Tyr Phe Leu Tyr Asn Lys Leu Ser
                405                 410                 415
Val Pro Thr Ser Glu Trp Gln Arg Gly Asp Val Phe Thr Cys Ser Val
            420                 425                 430
Met His Glu Ala Leu His Asn His Tyr Thr Gln Lys Ser Ile Ser Arg
            435                 440                 445
```

Ser Pro Gly Lys
    450

<210> SEQ ID NO 18
<211> LENGTH: 1356
<212> TYPE: DNA
<213> ORGANISM: Oryctolagus cuniculus

<400> SEQUENCE: 18

| | | | | | |
|---|---|---|---|---|---|
| atggagacag | gcctgcgctg | gcttctcctg | gtcgctgtgc | tcaaaggtgt | ccagtgtcag | 60 |
| tcggtggagg | agtccggggg | tcgcctggtc | acgcctggga | cacccctgac | actcacctgc | 120 |
| acagtctctg | gattcaccat | cagtgactac | gacttgagct | gggtccgcca | ggctccaggg | 180 |
| gaggggctga | atacatcgg | attcattgct | attgatggta | acccatacta | cgcgacctgg | 240 |
| gcaaaaggcc | gattcaccat | ctccaaaacc | tcgaccacgg | tggatctgaa | aatcaccgct | 300 |
| ccgacaaccg | aagacacggc | cacgtatttc | tgtgccagag | gggcagggga | cctctggggc | 360 |
| ccagggaccc | tcgtcaccgt | ctcttcaggg | caacctaagg | ctccatcagt | cttcccactg | 420 |
| gcccctgct | gcggggacac | accctctagc | acggtgacct | gggctgcct | ggtcaaaggc | 480 |
| tacctcccgg | agccagtgac | cgtgacctgg | aactcgggca | ccctcaccaa | tggggtacgc | 540 |
| accttcccgt | ccgtccggca | gtcctcaggc | ctctactcgc | tgagcagcgt | ggtgagcgtg | 600 |
| acctcaagca | gccagcccgt | cacctgcaac | gtggcccacc | cagccaccaa | caccaaagtg | 660 |
| gacaagaccg | ttgcgccctc | gacatgcagc | aagcccacgt | gcccaccccc | tgaactcctg | 720 |
| gggggaccgt | ctgtcttcat | cttccccccca | aaacccaagg | acaccctcat | gatctcacgc | 780 |
| accccgagg | tcacatgcgt | ggtggtggac | gtgagccagg | atgaccccga | ggtgcagttc | 840 |
| acatggtaca | taaacaacga | gcaggtgcgc | accgcccggc | cgccgctacg | ggagcagcag | 900 |
| ttcaacagca | cgatccgcgt | ggtcagcacc | ctccccatcg | cgcaccagga | ctggctgagg | 960 |
| ggcaaggagt | tcaagtgcaa | agtccacaac | aaggcactcc | cggcccccat | cgagaaaacc | 1020 |
| atctccaaag | ccagagggca | gccccctgag | ccgaaggtct | acaccatggg | ccctccccgg | 1080 |
| gaggagctga | gcagcaggtc | ggtcagcctg | acctgcatga | tcaacggctt | ctacccttcc | 1140 |
| gacatctcgg | tggagtggga | gaagaacggg | aaggcagagg | acaactacaa | gaccacgccg | 1200 |
| gccgtgctgg | acagcgacgg | ctcctacttc | ctctacaaca | gctctcagt | gcccacgagt | 1260 |
| gagtggcagc | ggggcgacgt | cttcacctgc | tccgtgatgc | acgaggcctt | gcacaaccac | 1320 |
| tacacgcaga | agtccatctc | ccgctctccg | ggtaaa | | | 1356 |

<210> SEQ ID NO 19
<211> LENGTH: 238
<212> TYPE: PRT
<213> ORGANISM: Oryctolagus cuniculus
<220> FEATURE:
<221> NAME/KEY: SITE
<222> LOCATION: (1)...(238)
<223> OTHER INFORMATION: Xaa = any amino acid

<400> SEQUENCE: 19

Met Asp Xaa Arg Ala Pro Thr Gln Leu Leu Gly Leu Leu Leu Leu Trp
 1               5                  10                  15

Leu Pro Gly Ala Arg Cys Ala Leu Val Met Thr Gln Thr Pro Ala Ser
            20                  25                  30

Val Ser Ala Ala Val Gly Gly Thr Val Thr Ile Asn Cys Gln Ser Ser
        35                  40                  45

```
Gln Ser Val Tyr Asp Asn Asp Glu Leu Ser Trp Tyr Gln Gln Lys Pro
    50                  55                  60
Gly Gln Pro Pro Lys Leu Leu Ile Tyr Leu Ala Ser Lys Leu Ala Ser
65                  70                  75                  80
Gly Val Pro Ser Arg Phe Lys Gly Ser Gly Ser Gly Thr Gln Phe Ala
                85                  90                  95
Leu Thr Ile Ser Gly Val Gln Cys Asp Asp Ala Ala Thr Tyr Tyr Cys
                100                 105                 110
Gln Ala Thr His Tyr Ser Ser Asp Trp Tyr Leu Thr Phe Gly Gly Gly
            115                 120                 125
Thr Glu Val Val Lys Gly Asp Pro Val Ala Pro Thr Val Leu Leu
    130                 135                 140
Phe Pro Pro Ser Ser Asp Glu Val Ala Thr Gly Thr Val Thr Ile Val
145                 150                 155                 160
Cys Val Ala Asn Lys Tyr Phe Pro Asp Val Thr Val Thr Trp Glu Val
                165                 170                 175
Asp Gly Thr Thr Gln Thr Thr Gly Ile Glu Asn Ser Lys Thr Pro Gln
                180                 185                 190
Asn Ser Ala Asp Cys Thr Tyr Asn Leu Ser Ser Thr Leu Thr Leu Thr
            195                 200                 205
Ser Thr Gln Tyr Asn Ser His Lys Glu Tyr Thr Cys Lys Val Thr Gln
    210                 215                 220
Gly Thr Thr Ser Val Val Gln Ser Phe Ser Arg Lys Asn Cys
225                 230                 235
```

<210> SEQ ID NO 20
<211> LENGTH: 717
<212> TYPE: DNA
<213> ORGANISM: Oryctolagus cuniculus

<400> SEQUENCE: 20

```
atggacatra gggccccac tcagctgctg gggctcctgc tgctctggct cccaggtgcc      60
agatgtgccc ttgtgatgac ccagactcca gcctccgtgt ctgcagctgt gggaggcaca     120
gtcaccatca attgccagtc cagtcagagt gtttatgata cgacgaatt atcctggtat      180
cagcagaaac cagggcagcc tcccaagctc ctgatctatc tggcatccaa gttggcatct     240
ggggtcccat cccgattcaa aggcagtgga tctgggacac agttcgctct caccatcagc     300
ggcgtgcagt gtgacgatgc tgccacttac tactgtcaag ccactcatta tagtagtgat     360
tggtatctta ctttcggcgg agggaccgag gtggtggtca aaggtgatcc agttgcacct     420
actgtcctcc tcttcccacc atctagcgat gaggtggcaa ctggaacagt caccatcgtg     480
tgtgtggcga ataaatactt tcccgatgtc accgtcacct gggaggtgga tggcaccacc     540
caaacaactg gcatcgagaa cagtaaaaca ccgcagaatt ctgcagattg tacctacaac     600
ctcagcagca ctctgacact gaccagcaca cagtacaaca gccacaaaga gtacacctgc     660
aaggtgaccc agggcacgac ctcagtcgtc cagagcttca gtaggaagaa ctgttaa       717
```

<210> SEQ ID NO 21
<211> LENGTH: 454
<212> TYPE: PRT
<213> ORGANISM: Oryctolagus cuniculus

<400> SEQUENCE: 21

```
Met Glu Thr Gly Leu Arg Trp Leu Leu Leu Val Ala Val Leu Lys Gly
1               5                   10                  15
```

-continued

```
Val His Cys Gln Ser Val Glu Glu Ser Gly Gly Arg Leu Val Thr Pro
         20                  25                  30

Gly Thr Pro Leu Thr Leu Thr Cys Thr Ala Ser Gly Phe Ser Arg Ser
             35                  40                  45

Ser Tyr Asp Met Ser Trp Val Arg Gln Ala Pro Gly Lys Gly Leu Glu
 50                  55                  60

Trp Val Gly Val Ile Ser Thr Ala Tyr Asn Ser His Tyr Ala Ser Trp
 65                  70                  75                  80

Ala Lys Gly Arg Phe Thr Ile Ser Arg Thr Ser Thr Thr Val Asp Leu
                 85                  90                  95

Lys Met Thr Ser Leu Thr Thr Glu Asp Thr Ala Thr Tyr Phe Cys Ala
            100                 105                 110

Arg Gly Gly Ser Trp Leu Asp Leu Trp Gly Gln Gly Thr Leu Val Thr
            115                 120                 125

Val Ser Ser Gly Gln Pro Lys Ala Pro Ser Val Phe Pro Leu Ala Pro
130                 135                 140

Cys Cys Gly Asp Thr Pro Ser Ser Thr Val Thr Leu Gly Cys Leu Val
145                 150                 155                 160

Lys Gly Tyr Leu Pro Glu Pro Val Thr Val Thr Trp Asn Ser Gly Thr
                165                 170                 175

Leu Thr Asn Gly Val Arg Thr Phe Pro Ser Val Arg Gln Ser Ser Gly
            180                 185                 190

Leu Tyr Ser Leu Ser Ser Val Val Ser Val Thr Ser Ser Ser Gln Pro
            195                 200                 205

Val Thr Cys Asn Val Ala His Pro Ala Thr Asn Thr Lys Val Asp Lys
            210                 215                 220

Thr Val Ala Pro Ser Thr Cys Ser Lys Pro Thr Cys Pro Pro Pro Glu
225                 230                 235                 240

Leu Leu Gly Gly Pro Ser Val Phe Ile Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Asp Asp Pro Glu Val Gln Phe Thr Trp Tyr Ile Asn Asn
            275                 280                 285

Glu Gln Val Arg Thr Ala Arg Pro Pro Leu Arg Glu Gln Gln Phe Asn
290                 295                 300

Ser Thr Ile Arg Val Val Ser Thr Leu Pro Ile Ala His Gln Asp Trp
305                 310                 315                 320

Leu Arg Gly Lys Glu Phe Lys Cys Lys Val His Asn Lys Ala Leu Pro
                325                 330                 335

Ala Pro Ile Glu Lys Thr Ile Ser Lys Ala Arg Gly Gln Pro Leu Glu
            340                 345                 350

Pro Lys Val Tyr Thr Met Gly Pro Pro Arg Glu Glu Leu Ser Ser Arg
            355                 360                 365

Ser Val Ser Leu Thr Cys Met Ile Asn Gly Phe Tyr Pro Ser Asp Ile
370                 375                 380

Ser Val Glu Trp Glu Lys Asn Gly Lys Ala Glu Asp Asn Tyr Lys Thr
385                 390                 395                 400

Thr Pro Ala Val Leu Asp Ser Asp Gly Ser Tyr Phe Leu Tyr Asn Lys
                405                 410                 415

Leu Ser Val Pro Thr Ser Glu Trp Gln Arg Gly Asp Val Phe Thr Cys
            420                 425                 430

Ser Val Met His Glu Ala Leu His Asn His Tyr Thr Gln Lys Ser Ile
```

-continued

```
                435                 440                 445
Ser Arg Ser Pro Gly Lys
        450

<210> SEQ ID NO 22
<211> LENGTH: 1362
<212> TYPE: PRT
<213> ORGANISM: Oryctolagus cuniculus

<400> SEQUENCE: 22

Ala Thr Gly Gly Ala Gly Ala Cys Ala Gly Gly Cys Cys Thr Gly Cys
  1               5                  10                  15

Gly Cys Thr Gly Gly Cys Thr Thr Cys Thr Cys Cys Thr Gly Gly Thr
             20                  25                  30

Cys Gly Cys Thr Gly Thr Gly Cys Thr Cys Ala Ala Gly Gly Gly Thr
         35                  40                  45

Gly Thr Cys Cys Ala Cys Thr Gly Thr Cys Ala Gly Thr Cys Gly Gly
     50                  55                  60

Thr Gly Gly Ala Gly Gly Ala Gly Thr Cys Cys Gly Gly Gly Gly Gly
 65                  70                  75                  80

Thr Cys Gly Cys Cys Thr Gly Gly Thr Cys Ala Cys Gly Cys Cys Thr
             85                  90                  95

Gly Gly Gly Ala Cys Ala Cys Cys Cys Thr Gly Ala Cys Ala Cys Thr
            100                 105                 110

Thr Cys Ala Cys Cys Thr Gly Cys Ala Cys Ala Gly Cys Cys Thr Cys
            115                 120                 125

Thr Gly Gly Ala Thr Thr Cys Thr Cys Cys Gly Cys Ala Gly Cys Thr
        130                 135                 140

Ala Gly Cys Thr Ala Cys Gly Ala Cys Ala Thr Gly Ala Gly Cys Thr
145                 150                 155                 160

Gly Gly Gly Thr Cys Cys Gly Cys Cys Ala Gly Gly Cys Thr Cys Cys
                165                 170                 175

Ala Gly Gly Gly Ala Ala Gly Gly Gly Cys Thr Gly Gly Ala Ala
            180                 185                 190

Thr Gly Gly Thr Cys Gly Gly Ala Gly Thr Cys Ala Thr Thr Ala
        195                 200                 205

Gly Thr Ala Cys Thr Gly Cys Thr Thr Ala Thr Ala Ala Cys Thr Cys
    210                 215                 220

Ala Cys Ala Cys Thr Ala Cys Gly Cys Gly Ala Gly Cys Thr Gly Gly
225                 230                 235                 240

Gly Cys Ala Ala Ala Gly Gly Cys Cys Gly Ala Thr Thr Cys Ala
                245                 250                 255

Cys Cys Ala Thr Cys Thr Cys Cys Ala Gly Ala Ala Cys Cys Thr Cys
            260                 265                 270

Gly Ala Cys Cys Ala Cys Gly Gly Thr Gly Gly Ala Thr Cys Thr Gly
        275                 280                 285

Ala Ala Ala Ala Thr Gly Ala Cys Cys Ala Gly Thr Cys Thr Gly Ala
    290                 295                 300

Cys Ala Ala Cys Cys Gly Ala Ala Gly Ala Cys Ala Cys Gly Gly Cys
305                 310                 315                 320

Cys Ala Cys Cys Thr Ala Thr Thr Thr Cys Thr Gly Thr Gly Cys Cys
                325                 330                 335

Ala Gly Ala Gly Gly Gly Gly Gly Thr Ala Gly Thr Thr Gly Gly Thr
            340                 345                 350
```

-continued

```
Thr Gly Gly Ala Thr Cys Thr Cys Thr Gly Gly Gly Gly Cys Cys Ala
        355                 360                 365
Gly Gly Gly Cys Ala Cys Cys Cys Thr Gly Gly Thr Cys Ala Cys Cys
    370                 375                 380

Gly Thr Cys Thr Cys Cys Thr Cys Ala Gly Gly Gly Cys Ala Ala Cys
385                 390                 395                 400

Cys Thr Ala Ala Gly Gly Cys Thr Cys Cys Ala Thr Cys Ala Gly Thr
                405                 410                 415

Cys Thr Thr Cys Cys Cys Ala Cys Thr Gly Gly Cys Cys Cys Cys Cys
            420                 425                 430

Thr Gly Cys Thr Gly Cys Gly Gly Gly Gly Ala Cys Ala Cys Ala Cys
        435                 440                 445
Cys Cys Thr Cys Thr Ala Gly Cys Ala Cys Gly Gly Thr Gly Ala Cys
    450                 455                 460

Cys Thr Thr Gly Gly Gly Cys Thr Gly Cys Cys Thr Gly Gly Thr Cys
465                 470                 475                 480

Ala Ala Ala Gly Gly Cys Thr Ala Cys Cys Thr Cys Cys Cys Gly Gly
                485                 490                 495
Ala Gly Cys Cys Ala Gly Thr Gly Ala Cys Cys Gly Thr Gly Ala Cys
            500                 505                 510

Cys Thr Gly Gly Ala Ala Cys Thr Cys Gly Gly Gly Cys Ala Cys Cys
        515                 520                 525

Cys Thr Cys Ala Cys Cys Ala Ala Thr Gly Gly Gly Gly Thr Ala Cys
    530                 535                 540

Gly Cys Ala Cys Cys Thr Thr Cys Cys Cys Gly Thr Cys Cys Gly Thr
545                 550                 555                 560
Cys Cys Gly Gly Cys Ala Gly Thr Cys Cys Thr Cys Ala Gly Gly Cys
                565                 570                 575
Cys Thr Cys Thr Ala Cys Thr Cys Gly Cys Thr Gly Ala Gly Cys Ala
            580                 585                 590
Gly Cys Gly Thr Gly Gly Thr Gly Ala Gly Cys Gly Thr Gly Ala Cys
        595                 600                 605

Cys Thr Cys Ala Ala Gly Cys Ala Gly Cys Cys Ala Gly Cys Cys Cys
    610                 615                 620

Gly Thr Cys Ala Cys Cys Thr Gly Cys Ala Ala Cys Gly Thr Gly Gly
625                 630                 635                 640

Cys Cys Cys Ala Cys Cys Cys Ala Gly Cys Cys Ala Cys Cys Ala Ala
                645                 650                 655

Cys Ala Cys Cys Ala Ala Ala Gly Thr Gly Gly Ala Cys Ala Ala Gly
            660                 665                 670

Ala Cys Cys Gly Thr Thr Gly Cys Gly Cys Cys Cys Thr Cys Gly Ala
        675                 680                 685

Cys Ala Thr Gly Cys Ala Gly Cys Ala Ala Gly Cys Cys Cys Ala Cys
    690                 695                 700

Gly Thr Gly Cys Cys Cys Ala Cys Cys Cys Cys Cys Thr Gly Ala Ala
705                 710                 715                 720

Cys Thr Cys Cys Thr Gly Gly Gly Gly Gly Gly Ala Cys Cys Gly Thr
                725                 730                 735

Cys Thr Gly Thr Cys Thr Thr Cys Ala Thr Cys Thr Thr Cys Cys Cys
            740                 745                 750

Cys Cys Cys Ala Ala Ala Ala Cys Cys Cys Ala Ala Gly Gly Ala Cys
        755                 760                 765

Ala Cys Cys Cys Thr Cys Ala Thr Gly Ala Thr Cys Thr Cys Ala Cys
```

-continued

```
                770                 775                 780
Gly Cys Ala Cys Cys Cys Cys Gly Ala Gly Gly Thr Cys Ala Cys
785                 790                 795                 800

Ala Thr Gly Cys Gly Thr Gly Gly Thr Gly Gly Thr Gly Gly Ala Cys
                805                 810                 815

Gly Thr Gly Ala Gly Cys Cys Ala Gly Gly Ala Thr Gly Ala Cys Cys
                820                 825                 830

Cys Gly Ala Gly Gly Thr Gly Cys Ala Gly Thr Thr Cys Ala Cys
            835                 840                 845

Ala Thr Gly Gly Thr Ala Cys Ala Thr Ala Ala Cys Ala Ala Cys
850                 855                 860

Gly Ala Gly Cys Ala Gly Gly Thr Gly Cys Gly Cys Ala Cys Cys Gly
865                 870                 875                 880

Cys Cys Cys Gly Gly Cys Gly Cys Cys Gly Cys Thr Ala Cys Gly
            885                 890                 895

Gly Gly Ala Gly Cys Ala Gly Cys Ala Gly Thr Thr Cys Ala Ala Cys
                900                 905                 910

Ala Gly Cys Ala Cys Gly Ala Thr Cys Gly Cys Gly Thr Gly Gly
                915                 920                 925

Thr Cys Ala Gly Cys Ala Cys Cys Thr Cys Cys Cys Ala Thr
            930                 935                 940

Cys Gly Cys Gly Cys Ala Cys Ala Gly Gly Ala Cys Thr Gly Gly
945                 950                 955                 960

Cys Thr Gly Ala Gly Gly Gly Cys Ala Ala Gly Gly Ala Gly Thr
                965                 970                 975

Thr Cys Ala Ala Gly Thr Gly Cys Ala Ala Gly Thr Cys Cys Ala
            980                 985                 990

Cys Ala Ala Cys Ala Ala Gly Gly Cys Ala Cys Thr Cys Cys Cys Gly
                995                 1000                1005

Gly Cys Cys Cys Cys Cys Ala Thr Cys Gly Ala Gly Ala Ala Ala
            1010                1015                1020

Cys Cys Ala Thr Cys Thr Cys Cys Ala Ala Ala Gly Cys Cys Ala Gly
1025                1030                1035                1040

Ala Gly Gly Gly Cys Ala Gly Cys Cys Cys Thr Gly Gly Ala Gly
            1045                1050                1055

Cys Cys Gly Ala Ala Gly Gly Thr Cys Thr Ala Cys Ala Cys Cys Ala
            1060                1065                1070

Thr Gly Gly Gly Cys Cys Cys Thr Cys Cys Cys Gly Gly Gly Ala
            1075                1080                1085

Gly Gly Ala Gly Cys Thr Gly Ala Gly Cys Ala Gly Cys Ala Gly Gly
            1090                1095                1100

Thr Cys Gly Gly Thr Cys Ala Gly Cys Thr Gly Ala Cys Cys Thr
1105                1110                1115                1120

Gly Cys Ala Thr Gly Ala Thr Cys Ala Ala Cys Gly Gly Cys Thr Thr
            1125                1130                1135

Cys Thr Ala Cys Cys Cys Thr Cys Cys Gly Ala Cys Ala Thr Cys
            1140                1145                1150

Thr Cys Gly Gly Thr Gly Gly Ala Gly Thr Gly Gly Ala Gly Ala
            1155                1160                1165

Ala Gly Ala Ala Cys Gly Gly Gly Ala Ala Gly Gly Cys Ala Gly Ala
            1170                1175                1180

Gly Gly Ala Cys Ala Ala Cys Thr Ala Cys Ala Ala Gly Ala Cys Cys
1185                1190                1195                1200
```

```
Ala Cys Gly Cys Cys Gly Gly Cys Cys Gly Thr Gly Cys Thr Gly Gly
            1205                1210                1215

Ala Cys Ala Gly Cys Gly Ala Cys Gly Gly Cys Thr Cys Cys Thr Ala
        1220                1225                1230

Cys Thr Thr Cys Cys Thr Cys Thr Ala Cys Ala Ala Cys Ala Ala Gly
    1235                1240                1245

Cys Thr Cys Thr Cys Ala Gly Cys Gly Cys Cys Ala Cys Gly Ala
        1250                1255                1260

Gly Thr Gly Ala Gly Thr Gly Cys Ala Gly Cys Gly Gly Gly
1265                1270                1275                1280

Cys Gly Ala Cys Gly Thr Cys Thr Thr Cys Ala Cys Cys Thr Gly Cys
            1285                1290                1295

Thr Cys Cys Gly Thr Gly Ala Thr Gly Cys Ala Cys Gly Ala Gly Gly
        1300                1305                1310

Cys Cys Thr Thr Gly Cys Ala Cys Ala Ala Cys Cys Ala Cys Thr Ala
    1315                1320                1325

Cys Ala Cys Gly Cys Ala Gly Ala Ala Gly Thr Cys Cys Ala Thr Cys
        1330                1335                1340

Thr Cys Cys Cys Gly Cys Thr Cys Thr Cys Cys Gly Gly Gly Thr Ala
1345                1350                1355                1360

Ala Ala

<210> SEQ ID NO 23
<211> LENGTH: 5
<212> TYPE: PRT
<213> ORGANISM: Oryctolagus cuniculus

<400> SEQUENCE: 23

Ser Tyr Asp Met Thr
 1               5

<210> SEQ ID NO 24
<211> LENGTH: 5
<212> TYPE: PRT
<213> ORGANISM: Oryctolagus cuniculus

<400> SEQUENCE: 24

Ser Tyr Asp Met Ser
 1               5

<210> SEQ ID NO 25
<211> LENGTH: 5
<212> TYPE: PRT
<213> ORGANISM: Oryctolagus cuniculus

<400> SEQUENCE: 25

Asp Tyr Asp Leu Ser
 1               5

<210> SEQ ID NO 26
<211> LENGTH: 5
<212> TYPE: PRT
<213> ORGANISM: Oryctolagus cuniculus

<400> SEQUENCE: 26

Ser Tyr Asp Met Ser
 1               5

<210> SEQ ID NO 27
```

```
<210> SEQ ID NO 27
<211> LENGTH: 8
<212> TYPE: PRT
<213> ORGANISM: Oryctolagus cuniculus

<400> SEQUENCE: 27

Tyr Ala Ser Gly Ser Thr Tyr Tyr
1               5

<210> SEQ ID NO 28
<211> LENGTH: 8
<212> TYPE: PRT
<213> ORGANISM: Oryctolagus cuniculus

<400> SEQUENCE: 28

Ser Ser Ser Gly Thr Thr Tyr Tyr
1               5

<210> SEQ ID NO 29
<211> LENGTH: 8
<212> TYPE: PRT
<213> ORGANISM: Oryctolagus cuniculus

<400> SEQUENCE: 29

Tyr Ala Ser Gly Ser Thr Tyr Tyr
1               5

<210> SEQ ID NO 30
<211> LENGTH: 8
<212> TYPE: PRT
<213> ORGANISM: Oryctolagus cuniculus

<400> SEQUENCE: 30

Ala Ile Asp Gly Asn Pro Tyr Tyr
1               5

<210> SEQ ID NO 31
<211> LENGTH: 8
<212> TYPE: PRT
<213> ORGANISM: Oryctolagus cuniculus

<400> SEQUENCE: 31

Ser Thr Ala Tyr Asn Ser His Tyr
1               5

<210> SEQ ID NO 32
<211> LENGTH: 11
<212> TYPE: PRT
<213> ORGANISM: Oryctolagus cuniculus

<400> SEQUENCE: 32

Glu His Ala Gly Tyr Ser Gly Asp Thr Gly His
1               5                   10

<210> SEQ ID NO 33
<211> LENGTH: 8
<212> TYPE: PRT
<213> ORGANISM: Oryctolagus cuniculus

<400> SEQUENCE: 33

Glu Gly Ala Gly Val Ser Met Thr
1               5

<210> SEQ ID NO 34
<211> LENGTH: 8
<212> TYPE: PRT
```

```
<213> ORGANISM: Oryctolagus cuniculus

<400> SEQUENCE: 34

Glu Asp Ala Gly Phe Ser Asn Ala
 1               5

<210> SEQ ID NO 35
<211> LENGTH: 4
<212> TYPE: PRT
<213> ORGANISM: Oryctolagus cuniculus

<400> SEQUENCE: 35

Gly Ala Gly Asp
 1

<210> SEQ ID NO 36
<211> LENGTH: 6
<212> TYPE: PRT
<213> ORGANISM: Oryctolagus cuniculus

<400> SEQUENCE: 36

Gly Gly Ser Trp Leu Asp
 1               5

<210> SEQ ID NO 37
<211> LENGTH: 5
<212> TYPE: PRT
<213> ORGANISM: Oryctolagus cuniculus

<400> SEQUENCE: 37

Arg Cys Ala Tyr Asp
 1               5

<210> SEQ ID NO 38
<211> LENGTH: 6
<212> TYPE: PRT
<213> ORGANISM: Oryctolagus cuniculus

<400> SEQUENCE: 38

Arg Cys Ala Asp Val Val
 1               5

<210> SEQ ID NO 39
<211> LENGTH: 5
<212> TYPE: PRT
<213> ORGANISM: Oryctolagus cuniculus

<400> SEQUENCE: 39

Arg Cys Ala Leu Val
 1               5

<210> SEQ ID NO 40
<211> LENGTH: 6
<212> TYPE: PRT
<213> ORGANISM: Oryctolagus cuniculus

<400> SEQUENCE: 40

Gln Ser Ile Ser Thr Tyr
 1               5

<210> SEQ ID NO 41
<211> LENGTH: 6
<212> TYPE: PRT
<213> ORGANISM: Oryctolagus cuniculus
```

```
<400> SEQUENCE: 41

Gln Ser Val Ser Ser Tyr
 1               5

<210> SEQ ID NO 42
<211> LENGTH: 6
<212> TYPE: PRT
<213> ORGANISM: Oryctolagus cuniculus

<400> SEQUENCE: 42

Glu Ser Ile Ser Asn Tyr
 1               5

<210> SEQ ID NO 43
<211> LENGTH: 8
<212> TYPE: PRT
<213> ORGANISM: Oryctolagus cuniculus

<400> SEQUENCE: 43

Lys Asn Val Tyr Asn Asn Asn Trp
 1               5

<210> SEQ ID NO 44
<211> LENGTH: 12
<212> TYPE: PRT
<213> ORGANISM: Oryctolagus cuniculus

<400> SEQUENCE: 44

Gln Gln Gly Tyr Thr His Ser Asn Val Asp Asn Val
 1               5                  10

<210> SEQ ID NO 45
<211> LENGTH: 12
<212> TYPE: PRT
<213> ORGANISM: Oryctolagus cuniculus

<400> SEQUENCE: 45

Gln Gln Gly Tyr Ser Ile Ser Asp Ile Asp Asn Ala
 1               5                  10

<210> SEQ ID NO 46
<211> LENGTH: 14
<212> TYPE: PRT
<213> ORGANISM: Oryctolagus cuniculus

<400> SEQUENCE: 46

Gln Cys Thr Ser Gly Gly Lys Phe Ile Ser Asp Gly Ala Ala
 1               5                  10

<210> SEQ ID NO 47
<211> LENGTH: 11
<212> TYPE: PRT
<213> ORGANISM: Oryctolagus cuniculus

<400> SEQUENCE: 47

Ala Gly Asp Tyr Ser Ser Ser Ser Asp Asn Gly
 1               5                  10

<210> SEQ ID NO 48
<211> LENGTH: 12
<212> TYPE: PRT
<213> ORGANISM: Oryctolagus cuniculus

<400> SEQUENCE: 48
```

```
Gln Ala Thr His Tyr Ser Ser Asp Trp Leu Thr Tyr
 1               5                  10
```

<210> SEQ ID NO 49
<211> LENGTH: 5
<212> TYPE: RNA
<213> ORGANISM: Artificial Sequence
<220> FEATURE:
<223> OTHER INFORMATION: AU-rich sequence

<400> SEQUENCE: 49 auuua                                                                 5

<210> SEQ ID NO 50
<211> LENGTH: 6
<212> TYPE: RNA
<213> ORGANISM: Artificial Sequence
<220> FEATURE:
<223> OTHER INFORMATION: AU-rich sequence

<400> SEQUENCE: 50 auuuua                                                                6

<210> SEQ ID NO 51
<211> LENGTH: 7
<212> TYPE: RNA
<213> ORGANISM: Artificial Sequence
<220> FEATURE:
<223> OTHER INFORMATION: AU-rich sequence

<400> SEQUENCE: 51 auuuuua                                                               7

<210> SEQ ID NO 52
<211> LENGTH: 157
<212> TYPE: PRT
<213> ORGANISM: Oryctolagus cuniculus

<400> SEQUENCE: 52

```
Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
                20                  25                  30

Gly Thr Pro Leu Thr Leu Thr Cys Thr Val Ser Gly Phe Ser Leu Ser
                35                  40                  45

Ser Tyr Asp Met Thr Trp Val Arg Gln Ala Pro Gly Lys Gly Leu Glu
    50                  55                  60

Trp Ile Gly Ile Ile Tyr Ala Ser Gly Ser Thr Tyr Tyr Ala Ser Trp
65                  70                  75                  80

Ala Lys Gly Arg Phe Thr Ile Ser Lys Thr Ser Thr Val Asp Leu
                85                  90                  95

Glu Val Thr Ser Leu Thr Thr Glu Asp Thr Ala Thr Tyr Phe Cys Ser
                100                 105                 110

Arg Glu His Ala Gly Tyr Ser Gly Asp Thr Gly His Leu Trp Gly Pro
                115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser
145                 150                 155
```

<210> SEQ ID NO 53

```
<211> LENGTH: 154
<212> TYPE: PRT
<213> ORGANISM: Oryctolagus cuniculus

<400> SEQUENCE: 53

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Ser Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Tyr Ile Gly Ile Ile Ser Ser Gly Thr Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Val Thr Ser Pro Thr Ile Gly Asp Thr Ala Thr Tyr Phe Cys Ala
            100                 105                 110

Arg Glu Gly Ala Gly Val Ser Met Thr Leu Trp Gly Pro Gly Thr Leu
            115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser
145                 150

<210> SEQ ID NO 54
<211> LENGTH: 154
<212> TYPE: PRT
<213> ORGANISM: Oryctolagus cuniculus

<400> SEQUENCE: 54

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Ala Ser Gly Ser Thr Tyr Tyr Ala Ser Trp
65                  70                  75                  80

Ala Lys Gly Arg Val Ala Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Glu Asp Ala Gly Phe Ser Asn Ala Leu Trp Gly Pro Gly Thr Leu
            115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser
145                 150

<210> SEQ ID NO 55
<211> LENGTH: 147
<212> TYPE: PRT
<213> ORGANISM: Oryctolagus cuniculus
```

<400> SEQUENCE: 55

Met Asp Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Ile Ser Thr Tyr Leu Asp Trp Tyr Gln Gln Lys Pro Gly Gln
    50                  55                  60

Pro Pro Lys Leu Leu Ile Tyr Asp Ala Ser Asp Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Thr His Ser Asn Val Asp Asn Val Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser
145

<210> SEQ ID NO 56
<211> LENGTH: 147
<212> TYPE: PRT
<213> ORGANISM: Oryctolagus cuniculus

<400> SEQUENCE: 56

Met Asp Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Ala Ile Lys Cys Gln Ala Ser
        35                  40                  45

Gln Ser Val Ser Ser Tyr Leu Ala Trp Tyr Gln Gln Lys Pro Gly Gln
    50                  55                  60

Pro Pro Lys Pro Leu Ile Tyr Glu Ala Ser Met Leu Ala Ala Gly Val
65                  70                  75                  80

Ser Ser Arg Phe Lys Gly Ser Gly Ser Gly Thr Asp Phe Thr Leu Thr
                85                  90                  95

Ile Ser Asp Leu Glu Cys Asp Asp Ala Ala Thr Tyr Tyr Cys Gln Gln
            100                 105                 110

Gly Tyr Ser Ile Ser Asp Ile Asp Asn Ala Phe Gly Gly Gly Thr Glu
        115                 120                 125

Val Val Val Lys Gly Asp Pro Val Ala Pro Thr Val Leu Leu Phe Pro
    130                 135                 140

Pro Ser Ser
145

<210> SEQ ID NO 57
<211> LENGTH: 150
<212> TYPE: PRT
<213> ORGANISM: Oryctolagus cuniculus

<400> SEQUENCE: 57

```
Met Asp Met Arg Ala Pro Thr Gln Leu Leu Gly Leu Leu Leu Trp
1               5                  10                  15

Leu Pro Gly Ala Arg Cys Ala Asp Val Val Met Thr Gln Thr Pro Ala
            20                  25                  30

Ser Val Ser Ala Ala Val Gly Gly Thr Val Thr Ile Asn Cys Gln Ala
        35                  40                  45

Ser Glu Ser Ile Ser Asn Tyr Leu Ser Trp Tyr Gln Gln Lys Pro Gly
50                  55                  60

Gln Pro Pro Lys Leu Leu Ile Tyr Arg Thr Ser Thr Leu Ala Ser Gly
65                  70                  75                  80

Val Ser Ser Arg Phe Lys Gly Ser Gly Ser Gly Thr Glu Tyr Thr Leu
                85                  90                  95

Thr Ile Ser Gly Val Gln Cys Asp Asp Val Ala Thr Tyr Tyr Cys Gln
            100                 105                 110

Cys Thr Ser Gly Gly Lys Phe Ile Ser Asp Gly Ala Ala Phe Gly Gly
        115                 120                 125

Gly Thr Glu Val Val Val Lys Gly Asp Pro Val Ala Pro Thr Val Leu
130                 135                 140

Leu Phe Pro Pro Ser Ser
145                 150

<210> SEQ ID NO 58
<211> LENGTH: 236
<212> TYPE: PRT
<213> ORGANISM: Oryctolagus cuniculus

<400> SEQUENCE: 58

Met Asp Met Arg Ala Pro Thr Gln Leu Leu Gly Leu Leu Leu Leu Trp
1               5                  10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Ser Ile Ser Thr Tyr Leu Asp Trp Tyr Gln Gln Lys Pro Gly Gln
50                  55                  60

Pro Pro Lys Leu Leu Ile Tyr Asp Ala Ser Asp Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Thr His Ser Asn Val Asp Asn Val Phe Gly Gly Gly Thr Glu
        115                 120                 125

Val Val Val Lys Gly Asp Pro Val Ala Pro Thr Val Leu Leu Phe Pro
130                 135                 140

Pro Ser Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
210                 215                 220
```

Thr Ser Val Val Gln Ser Phe Ser Arg Lys Asn Cys
225                 230                 235

<210> SEQ ID NO 59
<211> LENGTH: 711
<212> TYPE: DNA
<213> ORGANISM: Oryctolagus cuniculus

<400> SEQUENCE: 59

```
atggacatga gggcccccac tcagctgctg gggctcctgc tgctctggct cccaggtgcc    60
agatgtgcct atgatatgac ccagactcca gcctctgtgg aggtagctgt gggaggcaca   120
gtcaccatca agtgccaggc cagtcagagc attagtacct acttagactg gtatcagcag   180
aaaccagggc agcctcccaa gctcctgatc tatgatgcat ccgatctggc atctggggtc   240
ccatcgcggt tcaaaggcag tggatctggg acacagttca ctctcaccat cagcgacctg   300
gagtgtgccg atgctgccac ttactactgt caacagggtt atacacatag taatgttgat   360
aatgttttcg gcggagggac cgaggtggtg gtcaaaggtg atccagttgc acctactgtc   420
ctcctcttcc caccatctag cgatgaggtg gcaactggaa cagtcaccat cgtgtgtgtg   480
gcgaataaat actttcccga tgtcaccgtc acctgggagg tggatggcac cacccaaaca   540
actggcatcg agaacagtaa aacaccgcag aattctgcag attgtaccta caacctcagc   600
agcactctga cactgaccag cacacagtac aacagccaca agagtacac ctgcaaggtg    660
acccagggca cgacctcagt cgtccagagc ttcagtagga agaactgtta a            711
```

<210> SEQ ID NO 60
<211> LENGTH: 456
<212> TYPE: PRT
<213> ORGANISM: Oryctolagus cuniculus

<400> SEQUENCE: 60

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Asp Met Thr Trp Val Arg Gln Ala Pro Gly Lys Gly Leu Glu
    50                  55                  60

Trp Ile Gly Ile Ile Tyr Ala Ser Gly Thr Thr Tyr Tyr Ala Asn Trp
65                  70                  75                  80

Ala Lys Gly Arg Phe Thr Ile Ser Lys Thr Ser Thr Thr Val Asp Leu
                85                  90                  95

Lys Val Thr Ser Pro Thr Ile Gly Asp Thr Ala Thr Tyr Phe Cys Ala
            100                 105                 110

Arg Glu Gly Ala Gly Val Ser Met Thr Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

-continued

```
Ser Gly Leu Tyr Ser Leu Ser Ser Val Val Ser Val Thr Ser Ser Ser
            195                 200                 205
Gln Pro Val Thr Cys Asn Val Ala His Pro Ala Thr Asn Thr Lys Val
        210                 215                 220
Asp Lys Thr Val Ala Pro Ser Thr Cys Ser Lys Pro Thr Cys Pro Pro
225                 230                 235                 240
Pro Glu Leu Leu Gly Gly Pro Ser Val Phe Ile Phe Pro Pro Lys Pro
                245                 250                 255
Lys Asp Thr Leu Met Ile Ser Arg Thr Pro Glu Val Thr Cys Val Val
            260                 265                 270
Val Asp Val Ser Gln Asp Asp Pro Glu Val Gln Phe Thr Trp Tyr Ile
        275                 280                 285
Asn Asn Glu Gln Val Arg Thr Ala Arg Pro Pro Leu Arg Glu Gln Gln
290                 295                 300
Phe Asn Ser Thr Ile Arg Val Val Ser Thr Leu Pro Ile Ala His Gln
305                 310                 315                 320
Asp Trp Leu Arg Gly Lys Glu Phe Lys Cys Lys Val His Asn Lys Ala
                325                 330                 335
Leu Pro Ala Pro Ile Glu Lys Thr Ile Ser Lys Ala Arg Gly Gln Pro
            340                 345                 350
Leu Glu Pro Lys Val Tyr Thr Met Gly Pro Pro Arg Glu Glu Leu Ser
        355                 360                 365
Ser Arg Ser Val Ser Leu Thr Cys Met Ile Asn Gly Phe Tyr Pro Ser
370                 375                 380
Asp Ile Ser Val Glu Trp Glu Lys Asn Gly Lys Ala Glu Asp Asn Tyr
385                 390                 395                 400
Lys Thr Thr Pro Ala Val Leu Asp Ser Asp Gly Ser Tyr Phe Leu Tyr
                405                 410                 415
Asn Lys Leu Ser Val Pro Thr Ser Glu Trp Gln Arg Gly Asp Val Phe
            420                 425                 430
Thr Cys Ser Val Met His Glu Ala Leu His Asn His Tyr Thr Gln Lys
        435                 440                 445
Ser Ile Ser Arg Ser Pro Gly Lys
450                 455
```

<210> SEQ ID NO 61
<211> LENGTH: 1368
<212> TYPE: DNA
<213> ORGANISM: Oryctolagus cuniculus

<400> SEQUENCE: 61

```
atggagacag gcctgcgctg gcttctcctg gtcgctgtgc tcaaaggtgt ccagtgtcag      60
tcggtggagg agtccggggg tcgcctggtc acgcctggga ccccctgac actcacctgc     120
acagtctctg gattctccct cagcagctac gacatgacct gggtccgcca ggctccaggg     180
aaggggctgg aatggatcgg aatcatttat gctagtggta ccacatacta cgcgaactgg     240
gcgaaaggcc gattcaccat ctccaaaacc tcgaccacgg tggatctgaa agtcaccagt     300
ccgacaatcg gggacacggc cacctatttc tgtgccagag agggggctgg tgttagtatg     360
accttgtggg gccaggcac cctggtcacc gtctcctcag gcaacctaa ggctccatca     420
gtcttcccac tggccccctg ctgcgggac acaccctcta gcacggtgac cttgggctgc     480
ctggtcaaag gctacctccc ggagccagtg accgtgacct ggaactcggg caccctcacc     540
aatggggtac gcaccttccc gtccgtccgg cagtcctcag gcctctactc gctgagcagc     600
```

```
gtggtgagcg tgacctcaag cagccagccc gtcacctgca acgtggccca cccagccacc    660
aacaccaaag tggacaagac cgttgcgccc tcgacatgca gcaagcccac gtgcccaccc    720
cctgaactcc tgggggggacc gtctgtcttc atcttccccc caaaacccaa ggacaccctc    780
atgatctcac gcaccccga ggtcacatgc gtggtggtgg acgtgagcca ggatgacccc    840
gaggtgcagt tcacatggta cataaacaac gagcaggtgc gcaccgcccg ccgccgccta    900
cgggagcagc agttcaacag cacgatccgc gtggtcagca ccctccccat cgcgcaccag    960
gactggctga ggggcaagga gttcaagtgc aaagtccaca acaaggcact cccgccccc    1020 atcgagaaaa ccatctccaa agccagaggg cagcccctgg agccgaaggt ctacaccatg    1080
ggccctcccc gggaggagct gagcagcagg tcggtcagcc tgacctgcat gatcaacggc    1140
ttctacccct ccgacatctc ggtggagtgg gagaagaacg ggaaggcaga ggacaactac    1200
aagaccacgc cggccgtgct ggacagcgac ggctcctact cctctacaa caagctctca    1260 gtgcccacga gtgagtggca gcggggcgac gtcttcacct gctccgtgat gcacgaggcc    1320
ttgcacaacc actacacgca gaagtccatc tcccgctctc cgggtaaa              1368
```

<210> SEQ ID NO 62
<211> LENGTH: 236
<212> TYPE: PRT
<213> ORGANISM: Oryctolagus cuniculus

<400> SEQUENCE: 62

```
Met Asp Met Arg Ala Pro Thr Gln Leu Leu Gly Leu Leu Leu Leu Trp
  1               5                  10                  15

Leu Pro Gly Ala Arg Cys Ala Tyr Asp Met Thr Gln Thr Pro Ala Ser
             20                  25                  30

Val Glu Val Ala Val Gly Gly Thr Val Ala Ile Lys Cys Gln Ala Ser
         35                  40                  45

Gln Ser Val Ser Ser Tyr Leu Ala Trp Tyr Gln Gln Lys Pro Gly Gln
     50                  55                  60

Pro Pro Lys Pro Leu Ile Tyr Glu Ala Ser Met Leu Ala Ala Gly Val
 65                  70                  75                  80

Ser Ser Arg Phe Lys Gly Ser Gly Ser Gly Thr Asp Phe Thr Leu Thr
                 85                  90                  95

Ile Ser Asp Leu Glu Cys Asp Asp Ala Ala Thr Tyr Tyr Cys Gln Gln
            100                 105                 110

Gly Tyr Ser Ile Ser Asp Ile Asp Asn Ala Phe Gly Gly Gly Thr Glu
        115                 120                 125

Val Val Val Lys Gly Asp Pro Val Ala Pro Thr Val Leu Leu Phe Pro
    130                 135                 140

Pro Ser Asp Glu Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Ser Arg Lys Asn Cys
225                 230                 235
```

<210> SEQ ID NO 63
<211> LENGTH: 711
<212> TYPE: DNA
<213> ORGANISM: Oryctolagus cuniculus

<400> SEQUENCE: 63

| | | | | | |
|---|---|---|---|---|---|
| atggacatga | gggcccccac | tcaactgctg | gggctcctgc | tgctctggct | cccaggtgcc | 60 |
| agatgtgcct | atgatatgac | ccagactcca | gcctctgtgg | aggtagctgt | gggaggcaca | 120 |
| gtcgccatca | agtgccaggc | cagtcagagc | gttagtagtt | acttagcctg | gtatcagcag | 180 |
| aaaccagggc | agcctcccaa | gcccctgatc | tacgaagcat | ccatgctggc | ggctggggtc | 240 |
| tcatcgcggt | tcaaaggcag | tggatctggg | acagacttca | ctctcaccat | cagcgacctg | 300 |
| gagtgtgacg | atgctgccac | ttactattgt | caacagggtt | attctatcag | tgatattgat | 360 |
| aatgctttcg | gcggagggac | cgaggtggtg | gtcaaaggtg | atccagttgc | acctactgtc | 420 |
| ctcctcttcc | caccatctag | cgatgaggtg | gcaactggaa | cagtcaccat | cgtgtgtgtg | 480 |
| gcgaataaat | actttcccga | tgtcaccgtc | acctgggagg | tggatggcac | cacccaaaca | 540 |
| actggcatcg | agaacagtaa | aacaccgcag | aattctgcag | attgtaccta | caacctcagc | 600 |
| agcactctga | cactgaccag | cacacagtac | aacagccaca | aagagtacac | ctgcaaggtg | 660 |
| acccagggca | cgacctcagt | cgtccagagc | ttcagtagga | agaactgtta | a | 711 |

<210> SEQ ID NO 64
<211> LENGTH: 459
<212> TYPE: PRT
<213> ORGANISM: Oryctolagus cuniculus

<400> SEQUENCE: 64

Met Glu Thr Gly Leu Arg Trp Leu Leu Leu Val Ala Val Leu Lys Gly
1               5                   10                  15

Val Gln Cys Gln Ser Val Glu Ser Gly Gly Arg Leu Val Ser Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Tyr Ile Gly Ile Ile Ser Ser Gly Ser Thr Tyr Tyr Ala Ser Trp
65                  70                  75                  80

Ala Lys Gly Arg Phe Thr Ile Ser Lys Thr Ser Thr Thr Val Asp Leu
                85                  90                  95

Glu Val Thr Ser Leu Thr Thr Glu Asp Thr Ala Thr Tyr Phe Cys Ser
            100                 105                 110

Arg Glu His Ala Gly Tyr Ser Gly Asp Thr Gly His Leu Trp Gly Pro
        115                 120                 125

Gly Thr Leu Val Thr Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
            245                 250                 255

Pro Lys Pro Lys Asp Thr Leu Met Ile Ser Arg Thr Pro Glu Val Thr
        260                 265                 270

Cys Val Val Val Asp Val Ser Gln Asp Pro Glu Val Gln Phe Thr
    275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
            325                 330                 335

Asn Lys Ala Leu Pro Ala Pro Ile Glu Lys Thr Ile Ser Lys Ala Arg
        340                 345                 350

Gly Gln Pro Leu Glu Pro Lys Val Tyr Thr Met Gly Pro Pro Arg Glu
    355                 360                 365

Glu Leu Ser Ser Arg Ser Val Ser Leu Thr Cys Met Ile Asn Gly Phe
370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
            405                 410                 415

Phe Leu Tyr Asn Lys Leu Ser Val Pro Thr Ser Glu Trp Gln Arg Gly
        420                 425                 430

Asp Val Phe Thr Cys Ser Val Met His Glu Ala Leu His Asn His Tyr
    435                 440                 445

Thr Gln Lys Ser Ile Ser Arg Ser Pro Gly Lys
    450                 455

<210> SEQ ID NO 65
<211> LENGTH: 1377
<212> TYPE: DNA
<213> ORGANISM: Oryctolagus cuniculus

<400> SEQUENCE: 65
atggagacag gcctgcgctg gcttctcctg gtcgctgtgc tcaaaggtgt ccagtgtcag      60
tcggtggagg agtccggggg tcgcctggtc tcgcctggga cccccctgac actcacctgc     120
acagcctctg gattctcccct cagtagctac gacatgagct gggtccgcca ggctccaggg     180
aaggggctgg aatacatcgg aatcattagt agtagtggta gcacatacta cgcgagctgg     240
gcgaaaggcc gattcaccat ctccaaaacc tcgaccacgg tggatctgga agtgaccagt     300
ctgacaaccg aggacacggc cacctatttc tgtagtagag acatgctggg ttatagtggt     360
gatacgggtc acttgtgggg cccaggcacc ctggtcaccg tctcctcggg caacctaag      420 gctccatcag tcttcccact ggccccctgc tgcgggaca cccctctag cacggtgacc       480 ttgggctgcc tggtcaaagg ctacctcccg gagccagtga ccgtgacctg gaactcgggc     540
accctcacca tgggtacg caccttcccg tccgtccggc agtcctcagg cctctactcg       600
ctgagcagcg tggtgagcgt gacctcaagc agccagcccg tcacctgcaa cgtggcccac     660

-continued

```
ccagccacca acaccaaagt ggacaagacc gttgcgccct cgacatgcag caagcccacg    720
tgcccacccc ctgaactcct gggggggaccg tctgtcttca tcttcccccc aaaacccaag    780

gacaccctca tgatctcacg cacccccgag gtcacatgcg tggtggtgga cgtgagccag    840
gatgaccccg aggtgcagtt cacatggtac ataaacaacg agcaggtgcg caccgcccgg    900
ccgccgctac gggagcagca gttcaacagc acgatccgcg tggtcagcac cctccccatc    960
gcgcaccagg actggctgag gggcaaggag ttcaagtgca aagtccacaa caaggcactc   1020
ccggccccca tcgagaaaac catctccaaa gccagagggc agcccctgga gccgaaggtc   1080
tacaccatgg gccctccccg ggaggagctg agcagcaggt cggtcagcct gacctgcatg   1140
atcaacggct tctacccttc cgacatctcg gtggagtggg agaagaacgg gaaggcagag   1200
gacaactaca agaccacgcc ggccgtgctg gacagcgacg gctcctactt cctctacaac   1260
aagctctcag tgcccacgag tgagtggcag cggggcgacg tcttcacctg ctccgtgatg   1320
cacgaggcct tgcacaacca ctacacgcag aagtccatct cccgctctcc gggtaaa      1377
```

```

<210> SEQ ID NO 66
<211> LENGTH: 150
<212> TYPE: PRT
<213> ORGANISM: Oryctolagus cuniculus

<400> SEQUENCE: 66

Met Glu Thr Gly Leu Arg Trp Leu Leu Leu Val Ala Val Leu Lys Gly
 1               5                  10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Thr Ile Ser
        35                  40                  45

Asp Tyr Asp Leu Ser Trp Val Arg Gln Ala Pro Gly Glu Gly Leu Lys
    50                  55                  60

Tyr Ile Gly Phe Ile Ala Ile Asp Gly Asn Pro Tyr Tyr Ala Thr Trp
65                  70                  75                  80

Ala Lys Gly Arg Phe Thr Ile Ser Lys Thr Ser Thr Thr Val Asp Leu
                85                  90                  95

Lys Ile Thr Ala Pro Thr Thr Glu Asp Thr Ala Thr Tyr Phe Cys Ala
            100                 105                 110

Arg Gly Ala Gly Asp Leu Trp Gly Pro Gly Thr Leu Val Thr Val Ser
        115                 120                 125

Ser Gly Gln Pro Lys Ala Pro Ser Val Phe Pro Leu Ala Pro Cys Cys
    130                 135                 140

Gly Asp Thr Pro Ser Ser
145                 150

<210> SEQ ID NO 67
<211> LENGTH: 152
<212> TYPE: PRT
<213> ORGANISM: Oryctolagus cuniculus

<400> SEQUENCE: 67

Met Glu Thr Gly Leu Arg Trp Leu Leu Leu Val Ala Val Leu Lys Gly
 1               5                  10                  15

Val His Cys Gln Ser Val Glu Glu Ser Gly Gly Arg Leu Val Thr Pro
            20                  25                  30

Gly Thr Pro Leu Thr Leu Thr Cys Thr Ala Ser Gly Phe Ser Arg Ser
        35                  40                  45
```

```
Ser Tyr Asp Met Ser Trp Val Arg Gln Ala Pro Gly Lys Gly Leu Glu
     50                  55                  60

Trp Val Gly Val Ile Ser Thr Ala Tyr Asn Ser His Tyr Ala Ser Trp
 65                  70                  75                  80

Ala Lys Gly Arg Phe Thr Ile Ser Arg Thr Ser Thr Thr Val Asp Leu
                 85                  90                  95

Lys Met Thr Ser Leu Thr Thr Glu Asp Thr Ala Thr Tyr Phe Cys Ala
                100                 105                 110

Arg Gly Gly Ser Trp Leu Asp Leu Trp Gly Gln Gly Thr Leu Val Thr
            115                 120                 125

Val Ser Ser Gly Gln Pro Lys Ala Pro Ser Val Phe Pro Leu Ala Pro
    130                 135                 140

Cys Cys Gly Asp Thr Pro Ser Ser
145                 150

<210> SEQ ID NO 68
<211> LENGTH: 149
<212> TYPE: PRT
<213> ORGANISM: Oryctolagus cuniculus

<400> SEQUENCE: 68

Met Asp Thr Arg Ala Pro Thr Gln Leu Leu Gly Leu Leu Leu Leu Trp
  1               5                  10                  15

Leu Pro Gly Ala Arg Cys Ala Asp Val Val Met Thr Gln Thr Pro Ala
                 20                  25                  30

Ser Val Ser Ala Ala Val Gly Gly Thr Val Thr Ile Asn Cys Gln Ser
             35                  40                  45

Ser Lys Asn Val Tyr Asn Asn Asn Trp Leu Ser Trp Phe Gln Gln Lys
     50                  55                  60

Pro Gly Gln Pro Pro Lys Leu Leu Ile Tyr Tyr Ala Ser Thr Leu Ala
 65                  70                  75                  80

Ser Gly Val Pro Ser Arg Phe Arg Gly Ser Gly Ser Gly Thr Gln Phe
                 85                  90                  95

Thr Leu Thr Ile Ser Asp Val Gln Cys Asp Asp Ala Ala Thr Tyr Tyr
                100                 105                 110

Cys Ala Gly Asp Tyr Ser Ser Ser Asp Asn Gly Phe Gly Gly Gly
            115                 120                 125

Thr Glu Val Val Val Lys Gly Asp Pro Val Ala Pro Thr Val Leu Leu
    130                 135                 140

Phe Pro Pro Ser Ser
145

<210> SEQ ID NO 69
<211> LENGTH: 149
<212> TYPE: PRT
<213> ORGANISM: Oryctolagus cuniculus
<220> FEATURE:
<221> NAME/KEY: SITE
<222> LOCATION: (1)...(149)
<223> OTHER INFORMATION: Xaa = any amino acid

<400> SEQUENCE: 69

Met Asp Xaa Arg Ala Pro Thr Gln Leu Leu Gly Leu Leu Leu Leu Trp
  1               5                  10                  15

Leu Pro Gly Ala Arg Cys Ala Leu Val Met Thr Gln Thr Pro Ala Ser
                 20                  25                  30

Val Ser Ala Ala Val Gly Gly Thr Val Thr Ile Asn Cys Gln Ser Ser
             35                  40                  45
```

-continued

```
Gln Ser Val Tyr Asp Asn Asp Glu Leu Ser Trp Tyr Gln Gln Lys Pro
    50              55                  60

Gly Gln Pro Pro Lys Leu Leu Ile Tyr Leu Ala Ser Lys Leu Ala Ser
65              70                  75              80

Gly Val Pro Ser Arg Phe Lys Gly Ser Gly Ser Gly Thr Gln Phe Ala
                85                  90              95

Leu Thr Ile Ser Gly Val Gln Cys Asp Asp Ala Ala Thr Tyr Tyr Cys
            100             105                 110

Gln Ala Thr His Tyr Ser Ser Asp Trp Tyr Leu Thr Phe Gly Gly Gly
        115             120                 125

Thr Glu Val Val Lys Gly Asp Pro Val Ala Pro Thr Val Leu Leu
    130             135             140

Phe Pro Pro Ser Ser
145
```